United States Patent [19]
Hasegawa

[11] Patent Number: 5,075,287
[45] Date of Patent: * Dec. 24, 1991

[54] MURAMYL PEPTIDE DERIVATIVES AND IMMUNOREGULATING COMPOSITIONS CONTAINING THEM

[75] Inventor: Akira Hasegawa, Gifu, Japan

[73] Assignee: Nisshin Oil Mills, Inc., Japan

[*] Notice: The portion of the term of this patent subsequent to Jan. 23, 2007 has been disclaimed.

[21] Appl. No.: 485,263

[22] Filed: Feb. 26, 1990

[30] Foreign Application Priority Data

Mar. 3, 1989 [JP] Japan ................................. 1-52468

[51] Int. Cl.$^5$ .......................... C07K 9/00; C07K 5/06; A61K 39/12; A61K 37/02
[52] U.S. Cl. ............................................. 514/8; 514/19; 514/885; 530/322; 424/88; 424/89
[58] Field of Search ................. 514/8, 9, 885, 11, 19; 530/322, 317; 424/88

[56] References Cited

U.S. PATENT DOCUMENTS 4,895,835  1/1990  Hasegawa .............................. 424/89

OTHER PUBLICATIONS

Japanese Published Unexamined Patent Appln. No. 172399/1983.
Japanese Published Unexamined Patent Appln. No. 20297/1984.
Japanese Published Unexamined Patent Appln. No. 275299/1986.
Saishin Igaku, 43, No. 6, pp. 1268-1276 (1988).
Kusumoto et al., Tetrahedion Letters, No. 49, "Synthesis of Long Chain Fatty Acid Esters of N-Acetylmuramyl-L-Alanyl-D-Isoglutamine in Relation to Antitumor Activity", pp. 4899-4902 (1978).
K. Matsumoto et al., Immunostimulants Now and Tomorrow, pp. 79-97 (1987).

*Primary Examiner*—Thurman K. Page
*Assistant Examiner*—Carlos Azpura
*Attorney, Agent, or Firm*—Bryan, Cave, McPheeters & McRoberts

[57] ABSTRACT

Muramyl peptide derivatives of the formula:

(I) [structure with $R_2O$, HO, $CH_3CH$, $C=O$, Ala—isoGln—$OCH_3$, $NH-C-CH_3$, $H,R_1$]

wherein "Ala" is $$-NH-\underset{\underset{CH_3}{|}}{CH}-CO-;$$

"isoGln" is $$-NH-\underset{\underset{CH_2CH_2CO-}{|}}{CH}-;\quad (CONH_2)$$

$R^1$ is $R_3O-$ or $$R_3S-[R_3 \text{ is } -CO-CH_2-\underset{\underset{CO-(CH_2)_q-CH_3}{\overset{|}{O}}}{CH}-(CH_2)_k-CH_3$$

(k is an integer from 8 to 12; q is an integer from 10 to 22) or $R_3$ is $$-CO-\underset{\underset{(CH_2)_n-CH_3}{|}}{CH}-(CH_2)_m-CH_3$$

(m is an integer from 11 to 17; n is an integer from 11 to 17)]; and $R_2$ is hydrogen atom or $-CO-(CH_2)_p-CH_3$ (p is an integer from 8 to 22); which act on in vivo immunomechanism of human beings and livestock (in particular cells relevant immune responses) and are useful as imminoregulating agents.

13 Claims, No Drawings

MURAMYL PEPTIDE DERIVATIVES AND IMMUNOREGULATING COMPOSITIONS CONTAINING THEM

BACKGROUND OF THE INVENTION

1. Field of the Invention

The present invention relates to novel muramyl peptide derivatives. The muramyl peptide derivatives of the present invention acts on in vivo immunomechanism of human beings and livestock (in particular cells relevant to immune responses) and are useful as immunoregulating agents.

2. Description of the Prior Art

Muramyl peptides are known to possess various biological activities. That is, 1they possess in vitro activities such as;

(1) the action on cells related to immune responses (for example, monocytes or macrophages, B cells, T cells, natural killer (NK) cells and the like), (2) the action on cells other than those mentioned above (for example, platelets, endothelial cells, fibroblasts and the like), and (3) the action which activates complement systems.

Further they show in vivo activities such as (1) immunoregulating action, and (2) enhancement of natural resistance [see Saishin Igaku, 43, No. 6, pp. 1268–1276 (1988) in Japan].

Known muramyl peptide derivatives are, for example, B30-muramyl dipeptide [Kusumoto et al; Tetrahedron letters, 49 pp. 4899–4902(1978)], muramyl dipetide-lysine [Matsumoto et al, Immunostimulants, pp. 79–97 (1987)]and those discribed in Japanese Published Unexamined Patent Application Nos. 172399/1983, 20297/1984 and 275299/1986.

However, it is still desired to develop compounds other than the known muramyl dipeptide derivatives which have more excellent activity and less toxicity.

SUMMARY OF THE INVENTION

According to the present invention, a muramyl dipeptide derivative is provided, which is represented with the following formula (I):

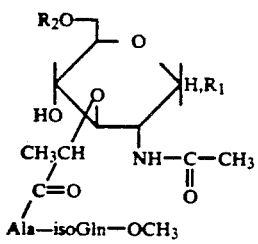 (I)

wherein "Ala" is

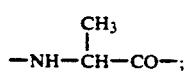

"isoGln" is

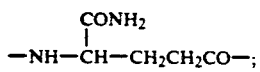

$R_1$ is $R_3O-$ or $R_3S-$

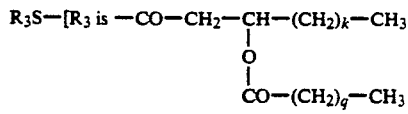

k is an integer from 8 to 12; q is an integer from 10 to 22) or $R_3$ is

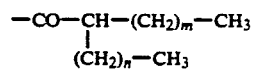

(m is an integer from 11 to 17; n is an integer from 11 to 17)]; and $R_2$ is a hydrogen atom or $-CO-(CH_2)_p-CH_3$ (p is an integer from 8 to 22).

The present invention also provides an immunoregulating composition comprising a compound of the formula (I) and a pharmaceutically acceptable carrier.

DESCRIPTION OF THE PREFERRED EMBODIMENTS

In the formula (I), examples of the groups $R_3$ in the group $-OR_3$ or $-SR_3$ include 3-dodecanoyloxydodecanoyl, 3-tridecanoyloxydodecanoyl, 3-tetradecanoyloxydodecanoyl, 3-pentadecanoyloxydodecanoyl, 3-hexadecanoyloxydodecanoyl, 3-heptadecanoyloxydodecanoyl, 3-octadecanoyloxydodecanoyl, 3-nonadecanoyloxydodecanoyl, 3-eicosanoyloxydodecanoyl, 3-docosanoyloxydodecanoyl, 3-heneicosanoyloxydodecanoyl, 3-tricosanoyloxydodecanoyl, 3-tetracosanoyloxydodecanoyl, 3-dodecanoyloxytridecanoyl, 3-tridecanoyloxytridecanoyl, 3-tetradecanoyloxytridecanoyl, 3-pentadecanoyloxytridecanoyl, 3-hexadecanoyloxytridecanoyl, 3-heptadecanoyloxytridecanoyl, 3-octadecanoyloxytridecanoyl, 3-nonadecanoyloxytridecanoyl, 3-eicosanoyloxytridecanoyl, 3-docosanoyloxytridecanoyl, 3-heneicosanoyloxytridecanoyl, 3-tricosanoyloxytridecanoyl, 3-tetracosanoyloxytridecanoyl, 3-dodecanoyloxytetradecanoyl, 3-tridecanoyloxytetradecanoyl, 3-tetradecanoyloxytetradecanoyl, 3-pentadecanoyloxytetradecanoyl, 3-hexadecanoyloxytetradecanoyl, 3-heptadecanoyloxytetradecanoyl, 3-octadecanoyloxytetradecanoyl, 3-nonadecanoyloxytetradecanoyl, 3-eicosanoyloxytetradecanoyl, 3-docosanoyloxytetradecanoyl, 3-heneicosanoyloxytetradecanoyl, 3-tricosanoyloxytetradecanoyl, 3-tetracosanoyloxytetradecanoyl, 3-dodecanoyloxypentadecanoyl, 3-tridecanoyloxypentadecanoyl, 3-tetradecanoyloxypentadecanoyl, 3-pentadecanoyloxypentadecanoyl, 3-hexadecanoyloxypentadecanoyl, 3-heptadecanoyloxypentadedanoyl, 3-octadecanoyloxypentadecanoyl, 3-nonadecanoyloxypentadecanoyl, 3-eicosanoyloxypentadecanoyl, 3-docosanoyloxypentadecanoyl, 3-heneicosanoyloxypentadecanoyl, 3-tricosnoyloxypentadecanoyl, 3-tetracosanoyloxypentadecanoyl, 3-dodecanoyloxyhexadecanoyl, 3-tridecanoyloxyhexadecanoyl, 3-tetradecanoyloxyhexadecanoyl, 3-pentadecanoyloxyhexadecanoyl, 3-hexadecanoyloxyhexadecanoyl, 3-heptadecanoyloxyhexadecanoyl, 3-octadecanoyloxyhexadecanoyl, 3-nonadecanoyloxyhexadecanoyl, 3-eicosanoyloxyhexadecanoyl, 3-docosanoyloxyhexadecanoyl, 3-heneicosanoyloxyhexadecanoyl, 3-tricosanoyloxyhexadecanoyl, 3-tetracosanoyloxyhexadecanoyl, 2- dodecyltetradecanoyl, 2-tridecyltetradecanoyl, 2-tetradecyltetradecanoyl, 2-pentadecyltetradecanoyl, 2-hexadecyltetradecanoyl, 2-heptadecyltetradecanoyl, 2-octadecyltetradecanoyl, 2-tetradecylpentadecanoyl, 2-pentadecylpentadecanoyl, 2-hexadecylpentadecanoyl, 2-heptadecylpentadecanoyl, 2-octadecylpentadecanoyl, 2-dodecylhexadecanoyl, 2-tridecylhexadecanoyl, 2-tetradecylhexadecanoyl, 2-pentadecylhexadecanoyl, 2-hexadecylhexadecanoyl, 2-heptadecylhexadecanoyl, 2-octadecylhexadecanoyl, 2-dodecylpentadecanoyl, 2-tridecylpentadecanoyl, 2-tetradecylpentadecanoyl, 2-pentadecylpentadecanoyl, 2-hexadecylpentadecanoyl, 2-heptadecylpentadecanoyl, 2-octadecylpentadecanoyl, 2-dodecylhexadecanoyl, 2-tridecylhexadecanoyl, 2-tetradecylhexadecanoyl, 2-pentadecylhexadecanoyl, 2-hexadecylhexadecanoyl, 2-heptadecylhexadecanoyl, 2-octadecylhexadecanoyl, 2-dodecylheptadecanoyl, 2-tridecylheptadecanoyl, 2-tetradecylheptadecanoyl, 2-pentadecylheptadecanoyl, 2-hexadecylheptadecanoyl, 2-octadecylheptadecanoyl, 2-dodecyloctadecanoyl, 2-tridecyloctadecanoyol, 2-tetradecyloctadecanoyl, 2-pentadecyloctadecanoyl, 2-hexadecyloctadecanoyl, 2-heptadecyloctadecanoyl, 2-octadecyloctadecanoyl, 2-dodecylnonadecanoyl, 2-tridecylnonadecanoyl, 2-tetradecylnonadecanoyl, 2-pentadecylnonadecanoyl, 2-hexadecylnonadecanoyl, 2-heptadecylnonadecanoyl, 2-octadecylnonadecanoyl, 2-dodecyleicosanoyl, 2-tridecyleicosanoyl, 2-tetradecyleicosanoyl, 2-pentadecyleicosanoyl, 2-hexadecyleicosanoyl, 2-heptadecyleicosanoyl and 2-octadecyleicosanoyl groups.

Preferred groups of R3 are 3-tetradecanoyloxytetradecanoyl, 3-hexadecanoyloxytetradecanoyl, 3-octadecanoyloxytetradecanoyl, 3-tetracosanoyloxytetradecanoyl and 2-tetradecylhexadecanoyl groups.

Examples of R2 include hydrogen atom, decanoyl, undecanoyl, dodecanoyl, tridecanoyl, tetradecanoyl, pentadecanoyl, hexadecanoyl, heptadecanoyl, octadecanoyl, nonadecanoyl, eicosanoyl, docosanoyl, heneicosanoyl, tricosanoyl and tetracosanoyl groups.

R2 is preferably hydrogen atom or tetradecanoyl group.

Preferably, "Ala" is an L-alanine residue, and "isoGln" is a residue derivated from D-isoglutamine.

The compounds of the formula (I) of the present invention are basically muramyl dipeptide derivatives, in which the muramyl dipeptide moiety has preferably the same steric configuration as that of the muramyl dipeptide moiety in natural muramyl dipeptides. Namely, the moieties of muraminic acid and dipeptide in the present muramyl dipeptides have D-steric configuration and L-alanine-D-isoglutamine configuration, respectively. However, the muramyl dipeptides of the present invention may be those having other possible steric configurations.

The group —OR3 or —SR3 in the definition of the formula (I) preferably combines with the saccharide moiety in the form of α-bond and β-bond, respectively.

The acyloxyacyl group in R3 has an asymmetric carbon atom and may be in the form of D- or L-isomer, or racemic mixture.

Interesting compounds belonging to the formula (I) in the present invention include:

N-[2-0-{2-Acetamido-2,3-dideoxy-1-0-(2-tetradecylhexadecanoyl)-60 -D-glucopyranos-3-yl}-D-lactoyl]-L-alanyl-D-isoglutamine methylester N-[2-0-{2-Acetamido-2,3-dideoxy-6-0-decanoyl-1-0-(2-tetradecylhexadecanoyl)-α-D-glucopyranos-3-yl)-D-lactoyl]-L-alanyl-D-isoglutamine methylester N-[2-0-{2-Acetamido-2,3-dideoxy-6-0-tetradecanoyl-1-0-[2-tetradecylhexadecanoyl)-α-D-glucopyranos-3-yl}-D-lactoyl]-L-alanyl-D-isoglutamine methylester N-[2-0-{2-Acetamido-2,3-dideoxy-6-0-octadecanoyl-1-0-(2-tetradecylhexadecanoyl)-α-D-glucopyranos-3-yl}-D-lactoyl]-L-alanyl-D-isoglutamine methylester N-[2-0-{2-Acetamido-2,3-dideoxy-1-S-(2-tetradecylhexadecanoyl)-1-thio-β-D-glucopyranos-3-yl)-D-lactoyl]-L-alanyl-D-isoglutamine methylester N-[2-0-(2-Acetamido-2,3-dideoxy-6-0-decanoyl-1-S-(2-tetradecylhexadecanoyl)-1-thio-β-D-glucopyranos-3-yl}-D-lactoyl]-L-alanyl-D-isoglutamine methylester N-[2-0-{2-Acetamido-2,3-dideoxy-6-0-tetradecanoyl-1-1-S-(2-tetradecylhexadecanoyl)-1-thio-β-D-glucopyranos-3-yl}-D-lactoyl]-L-alanyl-D-isoglutamine methylester N-[2-0-{2-Acetamido-2,3-dideoxy-6-0-octadecanoyl-1-S-(2-tetradecylhexadecanoyl)-1-thio-β-D-glucopyranos-3-yl)-D-lactoyl]-L-alanyl-D-isoglutamine methylester N-[2-0-{2-Acetamido-2,3-dideoxy-1-0-{(3R)-3-tetradecanoyloxytetradecanoyl)-α-D-glucopyranos-3-yl}-D-lactoyl]-L-alanyl-D-isoglutamine methylester N-[2-0-{2-Acetamido-2,3-dideoxy-6-0-decanoyl-1-0-((3R)-3-tetradecanolyloxytetradecanoyl)-α-D-glucopyranos-3-yl}-D-lactoyl]-L-alanyl-D-isoglutamine methylester N-[2-0-{2-Acetamido-2,3-dideoxy-6-0-tetradecanoyl-1-0-((3R)-3-tetradecanoyloxytetradecanoyl)-α-D-glucopyranos-3-yl)-D-lactoyl]-L-alanyl-D-isoglutamine methylester N-[2-0-{2-Acetamido-2,3-dideoxy-6-0-octadecanoyl-1-0-((3R)-3-tetradecanoyloxytetradecanoyl)-α-D-glucopyranos-3-yl}-D-lactoyl]-L-alanyl-D-isoglutamine methylester N-[2-0-{2-Acetamido-2,3-dideoxy-1-S-([3R)-3-tetradecanoyloxytetradecanoyl)-1-thio-β-D-glucopyranos-3-yl}-D-lactoyl]-L-alanyl-D-isoglutamine methylester N-[2-0-{2-Acetamido-2,3-dideoxy-6-0-decanoyl-1-S-((3R)-3-tetradecanoyloxytetradecanoyl)-1-thio-β-D-glucopyranos-3-yl}-D-lactoyl]-L-alanyl-D-isoglutamine methylester N-[2-0-{2-Acetamido-2,3-dideoxy-6-0-tetradecanoyl-1-S-([3R)-3-tetradecanoyloxytetradecanoyl)-1-thio-β-D-glucopyranos-3-yl}-D-lactoyl]-L-alanyl-D-isoglutamine methylester N-[2-0-{2-Acetamido-2,3-dideoxy-6-0-octadecanoyl-1-S-((3R)-3-tetradecanoyloxytetradecanoyl)-1-thio-β-D-glucopyranos-3-yl}-D-lactoyl]-L-alanyl-D-isoglutamine methylester N-[2-0-{2-Acetamido-2,3-dideoxy-1-0-((3R)-3-hexadecanoyloxytetradecanoyl)-α-D-glucopyranos-3-yl}-D-lactoyl]-L-alanyl-D-isoglutamine methylester N-[2-0-{2-Acetamido-2,3-dideoxy-6-0-decanoyl-1-0-((3R)-3-hexadecanoyloxytetradecanoyl)-α-D-glucopyranos-3-yl)-D-lactoyl]-L-alanyl-D-isoglutamine methylester N-[2-0-{2-Acetamido-2,3-dideoxy-1-0-((3R)-3-hexadecanoyloxytetradecanoyl-6-0-tetradecanoyl-α-D-glucopyranos-3-yl}-D-lactoyl]-L-alanyl-D-isoglutamine methylester N-[2-0-{2-Acetamido-2,3-dideoxy-1-0-((3R)-3-hexadecanoyloxytetradecanoyl)-6-0-octadecanoyl-α-D- glucopyranos-3-yl}-D-lactoyl]-L-alanyl-D-isoglutamine methylester

N-[2-0-{2-Acetamido-2,3-dideoxy-1-S-((3R)-3-hexadecanoyloxytetradecanoyl)-1-thio-ß-D-glucopyranos-3-yl}-D-lactoyl]-L-alanyl-D-isoglutamine methylester N-[2-0-{2-Acetamido-2,3-dideoxy-6-0-decanoyl-1-S-((3R)-3-hexadecanoyloxytetradecanoyl)-1-thio-ß-D-glucopyranos-3-yl}-D-lactoyl]-L-alanyl-D-isoglutamine methylester N-[2-0-{2-Acetamido-2,3-dideoxy-1-S-((3R)-3-hexadecanoyloxytetradecanoyl)-6-0-tetradecanoyl-1-thio-ß-D-glucopyranos-3-yl}-D-lactoyl]-L-alanyl-D-isoglutamine methylester N-[2-0-{2-Acetamido-2,3-dideoxy-1-S-{(3R)-3-hexadecanoyloxytetradecanoyl)-6-0-octadecanoyl-1-thio-ß-D-glucopyranos-3-yl}-D-lactoyl]L-alanyl-D-isoglutamine methylester N-[2-0-{2-Acetamido-2,3-dideoxy-1-0-((3R)-3-octadecanoyloxytetradecanoyl)-α-D-glucopyranos-3-yl)-D-lactoyl]-L-alanyl-D-isoglutamine methylester N-[2-0-{2-Acetamido-2,3-dideoxy-6-0-decanoyl-1-0-((3R)-3-hexadecanoyloxytetradecanoyl}-α-D-glucopyranos-3-yl}-D-lactoyl]-L-alanyl-D-isoglutamine methylester N-[2-0-{2-Acetamido-2,3-dideoxy-1-0-((3R)-3-octadecanoyloxytetradecanoyl)-6-0-tetradecanoyl-α-D-glucopyranos-3-yl}-D-lactoyl]-L-alanyl-D-isoglutamine methylester N-[2-0-{2-Acetamido-2,3-dideoxy-6-0-octadecanoyl-1-0-((3R)-3-octadecanoyloxytetradecanoyl)-α-D-glucopyranos-3-yl}-D-lactoyl]-L-alanyl-D-isoglutamine methylester N-[2-0-{2-Acetamido-2,3-dideoxy-1-S-((3R)-3-octadecanoyloxytetradecanoyl)-1-thio-ß-D-glucopyranos-3-yl}-D-lactoyl]-L-alanyl-D-isoglutamine methylester N-[2-0-{2-Acetamido-2,3-dideoxy-6-0-decanoyl-1-S-((3R)-3-octadecanoyloxytetradecanoyl)-1-thio-ß-D-glucopyranos-3-yl}-D-lactoyl]-L-alanyl-D-isoglutamine methylester N-[2-0-{2-Acetamido-2,3-dideoxy-1-S-((3R)-3-octadecanoyloxytetradecanoyl)-6-0-tetradecanoyl-1-thio-ß-D-glucopyranos-3-yl}-D-lactoyl]-L-alanyl-D-isoglutamine methylester N-[2-0-{2-Acetamido-2,3-dideoxy-6-0-octadecanoyl1-S-((3R)-3-octadecanoyloxytetradecanoyl)-1-thio-ß-D-glucopyranos-3-yl}-D-lactoyl]-L-alanyl-D-isoglutamine methylester N-[2-0-{2-Acetamido-2,3-dideoxy-1-0-((3R)-3-tetracosanoyloxytetradecanoyl)-α-D-glucopyranos-3-yl}-D-lactoyl]-L-alanyl-D-isoglutamine methylester N-[2-0-{2-Acetamido-2,3-dideoxy-6-0-decanoyl-1-0-((3R)-3-tetracosanoyloxytetradecanoyl)-α-D-glucopyranos-3-yl}-D-lactoyl]-L-alanyl-D-isoglutamine methylester N-[2-0-{2-Acetamido-2,3-dideoxy-1-0-({3R)-3-tetracosanoyloxytetradecanoyl)-6-0-tetradecanoyl-α-D-glucopyranos-3-yl}-D-lactoyl]-L-alanyl-D-isoglutamine methylester N-[2-0-{2-Acetamido-2,3-dideoxy-6-0-octadecanoyl-1-0-((3R)-3-tetracosanoyloxytetradecanoyl}-α-D-glucopyranos-3-yl}-D-lactoyl]-L-alanyl-D-isoglutamine methylester N-[2-0-{2-Acetamido-2,3-dideoxy-1-S-((3R)-3-tetracosanoyloxytetradecanoyl)-1-thio-ß-D-glucopyranos-3-yl}-D-lactoyl]-L-alanyl-D-isoglutamine methylester N-[2-0-{2-Acetamido-2,3-dideoxy-6-0-decanoyl-1-S-((3R)-tetracosanoyloxytetradecanoyl)-1-thio-ß-D-glucopyranos-3-yl}-D-lactoyl]-L-alanyl-D-isoglutamine methylester N-[2-0-{2-Acetamido-2,3-dideoxy-1-S-((3R)-3-tetracosanoyloxytetradecanoyl)-6-0-tetradecanoyl-1-thio-ß-D-glucopyranos-3-yl}-D-lactoyl]-L-alanyl-D-isoglutamine methylester N-[2-0-{2-Acetamido-2,3-dideoxy-6-0-octadecanoyl-1-S-((3R)-3-tetracosanoyloxytetradecanoyl)-1-thio-ß-D-glucopyranos-3-yl)-D-lactoyl]-L-alanyl-D-isoglutamine methylester N-[2-0-{2-Acetamido-2,3-dideoxy-6-0-dodecanoyl-1-0-(2-tetradecylhexadecanoyl)-α-D-glucopyranos-3-yl}-d-lactoyl]-L-alanyl-D-isoglutamine methylester N-[2-0-{2-Acetamido-2,3-dideoxy-6-0-hexadecanoyl-1-0-(2-tetradecylhexadecanoyl)-α-D-glucopyranos-3-yl}-D-lactoyl]-L-alanyl-D-isoglutamine methylester N-[2-0-(2-Acetamido-2,3-dideoxy-6-0-dodecanoyl-1-S-(2-tetradecylhexadecanoyl)-1-thio-ß-D-glucopyranos-3-yl)-D-lactoyl]-L-alanyl-D-isoglutamine methyester N-[2-0-(2-Acetamido-2,3-dideoxy-6-0-hyxadecanoyl-1-S-(2-tetradecylhexadecanoyl)-1-thio-ß-D-glucopyranos-3-yl}-D-lactoyl]-L-alanyl-D-isoglutamine methyester N-[2-0-{2-Acetamido-2,3-dideoxy-1-0-((3R)-3-dodecanoyloxytetradecanoyl)-α-D-glucopyranos-3-yl}-D-lactoyl]-L-alanyl-D-isoglutamine methylester N-[2-0-{2-Acetamido-2,3-dideoxy-6-0-decanoyl-1-0-((3R)-3-dodecanoyloxytetradecanoyl)-α-D-glucopyranos-3-yl}-D-lactoyl]-L-alanyl-D-isoglutamine methylester N-[2-0-{2-Acetamido-2,3-dideoxy-6-0-dodecanoyl-1-0-((3R)-dodecanoyloxytetradecanoyl)-α-D-glucopyranos-3-yl}-D-lactoyl]-L-alanyl-D-isoglutamine methylester N-[2-0-{2-Acetamido-2,3-dideoxy-1-0-((3R)-3-dodecanoyloxytetradecanoyl)-6-0-tetradecanoyl-α-D-glucopyranos-3-yl}-D-lactoyl]-L-alanyl-D-isoglutamine methylester N-[2-0-{2-Acetamido-2,3-dideoxy-1-0-((3R)-3-dodecanoyloxytetradecanoyl)-6-0-hexadecanoyl-α-D-glucopyranos-3-yl}-D-lactoyl]-L-alanyl-D-isoglutamine methylester N-[2-0-{2-Acetamido-2,3-dideoxy-1-0-((3R)-3-dodecanoyloxytetradecanoyl)-6-0-octadecanoyl-α-D-glucopyranos-3-yl}-D-lactoyl]-L-alanyl-D-isoglutamine methylester N-[2-0-{2-Acetamido-2,3-dideoxy-1-S-((3R)-3-dodecanoyloxytetradecanoyl)-1-thio-ß-D-glucopyranos-3-yl)-D-lactoyl]-L-alanyl-D-isoglutamine methylester N-[2-0-{2-Acetamido-2,3-dideoxy-6-0-decanoyl-1-S-((3R)-3-dodecanoyloxytetradecanoyl)-1-thio-ß-D-glucopyranos-3-yl)-D-lactoyl]-L-alanyl-D-isoglutamine methylester N-[2-0-{2-Acetamido-2,3-dideoxy-6-0-dodecanoyl-1-S-((3R)-3-dodecanoyloxytetradecanoyl)-1-thio-8-D-glucopyranos-3-yl}-D-lactoyl]-L-alanyl-D-isoglutamine methylester N-[2-0-{2-Acetamido-2,3-dideoxy-1-S-((3R)-3-dodecanoyloxytetradecanoyl)-6-0-tetradecanoyl-1-thio-ß-D-glucopyranos-3-yl}-D-lactoyl]-L-alanyl-D-isoglutamine methylester N-[2-0-{2-Acetamido-2,3-dideoxy-1-S-((3R)-3-dodecanoyloxytetradecanoyl)-6-0-hexadecanoyl-1-thio-β-D-glucopyranos-3-yl}-D-lactoyl]-L-alanyl-D-isoglutamine methylester N-[2-0-{2-Acetamido-2,3-dideoxy-1-S-(3R)-3-dodecanoyloxytetradecanoyl-6-0-octadecanoyl-1-thio-β-D-glucopyranos-3-yl}-D-lactoyl]-L-alanyl-D-isoglutamine methylester N-[2-0-{2-Acetamido-2,3-dideoxy-6-0-dodecanoyl-1-0-dodecanoyl-1-0-((3R)-3-tetradecanoyloxytetradecanoyl-α-D-glucopyranos-3-yl}-D-lactoyl]-L-alanyl-D-isoglutamine methylester N-[2-0-{2-Acetamido-2,3-dideoxy-6-0-hexadecanoyl-1-0-((3R)-3-tetradecanoyloxytetradecanoyl)-α-D-glucopyranos-3-yl}-D-lactoyl]-L-alanyl-D-isoglutamine methylester N-[2-0-{2-Acetamido-2,3-dideoxy-6-0-dodecanoyl-1-S-((3R)-3-tetradecanoyloxytetradecanoyl)-1-thio-β-D-glucopyranos-3-yl}-D-lactoyl]-L-alanyl-D-isoglutamine methylester N-[2-0-{2-Acetamido-2,3-dideoxy-6-0-hexadecanoyl-1-S-((3R)-3-tetradecanoyloxytetradecanoyl)-1-thio-β-D-glucopyranos-3-yl)-D-lactoyl]-L-alanyl-D-isoglutamine methylester N-[2-0-{2-Acetamido-2,3-dideoxy-6-0-dodecanoyl-1 0-((3R)-3-hexadecanoyloxytetradecanoyl)-o-D-glucopyranos-3-yl}-D-lactoyl]-L-alanyl-D-isoglutamine methylester N-[2-0-{2-Acetamido-2,3-dideoxy-6-0-hexadecanoyl-1-0-((3R)-3-hexadecanoyloxytetradecanoyl)-α-D-glucopyranos-3-yl)-D-lactoyl]-L-alanyl-D-isoglutamine methylester N-[2-0-{2-Acetamido-2,3-dideoxy-6-0-dodecanoyl-1-S-((3R)-3-hexadecanoyloxytetradecanoyl)-1-thio-β-D-glucopyranos-3-yl)-D-lactoyl]-L-alanyl-D-isoglutamine methylester N-[2-0-{2-Acetamido-2,3-dideoxy-6-0-hexadecanoyl-1-S-((3R)-3-hexadecanoyloxytetradecanoyl)-1-thio-β-D-glucopyranos-3-yl}-D-lactoyl]-L-alanyl-D-isoglutamine methylester N-[2-0-{2-Acetamido-2,3-dideoxy-6-0-dodecanoyl-1-0-((3R)-3-hexadecanoyloxytetradecanoyl)-α-D-glucopyranos-3-yl}-D-lactoyl]-L-alanyl-D-isoglutamine methylester N-[2-0-{2-Acetamido-2,3-dideoxy-6-0-hexadecanoyl-1-0-((3R)-3-octadecanoyloxytetradecanoyl)-α-D-glucopyranos-3-yl}-D-lactoyl]-L-alanyl-D-isoglutamine methylester N-[2-0-{2-Acetamido-2,3-dideoxy-6-0-dodecanoyl-1-S-((3R)-3-octadecanoyloxytetradecanoyl)-1-thio-β-D-glucopyranos-3-yl}-D-lactoyl]-L-alanyl-D-isoglutamine methylester N-[2-0-{2-Acetamido-2,3-dideoxy-6-0-hexadecanoyl-1-S-((3R)-3-octadecanoyloxytetradecanoyl)-1-thio-β-D-glucopyranos-3-yl)-D-lactoyl]-L-alanyl-D-isoglutamine methylester N-[2-0-{2-Acetamido-2,3-dideoxy-1-0-((3R)-3-eicosanoyloxytetradecanoyl}-α-D-glucopyranos-3-yl}-D-lactoyl]- L-alanyl-D-isoglutamine methylester N-[2-0-{2-Acetamido-2,3-dideoxy-6-0-decanoyl-1-0-((3R)-3-eicosanoyloxytetradecanoyl)-α-D-glucopyranos-3-yl}-D-lactoyl]-L-alanyl-D-isoglutamine methylester N-[2-0-{2-Acetamido-2,3-dideoxy-6-0-dodecanoyl-1-0-((3R)-3-eicosanoyloxytetradecanoyl)-α-D-glucopyranos-3-yl}-D-lactoyl]-L-alanyl-D-isoglutamine methylester N-[2-0-{2-Acetamido-2,3-dideoxy-1-0-((3R)-3-eeicosanoyloxytetradecanoyl}-6-0-tetradecanoyl-α-D-glucopyranos-3-yl}-D-lactoyl]-L-alanyl-D-isoglutamine methylester N-[2-0-{2-Acetamido-2,3-dideoxy-1-0-((3R)-3-eicosanoyloxytetradecanoyl)-6-0-hexadecanoyl-α-D-glucopyranos-3-yl)-D-lactoyl]-L-alanyl-D-isoglutamine methylester N-[2-0-{2-Acetamido-2,3-dideoxy-1-0-((3R)-3-eicosanoyloxytetrdecanoyl)-6-0-octadecanoyl-α-D-glucopyranos-3-yl)-D-lactoyl]-L-alanyl-D-isoglutamine methylester N-[2-0-{2-Acetamido-2,3-dideoxy-1-S-([3R)-3-eicosanoyloxytetradecanoyl)-1-thio-β-D-glucopyranos-3-yl))-D-lactoyl]-L-alanyl-D-isoglutamine methylester N-[2-0-{2-Acetamido-2,3-dideoxy-6-0-decanoyl-1-S-((3R)-3-eicosanoyloxytetradecanoyl)-1-thio-β-D-glucopyranos-3-yl}-D-lactoyl]-L-alanyl-D-isoglutamine methylester N-[2-0-{2-Acetamido-2,3-dideoxy-6-0-decanoyl-1-S-((3R)-3-eicosanoyloxytetradecanoyl)-1-thio-β-D-glucopyranos-3-yl}-D-lactoyl]-L-alanyl-D-isoglutamine methylester N-[2-0-{2-Acetamido-2,3-dideoxy-1-S-((3R)-3-eicosanoyloxytetradecanoyl)-6-0-tetradecanoyl1-thio-β-D-glucopyranos-3-yl}-D-lactoyl]-L-alanyl-D-isoglutamine methylester N-[2-0-{2-Acetamido-2,3-dideoxy-1-S-({3R)-3-eicosanoyloxytetradecanoyl)-6-0-hexadecanoyl-1-thio-β-D-glucopyranos-3-yl}-D-lactoyl]-L-alanyl-D-isoglutamine methylester N-[2-0-{2-Acetamido-2,3-dideoxy-1-S-((3R)-3-eicosanoyloxytetradecanoyl)-6-0-octadecanoyl-1-thio-β-D-glucopyranos-3-yl}-D-lactoyl]-L-alanyl-D-isoglutamine methylester N-[2-0-{2-Acetamido-2,3-dideoxy-1-0-((3R)-3-docosanoyloxytetradecanoyl)-α-D-glucopyranos-3-yl}-D-1-actoyl]-L-alanyl-D-isoglutamine methylester N-[2-0-{2-Acetamido-2,3-dideoxy-6-0-decanoyl-1-0-((3R)-3-docosanoyloxytetradecanoyl)-α-D-glucopyranos-3-yl}-D-lactoyl]-L-alanyl---isoglutamine methylester N-[2-0-{2-Acetamido-2,3-dideoxy-1-0-((3R)-3-docosanoyloxytetradecanoyl)-6-0-decanoyl-α-D-glucopyranos-3-yl)-D-lactoyl]-L-alanyl-D-isoglutamine methylester N-[2-0-{2-Acetamido-2,3-dideoxy-1-0-((3R)-3-docosanoyloxytetradecanoyl)-6-0-tetradecanoyl-α-D-glucopyranos-3-yl}-D-lactoyl]-L-alanyl-D-isoglutamine methylester N-[2-0-{2-Acetamido-2,3-dideoxy-1-0-((3R)-3-docosanoyloxytetradecanoyl-6-0-hexadecanoyl-α-D-glucopyranos-3-yl}-D-lactoyl]-L-alanyl-D-isoglutamine methylester N-[2-0-{2-Acetamido-2,3-dideoxy-1-0-((3R)-3-docosanoyloxytetradecanoyl)-6-0-octadecanoyl-α-D-glucopyranos-3-yl)-D-lactoyl]-L-alanyl-D-isoglutamine methylester N-[2-0-{2-Acetamido-2,3-dideoxy-1-S-((3R)-3-docosanoyloxytetradecanoyl)-1-thio-β-D-glucopyranos-yl}-D-lactoyl]-L-alanyl-D-isoglutamine methylester N-[2-0-{2-Acetamido-2,3-dideoxy-1-S-((3R)-3-docosanoyloxytetradecanoyl)-1-thio-β-D-glucopyranos-3-yl}-D-lactoyl]-L-alanyl-D-isoglutamine methylester N-[2-0-{2-Acetamido-2,3-dideoxy-1-S-((3R)-3-docosanoyloxytetradecanoyl)-6-0-dodecanoyl-1-thio-β-D-glucopyranos-3-yl)-D-lactoyl]-L-alanyl-D-isoglutamine methylester N-[2-0-{2-Acetamido-2,3-dideoxy-1-S-((3R)-3-docosanoyloxytetradecanoyl)-6-0-tetradecanoyl-1-thio-β-D-glucopyranos-3-yl}-D-lactoyl]-L-alanyl-D-isoglutamine methylester N-[2-0-{2-Acetamido-2,3-dideoxy-1-S-((3R)-3-docosanoyloxytetradecanoyl)-6-0-hexadecanoyl-1-thio-β-D-glucopyranos-3-yl)-D-lactoyl]-L-alanyl-D-isoglutamine methylester N-[2-0-{2-Acetamido-2,3-dideoxy-1-S-((3R)-3-docosanoyloxytetradecanoyl)-6-0-octadecanoyl-1-thio-β-D-glucopyranos-3-yl)-D-lactoyl]-L-alanyl-D-isoglutamine methylester N-[2-0-{2-Acetamido-2,3-dideoxy-6-0-dodecanoyl-1-0-((3R)-3-tetracosanoyloxytetradecaoyl)-α-D-glucopyranos-3-yl}-D-lactoyl]-L-alanyl-D-isoglutamine methylester N-[2-0-{2-Acetamido-2,3-dideoxy-6-0-hexadecanoyl-1-0-((3R)-3-tetracosanoyloxytetradecanoyl)-α-D-glucopyranos-3-yl}-D-lactoyl]-L-alanyl-D-isoglutamine methylester N-[2-0-{2-Acetamido-2,3-dideoxy-6-0-dodecanoyl-1-S-{(3R)-3-tetracosanoyloxytetradecanoyl)-1-thio-β-D-glucopyranos-3-yl)-D-lactoyl]-L-alanyl-D-isoglutamine methylester N-[2-0-{2-Acetamido-2,3-dideoxy-6-0-hexadecanoyl-1-S-((3R)-3-tetracosanoyloxytetradecanoyl)-1-thio-β-D-glucopyranos-3-yl}-D-lactoyl]-L-alanyl-D-isoglutamine methylester N-[2-0-{2-Acetamido-2,3-dideoxy-1-0-{2-dodecyltetradecanoyl)-α-D-glucopyranos-3-yl)-D-lactoyl]-L-alanyl-D-isoglutamine methylester N-[2-0-{2-Acetamido-2,3-dideoxy-6-0-decanoyl-1-0-(2-dodecyltetradecanoyl)-α-D-glucopyranos-3-yl}-D-lactoyl]-L-alanyl-D-isoglutamine methylester N-[2-0-{2-Acetamido-2,3-dideoxy-6-0-dodecanoyl-1-0-(2-dodecyltetradecanoyl)-α-D-glucopyranos-3-yl}-D-lactoyl]-L-alanyl-D-isoglutamine methylester N-[2-0-{2-Acetamido-2,3-dideoxy-1-0-[2-dodecyl-tetradecanoyl)-6-0-tetradecanoyl-α-D-glucopyranos-3-yl}-D-lactoyl]-L-alanyl-D-isoglutamine methylester N-[2-0-{2-Acetamido-2,3-dideoxy-1-0-[2-dodecyltetradecanoyl)-6-0-hexadecanoyl-α-D-glucopyranos-3-yl}-D-lactoyl]-L-alanyl-D-isoglutamine methylester N-[2-0-{2-Acetamido-2,3-dideoxy-1-0-(2-dodecyltetradecanoyl)-6-0-octadecanoyl-β-D-glucopyranos-3-yl}-D-lactoyl]-L-alanyl-D-isoglutamine methylester N-[2-0-{2-Acetamido-2,3-dideoxy-1-S-(2-dodecyltetradecanoyl)-1-thio-β-D-glucopyranos-3-yl}-D-lactoyl]-L-alanyl-D-isoglutamine methylester N-[2-0-{2-Acetamido-2,3-dideoxy-6-0-decanoyl-1-S-(2-dodecyltetradecanoyl)-1-thio-β-D-glucopyranos-3-yl}-D-lactoyl]-L-alanyl-D-isoglutamine methylester N-[2-0-{2-Acetamido-2,3-dideoxy-6-0-dodecanoyl-1-S-(2-dodecyltetradecanoyl)-1-thio-β-D-glucopyranos-3-yl}-D-lactoyl]-L-alanyl-D-isoglutamine methylester N-[2-0-{2-Acetamido-2,3-dideoxy-1-S-(2-dodecyl-tetradecanoyl)-6-0-tetradecanoyl-1-thio-β-D-glucopyranos-3-yl)-D-lactoyl]-L-alanyl-D-isoglutamine methylester N-[2-0-{2-Acetamido-2,3-dideoxy-1-S-(2-dodecyltetradecanoyl)-6-0-hexadecanoyl-1-thio-β-D-glucopyranos-3-yl)-D-lactoyl]-L-alanyl-D-isoglutamine methylester N-[2-0-{2-Acetamido-2,3-dideoxy-1-S-[2-dodecyltetradecanoyl)-6-0-octadecanoyl-1-thio-β-D-glucopyranos-3-yl}-D-lactoyl]-L-alanyl-D-isoglutamine methylester N-[2-0-{2-Acetamido-2,3-dideoxy-1-0-(2-hexadecyloctadecanoyl)-α-D-glucopyranos-3-yl}-D-lactoyl]-L-alanyl-D-isoglutamine methylester N-[2-0-{2-Acetamido-2,3-dideoxy-6-0-decanoyl-1-0-2-hexadecyloctadecanoyl)-α-D-glucopyranos-3-yl}-D-lactoyl]-L-alanyl-D-isoglutamine methylester N-[2-0-(2-Acetamido-2,3-dideoxy-6-0-dodecanoyl-1-0-(2-hexadecyloctadecanoyl)-α-D-glucopyranos-3-yl}-D-lactoyl]-L-alanyl-D-isoglutamine methylester N-[2-0-{2-Acetamido-2,3-dideoxy-1-0-(2-hexadecyloctadecanoyl)-6-0-tetradecanoyl-α-D-glucopyranos-3-yl}-D-lactoyl]-L-alanyl-D-isoglutamine methylester N-[2-0-{2-Acetamido-2,3-dideoxy-6-0-hexadecanoyl-1-0-[2-hexadecyloctadecanoyl)-α-D-glucopyranos-3-yl}-D-lactoyl]-L-alanyl-D-isoglutamine methylester N-[2-0-{2-Acetamido-2,3-dideoxy-1-0-(2-hexadecyloctadecanoyl)-6-0-octadecanoyl-α-D-glucopyranos-3-yl)-D-lactoyl]-L-alanyl-D-isoglutamine methylester N-[2-0-{2-Acetamido-2,3-dideoxy-1-S-(2-hexadecyloctadecanoyl)-1-thio-β-D-glucopyranos-3-yl}-D-lactoyl]-L-alanyl-D-isoglutamine methylester N-[2-0-{2-Acetamido-2,3-dideoxy-6-0-decanoyl-1-S-(2-hexadecyloctadecanoyl)-1-thio-β-D-glucopyranos-3-yl}-D-lactoyl]-L-alanyl-D-isoglutamine methylester N-[2-0-{2-Acetamido-2,3-dideoxy-6-0-dodecanoyl-1-S-(2-hexadecyloctadecanoyl)-1-thio-β-D-glucopyranos-3-yl}-D-lactoyl]-L-alanyl-D-isoglutamine methylester N-[2-0-{2-Acetamido-2,3-dideoxy-1-S-(2-hexadecyl-octadecanoyl)-6-0-tetradecanoyl-1-thio-8-D-glucopyranos-3-yl}-D-lactoyl]-L-alanyl-D-isoglutamine methylester N-[2-0-{2-Acetamido-2,3-dideoxy-6-0-hexadecanoyl-1-S-(2-hexadecyloctadecanoyl)-1-thio-β-D-glucopyranos-3-yl}-D-lactoyl]-L-alanyl-D-isoglutamine methylester N-[2-0-{2-Acetamido-2,3-dideoxy-1-S-(2-hexadecyloctadecanoyl}-6-0-octadecanoyl-1-thio-β-D-glucopyranos-3-yl)-D-lactoyl]-L-alanyl-D-isoglutamine methylester N-[2-0-{2-Acetamido-2,3-dideoxy-1-0-(2-octadecyleicosanoyl)-α-D-glucopyranos-3-yl}-D-lactoyl]-L-alanyl-D-isoglutamine methylester N-[2-0-{2-Acetamido-2,3-dideoxy-6-0-decanoyl-1-0-(2-octadecyleisocanoyl)-α-D-glucopyranos-3-yl}-D-lactoyl]-L-alanyl-D-isoglutamine methylester N-[2-0-{2-Acetamido-2,3-dideoxy-6-0-dodecanoyl-1-0-(2-octadecyleicosanoyl)-α-D-glucopyranos-3-yl}-D-lactoyl]-L-alanyl-D-isoglutamine methylester N-[2-0-{2-Acetamido-2,3-dideoxy-1-0-(2-octadecyleicosanoyl)-6-0-tetradecanoyl-α-D-glucopyranos-3-yl}-D-lactoyl]-L-alanyl-D-isoglutamine methylester N-[2-0-{2-Acetamido-2,3-dideoxy-6-0-hexadecanoyl-1-0-(2-octadecyleicosanoyl)-α-D-glucopyranos-3-yl}-D-lactoyl]-L-alanyl-D-isoglutamine methylester N-[2-0-{2-Acetamido-2,3-dideoxy-6-0-octadecanoyl-1-0-(2-octadecyleicosanoyl)-α-D-glucopyranos-3-yl}-D-lactoyl]-L-alanyl-D-isoglutamine methylester N-[2-0-{2-Acetamido-2,3-dideoxy-1-S-(2-octadecyleicosanoyl)-1-thio-β-D-glucopyranos-3-yl}-D-lactoyl]-L-alanyl-D-isoglutamine methylester N-[2-O-{2-Acetamido-2,3-dideoxy-6-O-decanoyl-1-S-(2-octadecyleicosanoyl)-1-thio-β-D-glucopyranos-3-yl}-D-lactoyl]-L-alanyl-D-isoglutamine methylester N-[2-O-{2-Acetamido-2,3-dideoxy-6-O-dodecanoyl-1-S-[2-octadecyleicosanoyl)-1-thio-β-D-glucopyranos-3-yl}-D-lactoyl]-L-alanyl-D-isoglutamine methylester N-[2-O-{2-Acetamido-2,3-dideoxy-1-S-(2-octadecyleicosanoyl)-6-O-tetradecanoyl-1-thio-β-D-glucopyranos-3-yl}-D-lactoyl]-L-alanyl-D-isoglutamine methylester N-[2-O-{2-Acetamido-2,3-dideoxy-6-O-hexadecanoyl-1-S-(2-octadecyleicosanoyl)-1-thio-β-D-glucopyranos-3-yl}-D-lactoyl]-L-alanyl-D-isoglutamine methylester N-[2-O-{2-Acetamido-2,3-dideoxy-6-O-octadecanoyl-1-S-(2-octadecyleicosanoyl)-1-thio-β-D-glucopyranos-3-yl}-D-lactoyl]-L-alanyl-D-isoglutamine methylester N-[2-O-[2-Acetamido-2,3-dideoxy-1-O-(2-dodecylhexadecanoyl)-α-D-glucopyranos-3-yl}-D-lactoyl]-L-alanyl-D-isoglutamine methylester N-[2-O-{2-Acetamido-2,3-dideoxy-6-O-decanoyl-1-O-(2-dodecylhexadecanoyl)-α-D-glucopyranos-3-yl)-D-lactoyl]-L-alanyl-D-isoglutamine methylester .N-[2-O-{2-Acetamido-2,3-dideoxy-6-O-dodecanoyl-1-O-(2-dodecylhexadecanoyl)-α-D-glucopyranos-3-yl}-D-lactoyl]-L-alanyl-D-isoglutamine methylester N-[2-O-{2-Acetamido-2,3-dideoxy-1-O-(2-dodecylhexadecanoyl)-6-O-tetradecanoyl-α-D-glucopyranos-3-yl}-D-lactoyl]-L-alanyl-D-isoglutamine methylester N-[2-O-{2-Acetamido-2,3-dideoxy-1-O-(2-dodecylhexadecanoyl)-6-O-hexadecanoyl-α-D-glucopyranos-3-yl}-D-lactoyl]-L-alanyl-D-isoglutamine methylester N-[2-O-{2-Acetamido-2,3-dideoxy-1-O-(2-dodecylhexadecanoyl)-6-O-octadecanoyl-α-D-glucopyranos-3-yl)-D-lactoyl]-L-alanyl-D-isoglutamine methylester N-[2-O-{2-Acetamido-2,3-dideoxy-1-S-(2-dodecylhexadecanoyl)-1-thio-β-D-glucopyranos-3-yl}-D-lactoyl]-L-alanyl-D-isoglutamine methylester N-[2-O-{2-Acetamido-2,3-dideoxy-6-O-decanoyl-1-S-(2-dodecylhexadecanoyl)-1-thio-β-D-glucopyranos-3-yl}-D-lactoyl]-L-alanyl-D-isoglutamine methylester N-[2-O-{2-Acetamido-2,3-dideoxy-6-O-dodecanoyl-1-S-(2-dodecylhexadecanoyl)-1-thio-β-D-glucopyranos-3-yl}-D-lactoyl]-L-alanyl-D-isoglutamine methylester N-[2-O-{2-Acetamido-2,3-dideoxy-1-S-{2-dodecylhexadecanoyl)-6-O-tetradecanoyl-1-thio-β-D-glucopyranos-3-yl}-D-lactoyl]-L-alanyl-D-isoglutamine methylester N-[2-O-{2-Acetamido-2,3-dideoxy-1-S-(2-dodecylhexadecanoyl)-6-O-hexadecanoyl-1-thio-β-D-glucopyranos-3-yl}-D-lactoyl]-L-alanyl-D-isoglutamine methylester N-[2-O-{2-Acetamido-2,3-dideoxy-1-S-[2-dodecylhexadecanoyl)-6-O-octadecanoyl-1-thio-β-D-glucopyranos-3-yl}-D-lactoyl]-L-alanyl-D-isoglutamine methylester N-[2-O-{2-Acetamido-2,3-dideoxy-1-O-(2-dodecyloctadecanoyl)-α-D-glucopyranos-3-yl}-D-lactoyl]-L-alanyl-D-isoglutamine methylester N-[2-O-{2-Acetamido-2,3-dideoxy-6-O-decanoyl-1-O-(2-dodecyloctadecanoyl)-α-D-glucopyranos-3-yl}-D-lacto-yl]-L-alanyl-D-isoglutamine methylester N-[2-O-{2-Acetamido-2,3-dideoxy-6-O-dodecanoyl-1-O-(2-dodecyloctadecanoyl)-α-D-glucopyranos-3-yl}-D-lactoyl]-L-alanyl-D-isoglutamine methylester N-[2-O-{2-Acetamido-2,3-dideoxy-1-O-(2-dodecyloctadecanoyl)-6-O-tetradecanoyl-α-D-glucopyranos-3-yl}-D-lactoyl]-L-alanyl-D-isoglutamine methylester N-[2-O-{2-Acetamido-2,3-dideoxy-1-O-(2-dodecyloctadecanoyl)-6-O-hexadecanoyl-α-D-glucopyranos-3-yl}-D-lactoyl]-L-alanyl-D-isoglutamine methylester N-[2-O-{2-Acetamido-2,3-dideoxy-1-O-(2-dodecyloctadecanoyl)-6-O-octadecanoyl-α-D-glucopyranos-3-yl)-D-lactoyl]-L-alanyl-D-isoglutamine methylester N-[2-O-{2-Acetamido-2,3-dideoxy-1-S-(2-dodecyloctadecanoyl)-1-thio-β-D-glucopyranos-3-yl)-D-lactoyl]-L-alanyl-D-isoglutamine methylester N-[2-O-{2-Acetamido-2,3-dideoxy-6-O-decanoyl-1-S-(2-dodecyloctadecanoyl)-1-thio-β-D-glucopyranos-3-yl}-D-lactoyl]-L-alanyl-D-isoglutamine methylester N-[2-O-{2-Acetamido-2,3-dideoxy-6-O-dodecanoyl-1-S-(2-dodecyloctadecanoyl)-1-thio-β-D-glucopyranos-3-yl}-D-lactoyl]-L-alanyl-D-isoglutamine methylester N-[2-O-{2-Acetamido-2,3-dideoxy-1-S-(2-dodecyloctadecanoyl)-6-O-tetradecanoyl-1-thio-β-D-glucopyranos-3-yl}-D-lactoyl]-L-alanyl-D-isoglutamine methylester N-[2-O-{2-Acetamido-2,3-dideoxy-1-S-(2-dodecyloctadecanoyl)-6-O-hexadecanoyl-1-thio-β-D-glucopyranos-3-yl)-D-lactoyl]-L-alanyl-D-isoglutamine methylester N-[2-O-{2-Acetamido-2,3-dideoxy-1-S-(2-dodecyloctadecanoyl)-6-O-octadecanoyl-1-thio-8-D-glucopyranos-3-yl}-D-lactoyl]-L-alanyl-D-isoglutamine methylester N-[2-O-{2-Acetamido-2,3-dideoxy-1-O-(2-dodecyleicosanoyl)-α-D-glucopyranos-3-yl}-D-lactoyl]-L-alanyl-D-isoglutamine methylester N-[2-O-{2-Acetamido-2,3-dideoxy-6-O-decanoyl-1-O-(2-dodecyleicosanoyl)-α-D-glucopyranos-3-yl)-D-lactoyl]-L-alanyl- D-isoglutamine methylester N-[2-O-{2-Acetamido-2,3-dideoxy-6-O-dodecanoyl-1-O-(2-dodecyleicosanoyl)-α-D-glucopyranos-3-yl)-D-lactoyl]-L-alanyl-D-isoglutamine methylester N-[2-O-{2-Acetamido-2,3-dideoxy-1-O-(2-dodecyleicosanoyl)-6-O-tetradecnaoyl-α-D-glucopyranos-3-yl}-D-lactoyl]-L-alanyl-D-isoglutamine methylester N-[2-O-{2-Acetamido-2,3-dideoxy-1-O-(2-dodecyleicosanoyl)-6-O-hexadecanoyl-α-D-glucopyranos-3-yl}-D-lactoyl]-L-alanyl-D-isoglutamine methylester N-[2-O-{2-Acetamido-2,3-dideoxy-1-O-(2-dodecyleicosanoyl)-6-O-octadecanoyl)-α-D-glucopyranos-3-yl}-D-lactoyl]-L-alanyl-D-isoglutamine methylester N-[2-O-{2-Acetamido-2,3-dideoxy-1-S-(2-dodecyleicosanoyl)-1-thio-β-D-glucopyranos-3-yl}-D-lactoyl]-L-alanyl-D-isoglutamine methylester N-[2-O-{2-Acetamido-2,3-dideoxy-6-O-decanoyl-1-S-(2-dodecyleicosanoyl)-1-thio-β-D-glucopyranos-3-yl}-D-lactoyl]-L-alanyl-D-isoglutamine methylester N-[2-O-{2-Acetamido-2,3-dideoxy-6-O-dodecanoyl-1-S-(2-dodecyleicosanoyl)-1-thio-β-D-glucopyranos-3-yl}-D-lactoyl]-L-alanyl-D-isoglutamine methylester N-[2-O-{2-Acetamido-2,3-dideoxy-1-S-{2-dodecyleicosanoyl)-6-O-tetradecanoyl-1-thio-β-D-glucopyranos-3-yl}-D-lactoyl]-L-alanyl-D-isoglutamine methylester N-[2-O-{2-Acetamido-2,3-dideoxy-1-S-(2-dodecyeicosanoyl)-6-O-hexadecanoyl-1-thio-β-D-glucopyranos-3-yl)-D-lactoyl]-L-alanyl-D-isoglutamine methylester N-[2-0-{2-Acetamido-2,3-dideoxy-1-S-[2-dodecyleicosanoyl)-6-0-octadecanoyl-1-thio-β-D-glucopyranos-3-yl)-D-lactoyl]-L-alanyl-D-isoglutamine methylester N-[2-0-{2-Acetamido-2,3-dideoxy-1-0-((3R}-3-dodecanoyloxydodecanoyl)-α-D-glucopyranos-3-yl}-D-lactoyl]-L-alanyl-D-isoglutamine methylester N-[2-0-{2-Acetamido-2,3-dideoxy-6-0-docanoyl-1-0-((3R)-3-dodecanoyloxydodecanoyl)-α-D-glucopyranos-3-yl}-D-lactoyl]-L-alanyl-D-isoglutamine methylester N-[2-0-{2-Acetamido-2,3-dideoxy-6-0-dodecanoyl-1-0-((3R)-3-dodecanoyloxydodecanoyl)-α-D-glucopyranos-3-yl}-D-lactoyl]-L-alanyl-D-isoglutamine methylester N-[2-0-(2-Acetamido-2,3-dideoxy-1-0-((3R)-3-dodecanoyloxydodecanoyl)-6-0-tetradecanoyl-α-D-glucopyranos-3-yl}-D-lactoyl]-L-alanyl-D-isoglutamine methylester N-[2-0-{2-Acetamido-2,3-dideoxy-1-0-((3R)-3-dodecanoyloxydodecanoyl)-6-0-hexadecanoyl-α-D-glucopyranos-3-yl}-D-lactoyl]-L-alanyl-D-isoglutamine methylester N-[2-0-{2-Acetamido-2,3-dideoxy-1-0-((3R)-3-dodecanoyloxydodecanoyl)-6-0-octadecanoyl-α-D-glucopyranos-3-yl}-D-lactoyl]-L-alanyl-D-isoglutamine methylester N-[2-0-{2-Acetamido-2,3-dideoxy-1-S-((3R)-3-dodecanoyloxydodecanoyl)-1-thio-β-D-glucopyranos-3-yl}-D-lactoyl]-L-alanyl-D-isoglutamine methylester N-[2-0-{2-Acetamido-2,3-dideoxy-6-0-docanoyl-1-S-((3R)-3-dodecanoyloxydodecanoyl)-1-thio-β-D-glucopyranos-3-yl}-D-lactoyl]-L-alanyl-D-isoglutamine methylester N-[2-0-{2-Acetamido-2,3-dideoxy-6-0-dodecanoyl-1-S-((3R)-3-dodecanoyloxydodecanoyl)-1-thio-β-D-glucopyranos-3-yl}-D-lactoyl]-L-alanyl-D-isoglutamine methylester N-[2-0-{2-Acetamido-2,3-dideoxy-1-S-((3R)-3-dodecanoyloxydodecanoyl)-6-0-tetradecanoyl-1-thio-β-D-glucopyranos-3-yl}-D-lactoyl]-L-alanyl-D-isoglutamine methylester N-[2-0-{2-Acetamido-2,3-dideoxy-1-S-((3R)-3-dodecanoyloxydodecanoyl)-6-0-hexadecanoyl-1-thio-β-D-glucopyranos-3-yl}-D-lactoyl]-L-alanyl-D-isoglutamine methylester N-[2-0-{2-Acetamido-2,3-dideoxy-1-S-((3R)-3-dodecanoyloxydodecanoyl)-6-0-octadecanoyl-1-thio-β-D-L glucopyranos-3-yl}-D-lactoyl]-L-alanyl-D-isoglutamine methylester N-[2-0-{2-Acetamido-2,3-dideoxy-1-0-((3R)-3-tetradecanoyloxydodecanoyl)-α-D-glucopyranos-3-yl}-D-lactoyl]-L-alanyl-D-isoglutamine methylester N-[2-0-{2-Acetamido-2,3-dideoxy-6-0-dodecanoyl-1-0-((3R)-3-tetadecanoyloxydodecanoyl)-α-D-glucopyrano-s-3- yl)-D-lactoyl]-L-alanyl-D-isoglutamine methylester N-[2-0-{2-Acetamido-2,3-dideoxy-6-0-dodecanoyl-1-0-((3R)-3-tetradecanoyloxydodecanoyl)-α-D-glucopyranos-3-yl}-D-lactoyl]-L-alanyl-D-isoglutamine methylester N-[2-0-{2-Acetamido-2,3-dideoxy-6-0-tetradecanoyl-1-0-((3R)-3-ttradecanoyloxydodecanoyl)-α-D-glucopyranos-3-yl}-D-lactoyl]-L-alanyl-D-isoglutamine methylester N-[2-0-{2-Acetamido-2,3-dideoxy-6-0-hexadecanoyl-1-0-((3R)-3-tetradecanoyloxydodecanoyl)-α-D-glucopyranos-3-yl}-D-lactoyl]-L-alanyl-D-isoglutamine methylester N-[2-0-{2-Acetamido-2,3-dideoxy-6-0-octadecanoyl-1-0-((3R)-3-tetradecanoyloxydodecanoyl)-α-D-glucopyranos-3-yl}-D-lactoyl]-L-alanyl-D-isoglutamine methylester N-[2-0-{2-Acetamido-2,3-dideoxy-1-S-((3R)-3-tetradecanoyloxydodecanoyl)-1-thio-β-D-glucopyranos-3-yl}-D-lactoyl]-L-alanyl-D-isoglutamine methylester N-[2-0-{2-Acetamido-2,3-dideoxy-6-0-decanoyl-1-S-((3R)-3-tetradecanoyloxydodecanoyl)-1-thio-β-D-glucopyranos-3-yl}-D-lactoyl]-L-alanyl-D-isoglutamine methylester N-[2-0-{2-Acetamido-2,3-dideoxy-6-0-dodecanoyl-1-S-((3R)-3-tetradecanoyloxydodecanoyl)-1-thio-β-D-glucopyranos-3-yl}-D-lactoyl]-L-alanyl-D-isoglutamine methylester N-[2-0-{2-Acetamido-2,3-dideoxy-6-0-tetradecanoyl-1-S-((3R)-3-tetradecanoyloxydodecanoyl)-1-thio-β-D-glucopyranos-3-yl}-D-lactoyl]-L-alanyl-D-isoglutamine methylester N-[2-0-{2-Acetamido-2,3-dideoxy-6-0-hexadecanoyl-1-S-[(3R)-3-tetradecanoyloxydodecanoyl)-1-thio-β-D-glucopyranos-3-yl}-D-lactoyl]-L-alanyl-D-isoglutamine methylester N-[2-0-{2-Acetamido-2,3-dideoxy-6-0-octadecanoyl-1-S-((3R)-3-tetradecanoyloxydodecanoyl)-1-thio-β-D-glucopyranos-3-yl}-D-lactoyl]-L-alanyl-D-isoglutamine methylester N-[2-0-{2-Acetamido-2,3-dideoxy-1-0-[(3R)-3-hexadecanoyloxydodecanoyl)-α-D-glucopyranos-3-yl}-D-lactoyl]-L-alanyl-D-isoglutamine methylester N-[2-0-{2-Acetamido-2,3-dideoxy-6-0-decanoyl-1-0-((3R)-3-hexadecanoyloxydodecanoyl-α-D-glucopyranos-3-yl}-D-lactoyl]-L-alanyl-D-isoglutamine methylester N-[2-0-{2-Acetamido-2,3-dideoxy-6-0-dodecanoyl-1-0-((3R)-3-hexadecanoyloxydodecanoyl)-α-D-glucopyranos-3-yl}-D-lactoyl]-L-alanyl-D-isoglutamine methylester N-[2-0-{2-Acetamido-2,3-dideoxy-1-0-[(3R)-3-hexadecanoyloxydodecanoyl)-6-0-tetradecanoyl-α-D-glucopyranos-3-yl}-D-lactoyl]-L-alanyl-D-isoglutamine methylester N-[2-0-{2-Acetamido-2,3-dideoxy-6-0-hexadecanoyl-c. 1-0-{(3R)-3-hexadecanoyloxydodecanoyl)-α-D-glucopyranos-3-yl}-D-lactoyl]-L-alanyl-D-isoglutamine methylester N-[2-0-{2-Acetamido-2,3-dideoxy-1-0-((3R)-3-hexadecanoyloxydodecanoyl)-6-0-octadecanoyl-α-D-glucopyranos-3-yl}-D-lactoyl]-L-alanyl-D-isoglutamine methylester N-[2-0-{2-Acetamido-2,3-dideoxy-1-S-((3R)-3-hexadecanoyloxydodecanoyl)-1-thio-β-D-glucopyranos-3-yl}-D-lactoyl]-L-alanyl-D-isoglutamine methylester N-[2-0-{2-Acetamido-2,3-dideoxy-6-0-decanoyl-1-S-((3R)-3-hexadecanoyloxydodecanoyl)-1-thio-β-D-glucopyranos-3-yl}-D-lactoyl]-L-alanyl-D-isoglutamine methylester N-[2-0-{2-Acetamido-2,3-dideoxy-6-0-dodecanoyl-1-S-((3R)-3-hexadecanoyloxydodecanoyl)-1-thio-β-D-gluco- pyranos-3-yl}-D-lactoyl]-L-alanyl-D-isoglutamine methylester N-[2-0-{2-Acetamido-2,3-dideoxy-1-S-((3R)-3-hexadecanoyloxydodecanoyl)-6-0-tetradecanoyl-1-thio- β-D-glucopyranos-3-yl}-D-lactoyl]-L-alanyl-D-isoglutamine methylester N-[2-0-{2-Acetamido-2,3-dideoxy-6-0-hexadecanoyl-1-S-((3R)-3-hexadecanoyloxydodecanoyl)-1-thio-β-D-glucopyranos-3-yl}-D-lactoyl]-L-alanyl-D-isoglutamine methylester N-[2-0-{2-Acetamido-2,3-dideoxy-1-S-([3R)-3-hexadecanoyloxydodecanoyl)-6-0-octadecanoyl-1-thio-β-D-glucopyranos-3-yl}-D-lactoyl]-L-alanyl-D-isoglutamine methylester N-[2-0-{2-Acetamido-2,3-dideoxy-1-0-((3R)-3-octadecanoyloxydodecanoyl)-α-D-glucopyranos-3-yl}-D-lactoyl]-L-alanyl-D-isoglutamine methylester N-[2-0-{2-Acetamido-2,3-dideoxy-6-0-decanoyl-1-0-((3R)-3-octadecanoyloxydodecanoyl)-α-D-glucopyranos-3-yl)-D-lactoyl]-L-alanyl-D-isoglutamine methylester N-[2-0-{2-Acetamido-2,3-dideoxy-6-0-dodecanoyl-1-0-((3R)-3-octadecanoyloxydodecanoyl)-α-D-glucopyranos-3-yl)-D-lactoyl]-L-alanyl-D-isoglutamine methylester N-[2-0-{2-Acetamido-2,3-dideoxy-1-0-((3R)-3-octadecanoyloxydodecanoyl}-6-0-tetradecanoyl-α-D-glucopyranos-3-yl)-D-lactoyl]-L-alanyl-D-isoglutamine methylester N-[2-0-{2-Acetamido-2,3-dideoxy-6-0-hexadecanoyl-1-0-((3R)-3-octadecanoyloxydodecanoyl)-α-D-glucopyranos-3-yl}-D-lactoyl]-L-alanyl-D-isoglutamine methylester N-[2-0-{2-Acetamido-2,3-dideoxy-6-0-octadecanoyl-1-0-((3R)-3-octadecanoyloxydodecanoyl)-α-D-glucopyranos-3-yl}-D-lactoyl]-L-alanyl-D-isoglutamine methylester N-[2-0-{2-Acetamido-2,3-dideoxy-1-S-((3R)-3-octaL decanoyloxydodecanoyl)-1-thio-β-D-glucopyranos-3-yl)-D-lactoyl]-L-alanyl-D-isoglutamine methylester N-[2-0-{2-Acetamido-2,3-dideoxy-6-0-decanoyl-1-S-((3R)-3-octadecanoyloxydodecanoyl)-1-thio-β-D-glucopyranos-3-yl}-D-lactoyl]-L-alanyl-D-isoglutamine methylester N-[2-0-{2-Acetamido-2,3-dideoxy-6-0-dodecanoyl-1-S-((3R)-3-octadecanoyloxydodecanoyl)-1-thio-β-D-glucoL pyranos-3-yl}-D-lactoyl]-L-alanyl-D-isoglutamine methylester N-[2-0-{2-Acetamido-2,3-dideoxy-1-S-((3R)-3-octadecanoyloxydodecanoyl)-6-0-tetradecanoyl-1-thio-β-D-glucopyranos-3-yl}-D-lactoyl]-L-alanyl-D-isoglutamine methylester N-[2-0-{2-Acetamido-2,3-dideoxy-6-0-hexadecanoyl-1-S-((3R)-3-octadecanoyloxydodecanoyl)-1-thio-β-D-glucopyranos-3-yl}-D-lactoyl]-L-alanyl-D-isoglutamine methylester N-[2-0-{2-Acetamido-2,3-dideoxy-6-0-octadecanoyl-1-S-((3R)-3-octadecanoyloxydodecanoyl)-1-thio-β-D-glucopyranos-3-yl}-D-lactoyl]-L-alanyl-D-isoglutamine methylester N-[2-0-{2-Acetamido-2,3-dideoxy-1-0-((3R)-3-eicosanoyloxydodecanoyl)-α-D-glucopyranos-3-yl}-D-lactoyl]-L-alanyl-D-isoglutamine methylester N-[2-0-{2-Acetamido-2,3-dideoxy-6-0-decanoyl-1-0-((3R)-3-eicosanoyloxydodecanoyl)-α-D-glucopyranos-3-yl}-D-lactoyl]-L-alanyl-D-isoglutamine methylester N-[2-0-{2-Acetamido-2,3-dideoxy-6-0-dodecanoyl-1-0-((3R)-3-eicosanoyloxydodecanoyl)-α-D-glucopyranos-3-yl)-D-lactoyl]-L-alanyl-D-isoglutamine methylester v, N-[2-0-{2-Acetamido-2,3-dideoxy-1-0-((3R)-3-eicosanoyloxydodecanoyl)-6-0-tetradecanoyl-α-D-glucopyranos-3-yl}-D-lactoyl]-L-alanyl-D-isoglutamine methylester N-[2-0-{2-Acetamido-2,3-dideoxy-1-0-((3R)-3-eicosanoyloxydodecanoyl)-6-0-hexadecanoyl-α-D-glucopyranos-3-yl}-D-lactoyl]-L-alanyl-D-isoglutamine methylester N-[2-0-{2-Acetamido-2,3-dideoxy-1-0-[(3R)-3-eicosanoyloxydodecanoyl)-6-0-octadecanoyl-α-D-glucopyranos-3-yl)-D-lactoyl]-L-alanyl-D-isoglutamine methylester N-[2-0-{2-Acetamido-2,3-dideoxy-1-S-((3R)-3-eicosanoyloxydodecanoyl)-1-thio-β-D-glucopyranos-3-yl}-D-lactoyl]-L-alanyl-D-isoglutamine methylester N-[2-0-{2-Acetamido-2,3-dideoxy-6-0-decanoyl-1-S-((3R)-3-eicosanoyloxydodecanoyl)-1-thio-β-D-glucopyranos-3-yl}-D-lactoyl]-L-alanyl-D-isoglutamine methylester N-[2-0-{2-Acetamido-2,3-dideoxy-6-0-dodecanoyl-1-S-((3R)-3-eicosanoyloxydodecanoyl)-1-thio-β-D-glucopyranos-3-yl}-D-lactoyl]-L-alanyl-D-isoglutamine methylester N-[2-0-{2-Acetamido-2,3-dideoxy-1-S-((3R)-3-eicosanoyloxydodecanoyl)-6-0-tetradecanoyl-1-thio-β-D-glucopyranos-3-yl}-D-lactoyl]-L-alanyl-D-isoglutamine methylester N-[2-0-{2-Acetamido-2,3-dideoxy-1-S-((3R)-3-eicosanoyloxydodecanoly)-6-0-hexadecanoyl-1-thio-β-D-glucopyranos-3-yl}-D-lactoyl]-L-alanyl-D-isoglutamine methylester N-[2-0-{2-Acetamido-2,3-dideoxy-1-S-((3R)-3-eicosanoyloxydodecanoyl)-6-0-octadecanoyl-1-thio-β-D-glucopyranos-3-yl}-D-lactoyl]-L-alanyl-D-isoglutamine methylester N-[2-0-{2-Acetamido-2,3-dideoxy-1-0-((3R.)-3-docosanoyloxydodecanol)-α-D-glucopyranos-3-yl}-D-lactoyl]-L-alanyl-D-isoglutamine methylester N-[2-0-{2-Acetamido-2,3-dideoxy--6-0-decanoyl- -1-0-((3R)-3-docosanoyloxydodecanoyl)-α-D-glucopyranos-3-yl}-D-lactoyl]-L-alanyl-D-isoglutamine methylester N-[2-0-{2-Acetamido-2,3-dideoxy-1-0-((3R)-3-docosanoyloxydodecanoyl)-6-0-dodecanoyl-α-D-glucoL pyranos-3-yl}-D-lactoyl]-L-alanyl-D-isoglutamine-methylester N-[2-0-{2-Acetamido-2,3-dideoxy-1-0-((3R)-3-docosanoyloxydodecanoyl)-6-0-tetradecanoyl-α-D-L glucopyranos-3-yl}-D-lactoyl]-L-alanyl-D-isoglutamine methylester N-[2-0-{2-Acetamido-2,3-dideoxy-1-0-[(3R)-3-docosanoyloxydodecanoyl)-6-0-hexadecanoyl-α-D-glucoL pyranos-3-yl)-D-lactoyl]-L-alanyl-D-isoglutamine methylester N-[2-0-{2-Acetamido-2,3-dideoxy-1-0-{(3R)-3-docosanoyloxydodecanoyl)-6-0-octadecanoyl-α-D-glucopyranos-3-yl}-D-lactoyl]-L-alanyl-D-isoglutamine methylester N-[2-0-{2-Acetamido-2,3-dideoxy-1-S-((3R)-3-docosanoyloxydodecanoyl)-1-thio-β-D-glucopyranos3-yl}-D-lactoyl]-L-alanyl-D-isoglutamine methylester N-[2-0-{2-Acetamido-2,3-dideoxy-6-0-decanoyl-1-S-((3R)-3-docosanoyloxydodecanoyl)-1-thio-0-D-glucopyranos-3-yl}-D-lactoyl]-L-alanyl-D-isoglutamine methylester N-[2-0-{2-Acetamido-2,3-dideoxy-1-S-((3R)-3-docosanoyloxydodecanoyl)-6-0-dodecanoyl-1-thio- β-D-glucopyranos-3-yl}-D-lactoyl]-L-alanyl-D-isoglutamine methylester N-[2-0-{2-Acetamido-2,3-dideoxy-1-S-((3R)-3-docosanoyloxydodecanoyl)-6-0-tetradecanoyl-1-thio-β-D-glucopyranos-3-yl}-D-lactoyl]-L-alanyl-D-isoglutamine methylester N-[2-0-{2-Acetamido-2,3-dideoxy-1-S-[(3R)-docosanoyloxydodecanoyl)-6-0-hexadecanoyl-1-thio-β-D-glucopyranos-3-yl}-D-lactoyl]-L-alanyl-D-isoglutamine methylester N-[2-0-{2-Acetamido-2,3-dideoxy-1-S-((3R)-3-docosanoyloxydodecanoyl)-6-0-octadecanoyl-1-thio-β-D-glucopyranos-3-yl}-D-lactoyl]-L-alanyl-D-isoglutamine methylester N-[2-0-{2-Acetamido-2,3-dideoxy-1-0-((3R)-3-tetracosanoyloxydodecanoyl)-α-D-glucopyranos-3-yl}-D-lactoyl]-L-alanyl-D-isoglutamine methylester N-[2-0-{2-Acetamido-2,3-dideoxy-6-0-decanoyl-1-0-((3R)-3-tetracosanoyloxydodecanoyl)-α-D-glucopyranos-3-yl}-D-lactoyl]-L-alanyl-D-isoglutamine methylester N-[2-0-{2-Acetamido-2,3-dideoxy-6-0-dodecanoyl-1-0-((3R)-3-tetracosanoyloxydodecanoyl)-α-D-glucopyranos-3-yl}-D-lactoyl]-L-alanyl-D-isoglutamine methylester N-[2-0-{2-Acetamido-2,3-dideoxy-1-0-((3R)-3-tetracosanoyloxydodecanoyl)-6-0-tetradecanoyl-α-D-glucopyranos-3-yl}-D-lactoyl]-L-alanyl-D-isoglutamine methylester N-[2-0-{2-Acetamido-2,3-dideoxy-6-0-hexadecanoyl-1-0-((3R)-3-tetracosanoyloxydodecanoyl)-α-D-glucopyranos-3-yl}-D-lactoyl]-L-alanyl-D-isoglutamine methylester N-[2-0-{2-Acetamido-2,3-dideoxy-6-0-octadecanoyl-1-0-((3R)-3-tetracosanoyloxydodecanoyl)-α-D-glucopyranos-3-yl}-D-lactoyl]-L-alanyl-D-isoglutamine methylester N-[2-0-{2-Acetamido-2,3-dideoxy-1-S-((3R)-3-tetracosanoyloxydodecanoyl)-1-thio-⊕-D-glucopyranos-3yl}-D-lactoyl]-L-alanyl-D-isoglutamine methylester N-[2-0-{2-Acetamido-2,3-dideoxy-6-0-decanoyl-1-S-((3R)-3-tetracosanoyloxydodecanoyl)-1-thio-β-D-glucopyranos-3-yl}-D-lactoyl]-L-alanyl-D-isoglutamine methylester N-[2-0-{2-Acetamido-2,3-dideoxy-6-0-dodecanoyl- 1-S-((3R)-3-tetracosanoyloxydodecanoyl)-1-thio-β-D-glucopyranos-3-yl}-D-lactoyl]-L-alanyl-D-isoglutamine methylester N-[2-0-{2-Acetamido-2,3-dideoxy-1-S-({3R)-3-tetracosanoyloxydodecanoyl)-6-0-tetradecanoyl-1-thio-β-D-glucopyranos-3-yl}-D-lactoyl]-L-alanyl-D-isoglutamine methylester N-[2-0-{2-Acetamido-2,3-dideoxy-6-0-hexadecanoyl-1-S-((3R)-tetracosanoyloxydodecanoyl)-1-thio-β-D-glucopyranos-3-yl}-D-lactoyl]-L-alanyl-D-isoglutamine methylester N-[2-0-{2-Acetamido-2,3-dideoxy-6-0-octadecanoyl-1-S-((3R)-3-tetracosanoyloxydodecanoyl)-1-thio-β-D-L glucopyranos-3-yl}-D-lactoyl]-L-alanyl-D-isoglutamine methylester N-[2-0-{2-Acetamido-2,3-dideoxy-1-0-((3R)-3-dodecanoyloxyhexadecanoyl)-α-D-glucopyranos-3-yl}-D-lactoyl]-L-alanyl-D-isoglutamine methylester N-[2-0-{2-Acetamido-2,3-dideoxy-6-0-decanoyl-1-0-((3R)-3-dodecanoyloxyhexadecanoyl)-α-D-glucopyranos-3-yl}-D-lactoyl]-L-alanyl-D-isoglutamine methylester N-[2-0-{2-Acetamido-2,3-dideoxy-6-0-dodecanoyl-1-0-((3R}-3-dodecanoyloxyhexadecanoyl)-α-D-glucopyranos-3-yl}-D-lactoyl]-L-alanyl-D-isoglutamine methylester N-[2-0-{2-Acetamido-2,3-dideoxy-1-0-((3R)-3-dodecanoyloxyhexadecanoyl)-6-0-tetradecanoyl-α-D-glucopyranos-3-yl}-D-lactoyl]-L-alanyl-D-isoglutamine methylester N-[2-0-(2-Acetamido-2,3-dideoxy-1-0-((3R)-3-dodecanoyloxyhexadecanoyl)-6-0-hexadecanoyl-α-D-glucopyranos-3-yl}-D-lactoyl]-L-alanyl-D-isoglutamine methylester N-[2-0-{2-Acetamido-2,3-dideoxy-1-0-((3R)-3-dodecanoyloxyhexadecanoyl)-6-0-octadecanoyl-α-D-glucopyranos-3-yl}-D-lactoyl]-L-alanyl-D-isoglutamine methylester N-[2-0-{2-Acetamido-2,3-dideoxy-1-S-((3R)-3-dodecanoyloxyhexadecanoyl)-1-thio-β-D-glucopyranos-3-r yl}-D-lactoyl]-L-alanyl-D-isoglutamine methylester N-[2-0-{2-Acetamido-2,3-dideoxy-6-0-decanoyl-1-S-((3R)-dodecanoyloxyhexadecanoyl)-1-thio-β-D-glucoL pyranos-3-yl}-D-lactoyl]-L-alanyl-D-isoglutamine methylester N-[2-0-{2-Acetamido-2,3-dideoxy-6-0-dodecanoyl-1-S-(3R)-3-dodecanoyloxyhexadecanoyl)-1-thio-β-D-glucopyranos-3-yl}-D-lactoyl]-L-alanyl-D-isoglutamine methylester N-[2-0-{2-Acetamido-2,3-dideoxy-1-S-(3R)-3-dodecanoyloxyhexadecanoyl)-6-0-tetradecanoyl-1-thio-β-D-glucopyranos-3-yl}-D-lactoyl]-L-alanyl-D-isoglutamine methylester N-[2-0-{2-Acetamido-2,3-dideoxy-1-S-((3R)-3-dodecanoyloxyhexadecanoyl)-6-0-hexadecanoyl-1-thio-β-D-glucopyranos-3-yl}-D-lactoyl]-L-alanyl-D-isoglutamine methylester N-[2-0-{2-Acetamido-2,3-dideoxy-1-S-((3R)-3-dodecanoyloxyhexadecanoyl)-6-0-octadecanoyl-1-thio-β-D-glucopyranos-3-yl}-D-lactoyl]-L-alanyl-D-isoglutamine methylester N-[2-0-{2-Acetamido-2,3-dideoxy-1-0-((3R)-3-tetradecanoyloxyhexadecanoyl)-α-D-glucopyranos-3-yl}-D-lactoyl]-L-alanyl-D-isoglutamine methylester N-[2-0-{2-Acetamido-2,3-dideoxy-6-0-decanoyl-1-0-((3R)-3-tetradecanoyloxyhexadecanoyl)-α-D-glucopyranos-L 3-yl}-D-lactoyl]-L-alanyl-D-isoglutamine methylester N-[2-0-{2-Acetamido-2,3-dideoxy-6-0-dodecanoyl-1-0-((3R)-3-tetradecanoyloxyhexadecanoyl)-α-D-glucoL pyranos-3-yl}-D-lactoyl]-L-alanyl-D-isoglutamine methylester N-[2-0-{2-Acetamido-2,3-dideoxy-6-0-tetradecanoyl-1-0-[(3R)-3-tetradecanoyloxyhexadecanoyl)-α-D-glucoi pyranos-3-yl}-D-lactoyl]-L-alanyl-D-isoglutamine methylester N-[2-0-{2-Acetamido-2,3-dideoxy-6-0-hexadecanoyl-1-0-((3R)-3-tetradecanoyloxyhexadecanoyl)-α-D-glucopyranos-3-yl}-D-lactoyl]-L-alanyl-D-isoglutamine methylester N-[2-0-{2-Acetamido-2,3-dideoxy-6-0-octadecanoyl-1-0-((3R)-3-tetradecanoyloxyhexadecanoyl)-α-D-glucopyranos-3-yl}-D-lactoyl]-L-alanyl-D-isoglutamine methylester N-[2-0-{2-Acetamido-2,3-dideoxy-1-S-[(3R)-3-tetradecanoyloxyhexadecanoyl)-1-thio-β-D-glucopyranos-L 3-yl}-D-lactoyl]-L-alanyl-D-isoglutamine methylester N-[2-0-{2-Acetamido-2,3-dideoxy-6-0-decanoyl-1-S-((3R)-3-tetradecanoyloxyhexadecanoyl)-1-thio-β-D-glucopyranos-3-yl}-D-lactoyl]-L-alanyl-D-isoglutamine methylester N-[2-0-{2-Acetamido-2,3-dideoxy-6-0-dodecanoyl-1-S-((3R)-3-tetradecanoyloxyhexadecanoyl)-1-thio-β-D-glucopyranos-3-yl}-D-lactoyl]-L-alanyl-D-isoglutamine methylester N-[2-0-{2-Acetamido-2,3-dideoxy-6-0-tetradecanoyl-1-S-((3R)-tetradecanoyloxyhexadecanoyl)-1-thio-β-D-glucopyranos-3-yl}-D-lactoyl]-L-alanyl-D-isoglutamine methylester N-[2-0-{2-Acetamido-2,3-dideoxy-6-0-hexadecanoyl-1-S-((3R)-3-tetradecanoyloxyhexadecanoyl)-1-thio-β-D-glucopyranos-3-yl}-D-lactoyl]-L-alanyl-D-isoglutamine methylester N-[2-0-{2-Acetamido-2,3-dideoxy-6-0-octadecanoyl-1-S-((3R)-3-tetradecanoyloxyhexadecanoyl)-1-thio-β-D-glucopyranos-3-yl}-D-lactoyl]-L-alanyl-D-isoglutamine methylester N-[2-0-{2-Acetamido-2,3-dideoxy-1-0-((3R)-3-hexadecanoyloxyhexadecanoyl)-α-D-glucopyranos-3-yl}-D-lactoyl]-L-alanyl-D-isoglutamine methylester N-[2-0-{2-Acetamido-2,3-dideoxy-6-0-decanoyl-1-0-((3R)-3-hexadecanoyloxyhexadecanoyl)-α-D-glucopyranos-3-yl}-D-lactoyl]-L-alanyl-D-isoglutamine methylester N-[2-0-{2-Acetamido-2,3-dideoxy-6-0-dodecanoyl-1-0-((3R)-3-hexadecanoyloxyhexadecanoyl)-α-D-glucoL pyranos-3-yl}-D-lactoyl]-L-alanyl-D-isoglutamine methylester N-[2-0-{2-Acetamido-2,3-dideoxy-1-0-((3R)-3-hexadecanoyloxyhexadecanoyl)-6-0-tetradecanoyl-α-D-glucopyranos-3-yl}-D-lactoyl]-L-alanyl-D-isoglutamine methylester N-[2-0-{2-Acetamido-2,3-dideoxy-6-0-hexadecanoyl-1-0-((3R)-3-hexadecanoyloxyhexadecanoyl)-α-D-glucopyranos-3-yl}-D-lactoyl]-L-alanyl-D-isoglutamine methylester N-[2-0-{2-Acetamido-2,3-dideoxy-1-0-([3R)-3-hexadecanoyloxyhexadecanoyl)-6-0-octadecanoyl-α-D-glucopyranos-3-yl}-D-lactoyl]-L-alanyl-D-isoglutamine methylester N-[2-0-{2-Acetamido-2,3-dideoxy-1-S-((3R)-3-hexadecanoyloxyhexadecanoyl)-1-thio-β-D-glucopyranos-3-yl}-D-lactoyl]-L-alanyl-D-isoglutamine methylester N-[2-0-{2-Acetamido-2,3-dideoxy-6-0-decanoyl-1-S-((3R)-3-hexadecanoyloxyhexadecanoyl)-1-thio-β-D-glucopyranos-3-yl}-D-lactoyl]-L-alanyl-D-isoglutamine methylester N-[2-0-{2-Acetamido-2,3-dideoxy-6-0-dodecanoyl-1-S-((3R)-3-hexadecanoyloxyhexadecanoyl)-1-thio-β-D-L glucopyranos-3-yl}-D-lactoyl]-L-alanyl-D-isoglutamine methylester N-[2-0-{2-Acetamido-2,3-dideoxy-1-S-((3R)-3-hexadecanoyloxyhexadecanoyl)-6-0-tetradecanoyl-1-thio-β-D-glucopyranos-3-yl)-D-lactoyl]-L-alanyl-D-isoglutamine methylester N-[2-0-{2-Acetamido-2,3-dideoxy-6-0-hexadecanoyl-1-S-[(3R)-3-hexadecanoyloxyhexadecanoyl)-1-thio-β-D-glucopyranos-3-yl}-D-lactoyl]-L-alanyl-D-isogluta mine methylester N-[2-0-{2-Acetamido-2,3-dideoxy-1-S-((3R)-3-hexadecanoyloxyhexadecanoyl)-6-0-octadecanoyl-1-thio-β-D-glucopyranos-3-yl)-D-lactoyl]-L-alanyl-D-isoglutamine methylester N-[2-0-{2-Acetamido-2,3-dideoxy-1-0-((3R)-3-octadecanoyloxyhexadecanoyl)-α-D-glucopyranos-3-yl)-D-lactoyl]-L-alanyl-D-isoglutamine methylester N-[2-0-{2-Acetamido-2,3-dideoxy-6-0-decanoyl-1-0-((3R)-3-octadecanoyloxyhexadecanoyl)-α-D-glucopyranos-L 3-yl}-D-lactoyl]-L-alanyl-D-isoglutamine methylester N-[2-0-{2-Acetamido-2,3-dideoxy-6-0-dodecanoyl-1-0-((3R)-3-octadecanoyloxyhexadecanoyl)-α-D-glucoL pyranos-3-yl}-D-lactoyl]-L-alanyl-D-isoglutamine methylester N-[2-0-{2-Acetamido-2,3-dideoxy-1-0-((3R)-3-octadecanoyloxyhexadecanoyl)-6-0-tetradecanoyl-α-D-glucopyranos-3-yl}-D-lactoyl]-L-alanyl-D-isoglutamine methylester N-[2-0-{2-Acetamido-2,3-dideoxy-6-0-hexadecanoyl-1-0-((3R)-3-octadecanoyloxyhexadecanoyl)-α-D-glucopyranos-3-yl}-D-lactoyl]-L-alanyl-D-isoglutamine methylester N-[2-0-{2-Acetamido-2,3-dideoxy-6-0-octadecanoyl-1-0-((3R)-3-octadecanoyloxyhexadecanoyl)-α-D-gluco-pyranos-3-yl}-D-lactoyl]-L-alanyl-D-isoglutamine methylester N-[2-0-{2-Acetamido-2,3-dideoxy-1-S-((3R)-3-octadecanoyloxyhexadecanoyl)-1-thio-β-D-glucopyranos-3-yl}-D-lactoyl]-L-alanyl-D-isoglutamine methylester N-[2-0-{2-Acetamido-2,3-dideoxy-6-0-decanoyl-1-S-((3R)-3-octadecanoyloxyhexadecanoyl)-1-thio-β-D-glucoL pyranos-3-yl}-D-lactoyl]-L-alanyl-D-isoglutamine methylester N-[2-0-{2-Acetamido-2,3-dideoxy-6-0-dodecanoyl-1-S-((3R)-3-octadecanoyloxyhexadecanoyl)-1-thio-β-D-glucopyranos-3-yl)-D-lactoyl]-L-alanyl-D-isoglutamine methylester N-[2-0-{2-Acetamido-2,3-dideoxy-1-S-((3R)-3-octadecanoyloxyhexadecanoyl)-6-0-tetradecanoyl-1-thio-β-D-L glucopyranos-3-yl}-D-lactoyl]-L-alanyl-D-isoglutamine methylester N-[2-0-{2-Acetamido-2,3-dideoxy-6-0-hexadecanoyl-1-S-((3R)-3-octadecanoyloxyhexadecanoyl)-1-thio-β-D-glucopyranos-3-yl}-D-lactoyl]-L-alanyl-D-isoglutamine methylester N-[2-0-{2-Acetamido-2,3-dideoxy-6-0-octadecanoyl-1-S-[(3R)-3-octadecanoyloxyhexadecanoyl)-1-thio-β-D- glucopyranos-3-yl}-D-lactoyl]-L-alanyl-D-isoglutamine methylester N-[2-0-{2-Acetamido-2,3-dideoxy-1-0-((3R)-3-eicosanoyloxyhexadecanoyl)-α-D-glucopyranos-3-yl}-D-lactoyl]-L-alanyl-D-isoglutamine methylester N-[2-0-{2-Acetamido-2,3-dideoxy-6-0-decanoyl-1-0-((3R)-3-eicosanoyloxyhexadecanoyl-α-D-glucopyranos-3-yl)-D-lactoyl]-L-alanyl-D-isoglutamine methylester N-[2-0-{2-Acetamido-2,3-dideoxy-6-0-dodecanoyl-1-0-((3R)-3-eicosanoyloxyhexadecanoyl)-α-D-glucopyranos-- 3-yl}-D-lactoyl]-L-alanyl-D-isoglutamine methylester N-[2-0-{2-Acetamido-2,3-dideoxy-1-0-((3R)-3-eicosanoyloxyhexadecanoyl)-6-0-tetradecanoyl-α-D-glucoL pyranos-3-yl}-D-lactoyl]-L-alanyl-D-isoglutamine methylester N-[2-0-{2-Acetamido-2,3-dideoxy-1-0-((3R)-3-eicosanoyloxyhexadecanoyl)-6-0-hexadecanoyl-α-D-glucoL pyranos-3-yl}-D-lactoyl]-L-alanyl-D-isoglutamine methylester N-[2-0-{2-Acetamido-2,3-dideoxy-1-0-((3R)-3-eicosanoyloxyhexadecanoyl)-6-0-octadecanoyl-α-D-glucopyranos-3-yl)-D-lactoyl]-L-alanyl-D-isoglutamine methylester N-[2-0-{2-Acetamido-2,3-dideoxy-1-S-((3R)-3-eicosanoyloxyhexadecanoyl)-1-thio-β-D-glucopyranos-3-yl}-D-lactoyl]-L-alanyl-D-isoglutamine methylester N-[2-0-{2-Acetamido-2,3-dideoxy-6-0-decanoyl-1-S-((3R)-3-eicosanoyloxyhexadecanoyl)-1-thio-β-D-glucoL pyranos-3-yl}-D-lactoyl]-L-alanyl-D-isoglutamine methylester N-[2-0-{2-Acetamido-2,3-dideoxy-6-0-dodecanoyl-1-S-((3R)-3-eicosanoyloxyhexadecanoyl)-1-thio-β-D-glucopyranos-3-yl}-D-lactoyl]-L-alanyl-D-isoglutamine methylester N-[2-0-{2-Acetamido-2,3-dideoxy-1-S-{(3R)-3-eicosanoyloxyhexadecanoyl)-6-0-tetradecanoyl-1-thio-β-D-glucopyranos-3-yl}-D-lactoyl]-L-alanyl-D-isoglutamine methylester N-[2-0-{2-Acetamido-2,3-dideoxy-1-S-((3R)-3-eicosanoyloxyhexadecanoyl)-6-0-hexadecanoyl-1-thio-β-D-glucopyranos-3-yl}-D-lactoyl]-L-alanyl-D-isoglutamine methylester N-[2-0-{2-Acetamido-2,3-dideoxy-1-S-((3R)-3-eicosanoyloxyhexadecanoyl)-6-0-octadecanoyl-1-thio-β-D-glucopyranos-3-yl}-D-lactoyl]-L-alanyl-D-isoglutamine methylester N-[2-0-{2-Acetamido-2,3-dideoxy-1-0-((3R)-3-docosanoyloxyhexadecanoyl)-α-D-glucopyranos-3-yl}-D-lactoyl]-L-alanyl-D-isoglutamine methylester N-[2-0-{2-Acetamido-2,3-dideoxy-6-0-decanoyl-1-0-((3R)-3-docosanoyloxyhexadecanoyl)-α-D-glucopyranos-3-yl}-D-lactoyl]-L-alanyl-D-isoglutamine methylester N-[2-0-{2-Acetamido-2,3-dideoxy-1-0-((3R)-3-docosanoyloxyhexadecanoyl)-6-0-dodecanoyl-α-D-glucopyranos-3-yl}-D-lactoyl]-L-alanyl-D-isoglutamine methylester N-[2-0-{2-Acetamido-2,3-dideoxy-1-0-[(3R)-3-docosanoyloxyhexadecanoyl)-6-0-tetradecanoyl-α-D-glucoL pyranos-3-yl}-D-lactoyl]-L-alanyl-D-isoglutamine methylester N-[2-0-{2-Acetamido-2,3-dideoxy-1-0-((3R)-3-docosanoyloxyhexadecanoyl)-6-0-hexadecanoyl-α-D-glucopyranos-3-yl}-D-lactoyl]-L-alanyl-D-isoglutamine methylester N-[2-0-{2-Acetamido-2,3-dideoxy-1-0-((3R)-3-docosanoyloxyhexadecanoyl)-6-0-octadecanoyl-α-D-glucopyranos-3-yl}-D-lactoyl]-L-alanyl-D-isoglutamine methylester N-[2-0-{2-Acetamido-2,3-dideoxy-1-S-[(3R)-3-docosanoyloxyhexadecanoyl)-1-thio-β-D-glucopyranos-3-yl}-D-lactoyl]-L-alanyl-D-isoglutamine methylester N-[2-0-{2-Acetamido-2,3-dideoxy-6-0-decanoyl-1-S-((3R)-3-docosanoyloxyhexadecanoyl)-1-thio-β-D-glucopyranos-3-yl}-D-lactoyl]-L-alanyl-D-isoglutamine methylester N-[2-0-{2-Acetamido-2,3-dideoxy-1-S-((3R)-3-docosanoyloxyhexadecanoyl)-6-0-dodecanoyl-1-thio-β-D-L glucopyranos-3-yl)-D-lactoyl]-L-alanyl-D-isoglutamine methylester N-[2-0-{2-Acetamido-2,3-dideoxy-1-S-((3R)-3-docosanoyloxyhexadecanoyl)-6-0-tetradecanoyl-1-thio-β-D-glucopyranos-3-yl}-D-lactoyl]-L-alanyl-D-isoglutamine methylester N-[2-0-{2-Acetamido-2,3-dideoxy-1-S-((3R)-3-docosanoyloxyhexadecanoyl)-6-0-hexadecanoyl-1-thio-β-D-L glucopyranos-3-yl}-D-lactoyl]-L-alanyl-D-isoglutamine methylester N-[2-0-{2-Acetamido-2,3-dideoxy-1-S-((3R)-3-docosanoyloxyhexadecanoyl)-6-0-octadecanoyl-1-thio-β-D-r glucopyranos-3-yl)-D-lactoyl]-L-alanyl-D-isoglutamine methylester N-[2-0-{2-Acetamido-2,3-dideoxy-1-0-((3R)-3-tetracosanoyloxyhexadecanoyl)-α-D-glucopyranos-3-yl}-D-lactoyl]-L-alanyl-D-isoglutamine methylester N-[2-0-{2-Acetamido-2,3-dideoxy-6-0-decanoyl-1-0-((3R)-3-tetracosanoyloxyhexadecanoyl)-α-D-glucopyranos-3-yl}-D-lactoyl]-L-alanyl-D-isoglutamine methylester N-[2-0-{2-Acetamido-2,3-dideoxy-6-0-dodecanoyl-1-0-((3R)-3-tetracosanoyloxyhexadecanoyl)-α-D-glucopyranos-3-yl)-D-lactoyl]-L-alanyl-D-isoglutamine methylester N-[2-0-{2-Acetamido-2,3-dideoxy-1-0-((3R)-3-tetracosanoyloxyhexadecanoyl)-6-0-tetradecanoyl-α-D-glucopyranos-3-yl}-D-lactoyl]-L-alanyl-D-isoglutamine methylester N-[2-0-{2-Acetamido-2,3-dideoxy-6-0-hexadecanoyl-1-0-((3R)-3-tetracosanoyloxyhexadecanoyl)-α-D-glucopyranos-3-yl}-D-lactoyl]-L-alanyl-D-isoglutamine methylester N-[2-0-{2-Acetamido-2,3-dideoxy-6-0-octadecanoyl-1-0-((3R)-3-tetracosanoyloxyhexadecanoyl}-α-D-glucopyranos-3-yl}-D-lactoyl]-L-alanyl-D-isoglutamine methylester N-[2-0-{2-Acetamido-2,3-dideoxy-1-S-((3R)-3-tetracosanoyloxyhexadecanoyl)-1-thio-β-D-glucopyranos-3-yl}-D-lactoyl]-L-alanyl-D-isoglutamine methylester N-[2-0-{2-Acetamido-2,3-dideoxy-6-0-decanoyl-1-S-((3R)-3-tetracosanoyloxyhexadecanoyl)-1-thio-β-D-gluco pyranos-3-yl}-D-lactoyl]-L-alanyl-D-isoglutamine methylester N-[2-0-{2-Acetamido-2,3-dideoxy-6-0-dodecanoyl-1-S-((3R)-3-tetracosanoyloxyhexadecanoyl)-1-thio-β-D-glucopyranos-3-yl)-D-lactoyl]-L-alanyl-D-isoglutamine methylester N-[2-0-{2-Acetamido-2,3-dideoxy-1-S-((3R)-3-tetracosanoyloxyhexadecanoyl)-6-0-tetradecanoyl-1-thio-β-D-glucopyranos-3-yl}-D-lactoyl]-L-alanyl-D-isoglutamine methylester N-[2-0-{2-Acetamido-2,3-dideoxy-6-0-hexadecanoyl-1-S-((3R)-3-tetracosanoyloxyhexadecanoyl)-1-thio-β-D-glucopyranos-3-yl}-D-lactoyl]-L-alanyl-D-isoglutamine methylester and N-[2-0-{2-Acetamido-2,3-dideoxy-6-0-octadecanoyl-1-S-((3R)-3-tetracosanoyloxyhexadecanoyl)-1-thio-β-D-glucopyranos-3-yl)-D-lactoyl]-L-alanyl-D-isoglutamine methylester.

The compounds of the present invention can be basically prepared by the following process.

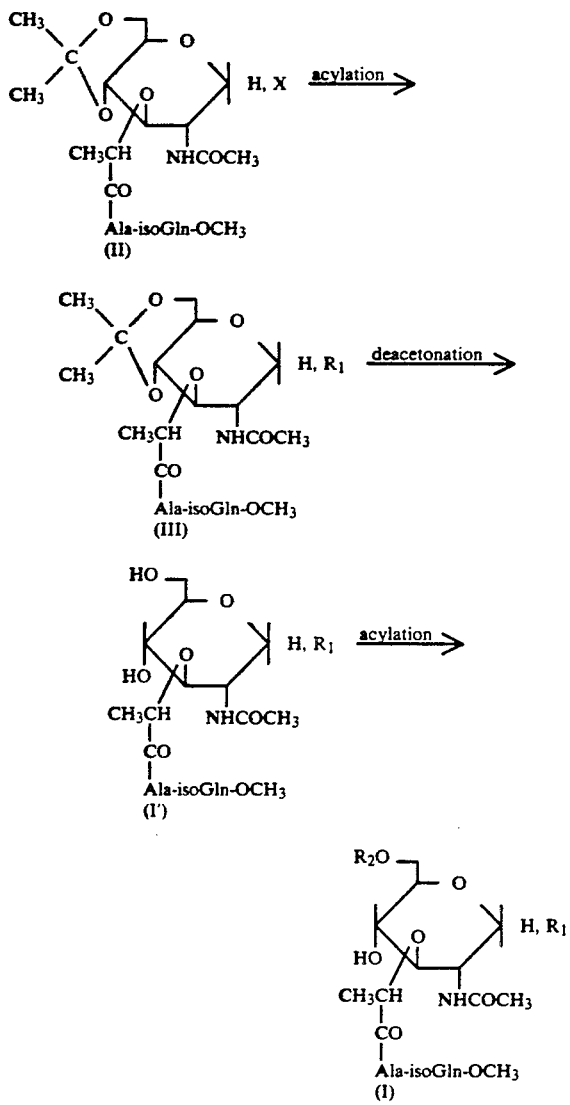

In the formulae, X is OH or SH; $R_1$ and $R_2$ are defined as above.

The above mentioned process consists of two acylation steps (the acylations at 6th and 1st positions of the glucopyranose moiety) and one deacetonation step.

The two acylation steps can be conducted by reacting a compound of the formula (II) or (I') with a specific acylating agent ($R_2H$, $R_3H$ or its reactive derivative). These steps are generally carried out in an anhydrous organic solvent (for example, dimethylformamide or dioxane) and at room temperature or a slightly elevated temperature. When $R_2H$ or $R_3H$ (a free acid) is used, it is conducted in the presence of an appropriate condensing agent (for example, dicyclohexylcarbodiimide, N-cyclohexyl-N'-morpholinoethylcarbodiimide, N-cyclohexyl-N'-(4-diethylaminocyclohexyl)-carbodiimide or N,N'-diethylcarbodiimide). Examples of reactive derivatives of $R_2H$ or $R_3H$ are conventional reactive derivatives used in acylation, such as mixed acid anhydrides, active esters, acid halides and the like. The deacetonating step can be readily conducted under an acid hydrolysis condition (e.g., using 80% acetic acid aqueous solution) at a slightly elevated temperature.

The compounds of the formula (II) are known or can be readily prepared by known methods.

The compounds obtained by the above process may be purified by a conventional method such as a column chromatography using alumina or silica gel, recrystallization and the like.

The compounds of the formula (I) of the present invention have an action for enhancing function of cells relevant to in vivo immune response and an action for increasing the number of said cells, and hence they are useful as an immunoregulating agent. The immunoregulating agent of the present invention can be used to enhance in vivo activities of vaccines such as BCG vaccine, hepatitis vaccine, influenza virus vaccine or the like, various antibacterial agents or anti-tumor agents.

The immunoregulating composition of the present invention comprises a compound of the formula (I) and a pharmaceutically acceptable carrier. The composition may be any dosage form for oral and parenteral administrations.

The compositions for oral administration are generally dosage forms such as powders, tablets, emulsions, capsules, granules and liquid prepartions (including liquid extracts, syrups and the like).

Examples of carriers for powders or other orally administrable solid preparations include lactose, starch, dextrin, calcium phosphate, calcium carbonate, synthetic or natural aluminium silicate, magnesium oxide, dried aluminium hydroxide, magnesium stearate, sodium bicarbonate, dried yeast and the like, and those for liquid preparations include water, glycerine, propylene glycol, simple syrup, ethanol, fatty oil, ethylene glycol, polyethylene glycol, sorbitol and the like. A typical example of the composition for parenteral administration is an injection. Liquid carriers for the injection include sterile distilled water. When a compound of the formula (I) is less soluble in water, an appropriate solubilizer is used. Each of the above preparations can be prepared by conventional methods.

When the compounds of the formula (II) of the present invention are used for enhancement of antitumor agents, they may be orally or parenterally administered to an adult human in an amount of 150 to 250µg/day in one dose. When used for enhancement of vaccines, they may be administered to an adult human in an amount of 0.5 to 2.0 mg/1 to 2 weeks in one dose. For treatment of hepatitis, they may be orally or parenterally administered to an adult human 1 to 3 times for 3 months in an amount of 0.5 to 2.0 mg in one dose. For enhancement of antibacterial agents, they may be used to an adult human in an amount 20 to 100µg/day in one dose.

The immunoregulating agents of the present invention may be generally used by formulating themselves only as described above. But they may be formulated together with an agent to be enhanced its action.

Further, the immunoregulating agents of the present invention can be used for not only humans but also other mammals such as pigs, bovines, sheeps, dogs, and cats.

The present invention is illustrated with following examples.

EXAMPLE 1

N-[2-0-i2-Acetamido-2,3-dideoxy-1-0-[2-tetra-decyl-hexadecanoyl)-α-D-glucopyranos-3-yl}-D-lactoyl]-L--alanyl-D-isoglutamine methylester The compound of the formula (III) wherein $R_1$ is 2-tetradecylhexadecanoyloxy group (279.4 mg, 0.281mmol) was dissolved in 80% acetic acid aqueous solution (8 ml) and the resultant was allowed to stand for 2 hours at 45° C. After confirming the completion of the reaction with T.L.C.($CH_2Cl_2$:MeOH=10:1), the resultant was concentrated under reduced pressure to obtain quantitatively the title compound (266.2 mg).

mp : 147.0°–148.0° C.
$[\alpha]_D^{25}$: +44.38° (c=1.050, $CH_2Cl$ : MeOH=1 : 1)
IR $\gamma$max(KBr)cm$^{-1}$:3350, 2930, 2850, 1740, 1650, 1520
NMR($CD_3OD$—$CHCl_3$)$\delta$(ppm) : 0.88(t,6H,J=6.6 Hz), 1.26(s,48H), 1.38–1.43(m,6H), 1.51–1.62(m,4H), 1.93(s,3H), 3.70(s,3H), 6.16(d,1H,J=4.0 Hz)

EXAMPLE 2

N-{2-0-2-Acetamido-2,3-dideoxy-1-S-(2-tetradecylhexadecanoyl)-1-thio-$\beta$-D-glucopyranos-3-yl]-D-lactoyl}-L-alanyl-D-isoglutamine methylester The compound of the formula (III) wherein $R_1$ is 2-tetradecylhexadecanoylthio group (133.7 mg) was dissolved in 80% acetic acid aqueous solution (15 ml), which was allowed to react for 2 hours at 45° C. After confirming the completion of the reaction with T.L.C., the resultant was concentrated under reduced pressure and crystallized from ether to obtain quantitatively the title compound (127.0 mg, crystals).

mp:130.0°–131.0° C. $[\alpha]_D^{25}$:+46.79° (c=1,201, $CH_2Cl_2$:MeOH=1:1)
IR$\gamma$max(KBr)cm$^{-1}$:3300, 2920, 2850, 1720, 1630, 1530

EXAMPLE 3

N-[2-0-{2-Acetamido-2,3-dideoxy-1-0-((3R)-3-tetradecanoyloxytetradecanoyl)-$\alpha$-D-glucopyranos-3-yl}-D-lactoyl]-L-alanyl-D-isoglutamine methylester The compound of the formula (III wherein $R_1$ is 3-tetradecanoyloxytetradecanoyloxy group (409.1 mg, 0.411mmol) was dissolved in 80% acetic acid aqueous solution 15 ml and allowed to stand for an hour at 45° C. In the same manner as that in Example 1, the title compound was quantitatively obtained (386.9 mg).

mp : 133.8°–134.6° C. $[\alpha]_D^{25}$:+44.74° (c=1.180, $CHCl_3$ MeOH=1:1)
IR $\gamma$max(KBr)cm$^{-1}$: 3700–3140, 2930, 2850, 1740, 1250, 1630, 1540
NMR($CDCl_3$)$\delta$:0.89(t,6H,J=2.2 Hz), 1.27(m,36H), 1.43(m,6H), 1.60(m,4H), 2.00(s,3H), 2.10–2.30[m,4H], 2.44–2.67(m,6H), 3.68(s,3H), 5.31(m,1H), 6.05(d,1H)

EXAMPLE 4

N-[2-0-{2-Acetamido-2,3-dideoxy-1-S-[[3R)-3-tetradecanoyloxytetradecanoyl)-1-thio-$\beta$-D-glucopyranos-3-yl}-D-lactoyl]-L-alanyl-D-isoglutamine methylester The compound of the formula (III) wherein $R_1$ is 3-tetradecanoyloxytetradecanoylthio group (580.1 mg, 0.5808mmol) was dissolved in 80% acetic acid aqueous solution 12 ml and allowed to stand for an hour at 45° C. After confirming the completion of the raction with T.L.C. ($CH_2Cl_2$:MeOH=10 1), the resultant was concentrated under reduced pressure. The resulting syrup was lyophilized to obtain quantitatively the title compound (555.2 mg, crystals).
mp : 110°–111° C.

$[\alpha]_D^{25}$:+26.68° (c=0.787, $CH_2Cl_2$:MeOH=2 1)
IR $\gamma$max(KBr)cm$^{-1}$: 3650–3130, 3300, 2940, 2860, 1740, 1650, 1550,
NMR($CDCl_3$—$CD_3OD$)$\delta$:0.88 (t,6H,J=6.6 Hz), 1.25(m,36H), 1.35 (d,3H,J=7.0 Hz), 1.39 (d,3H,J=7.3 Hz), 1.43–1.58 (m,4H), 1.93(s,3H), 1.93–2.04 (m,2H), 2.09–2.87(m,6H), 3.71(s,3H), 4.05(t,1H,J= 10.4 Hz), 4.28–4.33(m,1H), 4.31(q,1H,J=7.0 Hz), 4.38–4.43 (m,1H), 5.12(d,1H,J=11.0 Hz) 5.17–5.26(m,1H)

EXAMPLE 5

N-[2-0-i2-Acetamido-2,3-dideoxy-6-0-decanoyl-1-0-(2-tetradecylhexadecanoyl)-$\alpha$-D-glucopyranos-3-yl}-D-lactoyl]-L-alanyl-D-isoglutamine methylester The compound of the formula (I) wherein $R_1$ is 2-tetradecylhexadecanoyloxy group (143.3 mg, 0.150mmol) was dissolved in a mixture of dry dioxane (1.3 ml.) and dry N,N-dimethylformamide (DMF, 1.3 ml). To the solution were added decanoic acid (29.6 mg, 0.180mmol), dicyclohexylcarbodiimide (DCC, 61.7 mg, 0.300mmol) and dimethylaminopyridine (DMAP, 9.1 mg, 0.075mmol), and the resultant was stirred for 14 hours at room temperature. After the completion of the reaction, the reaction mixture was concentrated under reduced pressure. The resulting syrup was subjected to a column chromatography [Wakogel ®C-200 eluted with $CH_2CL_2$/MeOH ((a) 150:1 and (b) 20:1)] and the eluate eluted with the eluent (b) was concentrated under reduced pressure. The resultant syrup was subjected to a column chromatography [active alumina 90 eluted with $CH_2Cl_2$/MeOH ((a') 150:1 and (b') 20:1)], to remove DMAP and the eluate eluted with eluent (b') gave the title compound (121.3 mg, yield: 72.6%).

m;:116.31°–117.0° C.
$[\alpha]_D^{25}$:+42.56°(C=0.726, $CHCl_3$:MeOH=2:1)
IR$\gamma$max(KBr)cm$^{-1}$:3650–3150, 2940, 2870 1740, 1650, 1540
NMR($CDCl_3$)$\delta$:0.88(t,6H,J=6.8 Hz), 0.92(t,3H,J=7.1 Hz), 1.25(m,62H), 1.39(d,3H,J=6.6 Hz), 1.41(d,3H,J=6.6 Hz), 1.51–1.60(m,6H), 1.90–2.23(m,2H), 1.94(s,3H), 2.33(t,2H,J-7.5 Hz), 2.39–2.50(m,3H), 3.69(s,3H), 6.18(d,1H,J=3.7Hz)

EXAMPLE 6

N-[2-0-{2-Acetamido-2,3-dideoxy-6-0-tetradecanoyl-1-0-(2-tetradecylhexadecanoyl)-$\alpha$-D-glucopyranos-3-yl}-D-lactoyl]-L-alanyl-D-isoglutamine methylester The compound of the formula (I') wherein $R_1$ is 2-tetradecylhexadecanoyloxy group (1.39.7 mg, 0.147 mmol) is dissolved in a mixture of dry dioxane (2 ml) and dry DMF (2 ml). To the solution were added tetradecanoic acid (40.0 mg, 0.176 mmol), DCC(60.2 mg, 0.294 mmol) and DMAP(8.9 mg, 0.074 mmol). The resultant was stirred for 12 hours at room temperature and then treated in the same manner as that in Example 5 to obtain the title compound (105.4 mg, yield: 61.7%).
mp:116.8°–117.7° C.
$[\alpha]_D^{25}$:+29.22°(c=1.054, $CH_2Cl_2$)
IR$\gamma$max(KBr)cm$^{-1}$:3700–3100, 2940, 2860, 1740, 1660, 1540
NMR($CDCl_3$)$\delta$:0.88(t,9 H,J=6.4 Hz), 1.25(m,7H) 1.38)d,3H, J=6.6 Hz), 1.41(d,3H, J=7.3 Hz), 1.49–1.60(m,6H), 1.93(s,3H), 2.03–2.21(m,2H), 2.32(t,2H,J=7.7 Hz), 2.38–2.74(m,3H), 3.68(s,3H), 6.17(d,1H,J=3.7 Hz)

ESAMPLE 7

N-[2-0-{2-Acetamido-2,3-dideoxy-6-0-octadecanoyl-1-0-(2-tetradecylhexadecanoyl)-α-D-glucopyranos-3-yl}-D-lactoyl]-L-alanyl-D-isoglutamine methylester

The compound of the formula (I') wherein $R_1$ is 2-tetradecylhexadecanoyloxy group (122.7 mg, 0.129 mmol) was dissolved in a mixture of dry dioxane (1.5 ml) and dry DMF(0.5 ml). To the solution were added octadecanoic acid (44.5 mg, 0.155 mmol), DCC(53.7 mg, 0.258 mmol) and DMAP(7.9 mg, 0.065 mmol). The resultant was stirred for 14 hours and then treated in the same manner as that in Example 5 to obtain the title compound(119.0 mg, yield:75.6%).

mp:118.7°-102.0° C.
$[\alpha]_D^{25}$: +39.45°(c=0.621, CHCl$_3$:MeOH=2:1)
IRγmax(KBr)cm$^{-1}$:3650-3150, 2930, 2860, 1740, 1650, 1540
NMR(CDCl$_3$)δ:0.88(t,9H,J=6.6 Hz), 1.25(m,78H), 1.39(d,3H,J=6.6 Hz), 1.41(d,3H,J=6.6 Hz), 1.49-1.60(m,6H), 1.94(s,3H), 1.90-2.26(m,2H), 2.32(t,2H,J=7.3 Hz), 2.39-2.50(m,3H), 3.69(s,3H), 6.18(d,1H,J=3.7 Hz)

EXAMPLE 8

N-[2-0-{2-Acetamido-2,3-dideoxy-6-0-decanoyl-1-S-(2-tetradecylhexadecanoyl)-1-thio-β-D-glucopyranos-3--yl}-D-lactoyl]-L-alanyl-D-isoglutamine methylester

The compound of the formula (I') wherein $R_1$ is 2-tetradecylhexadecanoylthio (128.4 mg, 0.134 mmol) was dissolved in a mixture of dry dioxane (1.5 ml) and dry DMF (1.0 ml). To the solution were added decanoic acid (27.4 mg, 0.161 mmol), DCC(54.6 mg, 0.268 mmol) and DMAP(8.1 mg, 0.067 mmol). The resultant was stirred for 6.5 hours at room temperature. After confirming the completion of the reaciton with T.L.C. (10:1), the resultant was lyophilized and subjected to a column chromatography [Wakogel®C-200 eluted with CH$_2$Cl$_2$/MeOH ((a) 150:1 and (b) 50:1)]. The elute eluted with the eluent (b) gave the title compound (99.6 mg, yield: 66.8%).

mp:98.6°-99.4° C.
$[\alpha]_D^{25}$: +17.69°(c=0.797, CH$_2$Cl$_2$:MeOH=2:1)
IRγmax(KBr)cm$^{-1}$:3500-3200, 2950, 2880, 1750, 1640, 1560
NMR(CDCl$_3$—CD$_3$OD)δ:0.88(t,6H,J=6.6 Hz), 0.92(t,3H,J=7.1 Hz), 1.25(m,56H), 1.34(d,3H,J=6.6 Hz), 1.40(d,3H,j=7.0 Hz), 1.58-1.71(m,6H), 1.90(s,3H), 1.94-2.24(m,2H), 2.33(t,2H,J=7.5 Hz), 2.42-2.52(m,3H), 3.69(s,3H), 5.11(d,1H,J=10.6 Hz)

EXAMPLE 9

N-[2-0-{2-Acetamido-2,3-dideoxy-6-0-tetradecanoyl-1-S-(2-tetradcylhexadecanoyl)-1-thio-β-D-glucopyranos-3-yl}-D-lactoyl]-L-alanyl-D-isoglutamine methylester

The compound of the formula (I') wherein $R_1$ is 2-tetradecylhexadecanoylthio group (125.0 mg, 0.131 mmol) was dissolved in a mixture of dry dioxane (1.5 ml) and dry DMF (1.0 ml). To the solution were added tetradecanoic acid (353.3 mg, 0.157 mmol), DCC(53.1 mg, 0.262 mmol) and DMAP (7.9 mg, 0.066 mmol). The resultant was stirred for 3 hours at room temperature and then treated in the same manner as that in Example 8 to obtain the title compound (1.25.8 mg, yield: 82.5%).

mp:99.0°-100.4° C.
$[\alpha]_D^{25}$: +2.13°(c=2.16, CH$_2$Cl$_2$)
IRγmax(KBr)cm$^{-1}$:3650-3200, 2930, 2860, 1740, 1650, 1550
NMR(CDCl$_3$)δ:0.85-0.95(m,9H), 1.25(m,68H), 1.36(d,3H,J=6.6 Hz), 1.41(d,3H,J=7.3 Hz), 1.47-1.76(m,6H), 1.88-2.32(m,2H), 1.94(s,3H), 2.35(t,2H,J=7.9 Hz), 2.47-2.53(m,3H), 3.70(s,3H), 5.12(d,1H,J=10.3 Hz)

EXAMPLE 10

N-[2-0-{2-Acetamido-2,3-dideoxy-6-0-octadecanoyl-1-S-(2-tetradecylhexadecanoyl)-1-thio-β-D-glucopyranos-3-yl}-D-lactoyl]-L-alanyl-D-isoglutamine methylester

The compound of the formula (I') wherein $R_1$ is 2-tetradecylhexadecanoylthio (122.4 mg, 0.128 mmol) was dissolved in a mixture of dry dioxane (1.5 ml) and dry DMF (1.0 ml). To the solution were added octadecanoic acid (43.0 mg, 0.145 mmol), DCC(52.0 mg, 0.245 mmol) and DMAP (7.7 mg, 0.064 mmol). The resultant was stirred for 4 hours at room temperature and treated in the same manner as that in Example 8 to obtain the title compound (102.7 mg, yield:65.6%).

mp:99.3°-101.0° C.
$[\alpha]_D^{25}$: +2.06° (c=0.376, CH$_2$Cl$_2$:MeOH=2:1)
IRγmax(KBr)cm$^{-1}$:3600-3150, 2920, 2840, 1740, 1640, 1540
NMR(CDCl$_3$-CD$_3$OD)δ:0.88(t,9H,J=6.6 Hz), 1.26(m,76H), 1.35(d,3H,J=6.6 Hz), 1.40(d,3H,J=7.3 Hz), 1.58-1.61(m,6H), 1.88(s,3H), 1.92-2.26(m,2H), 2.33(t,2H,J≤7.7 Hz), 2.41-2.55(m,3H), 3.69(s,3H), 4.40(q,1H), 5.10(d,1H,J=11.0 Hz)

EXAMPLE 11

N-[2-0-{2-Acetamido-2,3-dideoxy-6-0-decanoyl-1-0((3R)-3-tetradecanoyloxytetradecanoyl)-α-D-glucopyranos-3-yl}-D-lactoyl]-L-alanyl-D-isoglutamine methylester

The compound of the formula (I') wherein $R_1$ is 3-tetradecanoyloxytetradecanoyloxy group (116.9 mg, 0.121 mmol) was dissolved in a mixture of dioxane (1.5 ml) and dry DMF (0.5 ml). To the solution were added decanoic acid (24.3 mg, 0.145 mmol), DCC (48.4 mg, 0.242 mmol) and DMAP (7.2 mg, 0.161 mmol). The resultant was stirred for 8 hours at room temperature. After confirming, the completion of the reaction with T.L.C. (CH$_2$Cl$_2$:MeOH=10:1), the resultant was concentrated under reduced pressure. The resulting syrup was subjected to a column chromatography [Wakogel® C-200 eluted with CH$_2$Cl$_2$/MeOH ((a) 150:1 and (b) 35:1)]. The eluate eluted with the eluent (b) gave the title compound (80.4 mg, yield:59.6%).

mp:72.0°-72.8° C.
$[\alpha]_D^{25}$: +27.86°(c=0.804, Ch$_2$Cl$_2$)
IRγmax(Film)cm$^{-1}$:3700-3100, 2930, 2850, 1740, 1650, 1540
NMR(CDCl$_3$)δ:0.88(t,9H,J=6.6 Hz), 1.25-1.27(m,48H), 1.43(d,3H, J=6.6 Hz) 1.45(d,3H,J=7.0 Hz), 1.61(m,6H), 2.00(s,3H), 2.04-2.24(m,2H), 2.30(t,2H, J=7.5 Hz), 2.32-2.67(m,6H), 3.69(s,3H), 4.21(q,1H,J=6.6 Hz), 5.29(m,1H), 6.05(d,1H,J=3.3 Hz)

EXAMPLE 12

N-[2-O-{2-Acetamido-2,3-dideoxy-6-O-tetradecanoyl-1-O-((3R)-3-tetradecanoyloxytetradecanoyl)-α-D-glucopyranos-3yl}-D-lactoyl]-L-alanyl-D-isoglutamine methylester The compound of the formula (I') wherein $R_1$ is 3-tetradecanoyloxytetradecanoyloxy (108.6 mg, 0.15 mmol) was dissolved in a mixture of dry dioxane (1.5 ml) and dry DMF (0.5 ml). To the solution were added tetradecanoic acid (30.1 mg, 0.137 mmol), DCC(45.3 mg, 0.228 mmol) and DMAP (6.7 mg, 0.057 mmol). The mixture was allowed to react for 14 hours at room temperature. The resultant was treated in the same manner as that in Example 11 to obtain the title compound (99.1 mg, yield: 74.6%).

mp:72.5°–73.6° C.
$[α]_D^{25}$:+26.51°(c=1.388CH$_2$Cl$_2$)
IRγmax(film)cm$^{-1}$:3700–3150, 2930, 2850, 1740, 1660, 1540
NMR(CDCl$_3$)δ:0.88(t,9H,J=6.6 H), 1.25–1.38(m,56H), 1.43(d,3H,J=6.6 Hz), 1.45(d,3H,J=7.0 Hz), 1.60(m,6H), 1.99(s,3H), 2.06–2.24(m,2H), 2.30(t,2H,J=7.5 Hz), 2.32–2.66(m,6H), 3.69(s,3H), 4.21(q,1H,J=7.0 Hz), 5.30(m,1H), 6.05(d,1H,J=3.3 Hz)

EXAMPLE 13

N-[2-O-{2-Acetamido-2,3-dideoxy-6-O-octadecanoyl-1-O-((3R)-3-tetradecanoyloxytetradecanoyl)-α-D-glucopyranos-3-yl}-D-lactoyl]-L-alanyl-D-isoglutamine methylester The compound of the formula (I') wherein $R_1$ is 3-tetradecanoyloxytetradecanoyl group (108.8 mg, 0.114 mmol) was dissolved in a mixture of dry dioxane (1.5 ml) and dry DMF (0.5 ml). To the solution were added octadecanoic acid (37.6 mg, 0.137 mmol), DC (45.4 mg, 0.228 mmol) and DMAP (6.7 mg, 0.057 mmol). The resultant was stirred for 14 hours at room temperature and then treated in the same manner as that in Example 11 to obtain the title compound (95.6 mg, yield:68.5%).

mp:68.1°–69.0° C.
$[α]_D^{25}$:+26.15°(c=1.338, CH$_2$Cl$_2$) IRγmax(film)cm$^{-1}$:3700–3150, 2930, 2850, 1740, 1650, 1540
NMR(CDCl$_3$)δ:0.88(t,9H,J=6.6 Hz), 1.25–1.39(m,64H), 1.43(d,3H,J=6.6 Hz), 1.44(d,3H,J=7.0 Hz), 1.58–1.60(m,6H), 1.99(s,3H), 2.02–2.22(m,2H), 2.30(t,2H,J=7.5 Hz), 2.32–2.67(m,6H), 3.69(s,3H0, 4.21(q,1H,J=6.6 Hz), 5.30(m,1H), 6.05(d,1H,J=3.3 Hz)

EXAMPLE 14

N-[2-O-{2-Acetamido-2,3-dideoxy-6-O-decanoyl-1-S-((3R)-R-tetradecanoyloxytetradecanoyl)-1-thio-β-D-glucopyranos-3yl}-D-lactoyl]-L-alanyl-D-isoglutamine methylester The compound of the formula (I) wherein $R_1$ is 3-tetradecanoyloxytetradecanoylthio (239.2 mg, 0.250 mmol) was dissolved in a mixture of dry dioxane (0.5 ml) and dry DMF (0.5 ml). To the solution were added decanoic acid (51.6 ml, 0.300 mmol), DCC (102.9 mg, 0.50 mmol) and DMAP (15.2 mg, 0.499 mmol), and the resultant was stirred for 2 hours at room temperature. After confirming the completion of the reaction with T.L.C. (CH$_2$Cl$_2$:MeOH=10:1), DC urea of a reaction by-product was filtered off and washed with dioxane. The filtrate and washings were combined and then lyophilized. The amorphous material thus obtained was subjected to a column chromatography [Wakogel® C-200 eluted with CH$_2$Cl$_2$/MeOH ((a) 200:1, (b) 70:1, (c) 60:1 and (d) 40:1)]. The eluate eluted with the eluent (c) gave the title compound (111.6 mg, yield: 40.2%).

mp:138.6°–139.9° C.
$[α]_D^{25}$:+17.09° (c=0.70, CH$_2$Cl$_2$:MeOH=2:1)
IRγmax(film)cm$^{-1}$:3650–3020, 3250, 2930, 2850, 1740, 1660, 1540
NMR(CDCl$_3$)δ:0.87(t,9H,J=5.7 Hz), 1.25(m,52H), 1.39(d,3H,J=6.6 Hz), 1.58(m,6H), 1.95(s,3H), 2.10–2.28(m,2H), 2.34(6,2H,J=7.7 Hz), 2.47–2.91(m,6H), 3.69(s,3H), 5.13(d,1H,J=11.0 Hz), 5.11–5.21(m,1H)

EXAMPLE 15

N-[2-O-{2-Acetamido-2,3-dideoxy-6-O-tetradecanoyl-1-S-((3R)-3-tetradecanoyloxytetradecanoyl-1-thio-β-D-glucopyranos-3-yl}-D-lactoyl]-L-alanyl-D-isoglutamine methylester The compound of the formula (I') wherein $R_1$ is 3-tetradecanoyloxytetradecanoylthio (206.5 mg, 0.215 mmol) was dissolved in dry dioxane (0.5 ml) and dry DMF (0.5 ml). To the solution were added tetradecanoic acid (59.0 mg, 0.259 mmol), DCC (88.9 mg, 0.431 mmol) and DMAP (13.1 mg, 9.1077 mmol). The resultant was stirred for 2.5 hours at room temperature and then treated in the same manner as that in Example 14 to obtain the title compound (95.6 mg, yield:38.0%).

mp:136.1°–137.7° C.
$[α]_D^{25}$:+17.57°(c=0.956, CH$_2$Cl$_2$:MeOH=2:1)
IRγmax(film)cm$^{-1}$:3650–3120, 3300, 2930, 2860, 1740, 1640, 1540
NMR(CDCl$_3$)δ:0.88(t,9H,J=6.6 Hz), 1.25(m,56H), 1.39(d,3H,J=7.0 Hz), 1.42 (d,3H,J=7.0 Hz), 1.57(m,6H), 1.97(s,3H), 2.01–2.28(m,2H), 2.34(t,2H,J=7.7 Hz), 3.71(s,3H), 5.13(d,1H,J=11.0 Hz), 5.11–5.23(m,1H)

EXAMPLE 16

N-[2-O-{2-Acetamido-2,3-dideoxy-6-O-octadecanoyl-1-S-((3R)-3-tetradecanoyloxytetradecanoyl)-1-thio-β-D-glucopyranos-3-yl}-D-lactoyl]-L-alanyl-D-isoglutamine methylester The compound of the formula (I') wherein $R_1$ is 3-tetradecanoyloxytetradecanoylthio (203.2 mg, 0.212 mmol) was dissolved in a mixture of dry dioxane (0.5 ml) and dry DMF (0.5 ml). To the solution were added octadecanoic acid (63.1 mg, 0.254 mmol), DCC (87.5 mg, 0.424 mmol) and DMAP (12.9 mg, 0.106 mmol). The resultant was stirred for 3 hours at room temperature and then treated in the same manner as that in Example 14 to obtain the title compound (112.2 mg, yield:43.2%).

mp:133.7°–134.5° C.
$[α]_D^{25}$:+17.46° (c=1.122, CH$_2$Cl$_2$:MeOH=2:1)
IRγmax(film)cm$^{-1}$:3700–3150, 3320, 2960, 2900, 1750, 1680, 1580
NMR(CDCl$_3$)δ:0.87(6,9H,J=5.5 Hz), 1.25(m,6.6H), 1.39(d,3H,J=5.9 Hz), 1.57(m,6H), 1.95(s,3H), 1.95–2.18(m,2H), 2.25–2.90(m,6H), 2.38(t,2H,J=7.1 Hz), 3.69(s,3H), 5.13(d,1H,J=11.0 Hz), 5.11–5.20(m,1H)

EXAMPLE 17

N-[2-0-{2-Acetamido-2,3-dideoxy-1-0-((3R)-3-hexadecanoyloxytetradecanoyl)-α-D-glucopyranos-3-yl}-D-lactoyl]-L-alanyl-D-isoglutamine methylester The compound of the formula (II) wherein $R_1$ is 3-hexadecanoyloxytetradecanoyloxy (408.8 mg, 0.410 mmol) was dissolved in 80% acetic acid aqueous solution (15 ml), which was allowed to stand for 1.5 hours at 45° C. In the same manner as that in Example 4, the title compound (391.7 mg) was quantitatively obtained from the above solution.

m.p.:134.2°–135.5° C.

$[\alpha]_D^{25}$:+47.38° (c=0.878, $CH_2Cl_2$:MeOH=1:1)

IRγmax(cm)$^{-1}$:3700–3100(OH), 3300(NH), 2930, 2850(CH), 1740(ester), 1650, 1530(amido)

NMR(DCDl$_3$)δ:0.88(t,9H,JMeCH$_2$6 Hz, 3MeCH$_2$), 1.25(m,40H,30 CHz), 1.42(d,3H,$J_{MeCH}$7.3 Hz, Mec of Ala), 1.45(d,3H,$J_{MeCH}$7.3 Hz,Hec of Lac), 1.57–1.60(m,6H,3MeCh$_2$), 1.95–2.17(m,2H,CH$_2$CH of Gln), 2.00(s,3H,AcN), 2.30(t,2H,JCH$_2$CH$_2$7.5 Hz,CH$_2$CO of Gln), 2.37–2.66(m,6H,3CH$_2$CO), 3.68(S,3H,COOMe), 5.30–5.42(m,1H,H—3 of $C_{17}$—O—$C_{16}$), 6.03(d,1H,$J_{1,2}$,3.3 Hz,H—1),

EXAMPLE 18

N-[2-0-{2-Acetamido-2,3-dideoxy-6-0octadecanoyl-1-0-((3R)-3-hexadecanoyloxytetradecanoyl)-α-D-glucopyranos-3-yl}-D-lactoyl]-L-alanyl-D-isoglutamine methylester The compound of the formula (I') wherein $R_1$ is 3-hexadecanoyloxytetradecanoyloxy (191.1 mg, 0.200 mmol) was dissolved in a mixture of dry dioxane (3.0 ml) and dry DMF (1.0 ml). To the solution were added octadecanoic acid (74.0 mg, 0.260 mmol), DDC(82,5 mg, 0.400 mmol) and DMAP (12.2 mg, 0.100 mmol). The resultant was stirred for 16 hours at room temperature. In the same manner as that in Example 11, the title compound (193.1 mg, yield:78.9%) was obtained.

mp : 69.5°–71.0° C.

$[\alpha]_D^{25}$:+40.69° (C=1.504, $CH_2Cl_2$:MeOH=2 1)

IR γmax(cm$^{-1}$) : 3700–3130(OH), 3300(NH), 2930, 2860(CH), 1740(ester), 1660, 1540(amido), NMR(CDCl$_3$) 0.88(t,9H,JMeCH$_2$6.6 Hz,3MeCH$_2$), 1.25(m,68H,34CH$_2$), 1.43(d,3H,JMeCH5.9 Hz,MeC of Ala), 1.45(d,3H,JMeCH5.9 Hz,MeC of Lac), 1.60(m,6H,3MeCH$_2$), 1.99(s,3H,AcN), 2.19–2.66(m,8H,CH$_2$CH of Gln,3CH$_2$CO), 2.35[t,2H,JCH$_2$CH$_{27.7}$ Hz,CH$_2$CO of Gln), 3.69(s,3H,COOMe), 5.30(m,1H,H—3 of $C_{14}OC_{16}$), 6.05(d,1H,$J_{1,2}$2.9 Hz,H—1)

EXAMPLE 19

N-[2-0-{2-Acetamido-2,3-dideoxy-1-S-((3R)-3-hexadecaonyloxytetradecanoyl-1-thio-β-D-qlucopyranos-3-yl}-D-lactoyl]-L-alanyl-D-isoglutamine methylester The compound of the formula (III) wherein $R_1$ is 3-hexadecanoyloxytetradecanoylthio (586.6 mg, 0.580mmol) was dissolved in 80% acetic acid aqueous solution (12 ml), which was allowed to stand for an hour at 45° C. In the same manner as that in Example 4, the title compound 563.4 mg) was quantitatively obtained.

mp : 94.6°–95.8° C.

$[\alpha]_D^{25}$:+28 06(C=1.112, $CH_2Cl_2$.:MeOH=1:1)

IR γmax(cm$^{-1}$) : 3680–3130(OH), 3300(NH), 2940, 2870(CH), 1740(ester), 1650, 1550(amido)

NMR(CDCl$_3$) : 0.88(t,6H,JMeCH$_2$6.4 Hz,2MeCH$_2$), 1.27(m,40H,20CH$_2$), 1.37(d,3H,JMeCH7.0 Hz,MeC of Lac), 1.41[d,3H,JMeCH7.0 Hz,MeC of Ala), 1.60(m,4H,2MeCH$_2$), 1.91(s,3H,AcN), 1.91–2.02(m,1H,CHCH$_2$ of Gln), 2.21–2.90(m,6H,CH$_2$CO of Gln,2CH$_2$CO), 3.70(s,3H,COOMe), 4.05(t,1H,$J_{6a,6b}$,10.3 Hz,H-6a), 4.22–4.26(m,2H,CH of Lac and Ala), 4.34–4.39(m,1H,CH of Gln), 5.13[d,1H,Jl.210.6 Hz,H—1), 5.21–5.25(m,1H,H—3 of $C_{14}OC_{16}$)

EXAMPLE 20

N-[2-0-{2-Acetamido-2,3-dideoxy-6-0-octadecanoyl-1-S-((3R)-3-hexadecanoyloxytetradecanoyl)-1-thio-β-D-glucopyranos-3-yl}-D-lactoyl]-L-alanYl-D-isoglutamine methylester The compound of the formula (I') wherein $R_1$ is 3-hexadecanoyloxytetradecanoylthio(340.0 mg, 0.350mmol) was dissolved in a mixture of dry dioxane (4.0 ml) and dry DMF(1.5 ml). To the solution were added octadecanoic acid(129.4 mg, 0.455mmol), DCC(144.4 mg, 0.700mmol) and DMAP(21.4 mg, 0.175mmol). The resultant was stirred for 3 hours at room temperature. In the same manner as that in Example 14, the title compound (203.1mg, yield : 46.8%) was obtained.

mp : 171.2°–172.8° C.

$[\alpha]_D^{25}$:+17.01° (C=0.723, $CH_2Cl_2$:MeOH=2 1)

IR γmax(cm$^{-1}$):3320, 2370(NH, OH), 2920, 2850(CH), 1740(ester), 1650, 1540(amido)

NMR(CDCl$_3$) 0.87(t,9H,JMeCH5.3 Hz,3MeCH$_2$), 1.25(m,70H,35CH$_2$), 1.39(d,3H,JMeCH6.6 Hz,MeC of Ala), 1.58(m,6H,3MeCH$_2$), 1.94(s,3H,AcN), 2.22–2.91(m,2H,CH$_2$CO of Gln), 2.32(t,2H,JCH$_2$CH$_2$7.7 Hz,CH$_2$CO of Gln), 3.69(s,3H,COOMe), 5.13(d,1H,$J_{1,2}$11.0 Hz,H—1), 5.11–5.20(m,1H,H—3 of $C_{14}$—O—$C_{16}$)

EXAMPLE 21

N-[2-0-{2-Acetamido-2,3-dideoxy-1-0-((3R)-3-octadecanoyloxytetradecanoyl)-α-D-glucopyranos-3-yl}-D-lactoyl]-L-alanyl-D-isoglutamine methylester The compound of the formula (III) wherein Rl is 3-octadecanoyloxytetradecanoyloxy(388.9 mg, 0.380mmol) was dissolved in 80% acetic acid aqueous solution(15 ml), which was allowed to stand for 2 hours at 45° C. In the same manner as that in Example 4, the title compound (373.7 mg) was quantitatively obtained(373.7 mg).

mp : 187°–188.5° C.

$[\alpha]_D^{25}$:+47.11° (C=0.900, $CH_2Cl_2$:MeOH=1:1)

IR γmax(cm$^{-1}$) : 3700–3100(OH), 3300(NH), 2910, 2850(CH), 1740(ester), 1650, 1540(amido)

NMR(CDCl$_3$):0.88[t,9H,JMe$_1$CH$_2$7.0 Hz,3MeCH$_2$), 1.25[m,44H,22CH$_2$), 1.41(d,3H,JMeCH7.8 Hz,MeC of Ala), 1.44[d,3H,JMeCH7.8 Hz,MeC of Lac), 1.99(s,3H,AcN), 1.94–2.04(m,2H,CH$_2$CH of Gln), 2.30(t,2H,JCH$_2$CH$_2$8.0$_z$,CH$_2$CO of Gln), 2.27–2.46(m,6H,3CH$_2$CO), 3.70(s,3H,COOMe), 5.30(m,1H,H—3 of $C_{14}OC_{18}$), 6.05(d,1H,$J_{12}$7.8 Hz,H—1)

EXAMPLE 22

N-[2-0-{2-Acetamido-2,3-dideoxy-6-0-octadecanoyl-1-0-((3R)-3-octadecanoyloxytetradecanoyl)-α-D-glucopyranos-3-yl}-D-lactoyl-L-alanyl-D-isoglutamine methylester The compound of the formula (I') wherein $R_1$ is 3-octadecanoyloxytetradecanoyloxy(177,0 mg, 0.18mmol) was in a mixture of dry dioxane(3.0 ml) and dry DMF(1.0 ml). To the solution were added octadecanoic acid(66.6 mg, 0.234mmol), DCC(74.3 mg, 0.360mmol) and DMAP(11.0 mg, 0.090mmol). The resultant was stirred for 16 hours at room temperature. In the same manner as that in Example 11, the title compound (164.0 mg, 72.8%) was mp : 106°-108.5° C.

$[\alpha]_D^{25}$: +38.46° (C=0.624, $CH_2Cl_2$:MeOH = 1:1)

IR $\gamma$max(cm$^{-1}$) : 3700-3150(H), 3300(NH), 2930, 2860(CH), 1740(ester), 1660, 1540(amido)

NMR(CDCl$_3$):0.88(t,9H,JCH$_2$CH$_2$66 Hz,3MeCH$_2$), 1.25(m,72H,36CH$_2$), 1.43(d,3H,JMeCH6.2 Hz,MeC of Lac), 1.59(m,6H,3MeCH$_2$), 1.99(s,3H,AcN), 2.01-2.20(m,8H,CH$_2$CH of Gln,3CH$_2$CO), 2.30(t,2H,JCH$_2$CH$_2$7.7 Hz,CH$_2$CO of Gln), 3.69(s,3H,COOMe), 5.30(m,1H,H—3 of $C_{14}OC_{18}$), 6.05(d,1H,J$_{1,2}$3.0 Hz,H—1)

EXAMPLE 23

N-[2-0-{2-Acetamido-2,3-dideoxy-1-S-((3R)-3-octadecanoyloxytetradecanoyl)-1-thio-β-D-glucopyranos-3-yl}-D-lactoyl]-L-alanyl-D-isoglutamine methylester The compound of the formula (III wherein $R_1$ is 3-octadecanoyloxytetradecanoylthio(634.1mg, 0.610mmol) was dissolved in 80% acetic acid acqueous solution 15 ml , which was allowed to stand for an hour at 45° C. In the same manner as that in Example 4, the title compound (609.6 mg) was quantitatively obtained.

mp : 112.5°-113.8° C.

$[\alpha]_D^{25}$: +24.62° (C=0.600, $Ch_2Cl_2$ MeOH = 1:1)

IR $\gamma$max(cm$^{-1}$) : 3400-3100(OH), 3260(NH}, 2910, 2850(CH), 1740(ester), 1640, 1530(amido)

NMR(CDCl$_3$) 0.88(t,6H,JMeCH$_2$,4.0 Hz,2MeCH$_2$), 1.25(m,44H,22CH$_2$), 1.33(d,3H,JMeCH7.3 Hz,MeC of Lac), 1.36(d,3H,JMeCH7.3 Hz,MeC of Ala), 1.58(m,4H,2MeCH$_2$), 1.92(s,3H,AcN), 1.91-2.04(m,2H,CHCH$_2$ of Gln), 2.26(m,6H,CH2CO of Gln,2CH$_2$CO), 3.69[s,3H,COOMe), 4.02-4.09(t,1H,-J$_{6a,6b}$8.7 Hz,H-6a), 4.28(m,1H,CH of Gln), 5.08(d,1H,J$_{1,2}$4.0 Hz,H—1), 5.21{m,1H,H—3 of $C_{14}$—O—$C_{18}$)

EXAMPLE 24

N-[2-0-{2-Acetamido-2,3-dideoxy-6-0-octadecanoyl-1-S-((3R)-3-octadecanoyloxytetradecanoyl)-1-thio-β-D-glucopyranos-3-yl}-D-lactoyl]-L-alanyl-D-isoglutamine The compound of the formula (I') wherein $R_1$ is 3-octadecanoyloxytetradecanoylthio(400.0 mg, 0.400mmol) was dissolved in a mixture of dry dioxane (4.0 ml) and dry DMF(1.5 ml). To the solution were added octadecanoic acid(147.9 mg, 0.520mmol , DCC(165.1mg, 0.800mmol}and DMAP(24.4 mg, 0.200mmol), and the resultant was stirred for 3.5 hours at room temperature. In the same manner as that in Example 14, the title compound (258.6 mg, yield 51.0%) was obtained.

mp : 123.1°-124.5° C. $[\alpha]_D^{25}$:+17.01° (C=0.723, $CH_2Cl_2$ MeOH=2:1)

IR $\gamma$max(cm$^{-1}$) 3650-3150(OH), 3300(NH), 2930, 2850[CH], 1730(ester), 1650, 1550(amido)

NMR(CDCl$_3$) 0.88(t,9H,JMeCH$_2$5.5 Hz,3MeCH$_2$), 1.25[m,74H,37CH$_2$), 1.34[d,3H,JMeCH6.6 Hz,MeC of Ala), 1.44-1.67(m,6H,3MeCH$_2$), 1.85(s,3H,AcN), 2.17-2.79(m,2H,CH$_2$CHof Gln), 2.31(t,2H,JCHh$_2$CH$_2$8.4 Hz,CH$_2$CO of Gln), 3.70(s,3H,COOMe), 5.10[d,1H,J$_{1,2}$10 6 Hz,H—1), 5.14(m,1H,H—3 of $C_{14}OC_{18}$)

EXAMPLE 25

N-[2-0-{2-Acetamido-2,3-dideoxy-1-0-((3R)-3-tetradecanoyloxytetradecanoyl}-α-D-glucopyranos-3-yl}-D-lactoyl]-L-alanyl-D-isoglutamine methylester The compound of the formula (III wherein $R_1$ is 3-tetracosanoyloxytetradecanoyloxy[465.2 mg, 0.420mmol) was dissolved in 80% acetic acid aqueous solution (15 ml), which was allowed to stand for an hour at 45° C. In the same manner as that in Example 4, the title compound(448.3 mg) was quantitatively obtained.

mp : 183.5°-185° C.

$[\alpha]_D^{25}$:+34.13° (C=0.920, $CH_2Cl_2$:MeOH=2:1)

IR$\gamma$max(cm$^{-1}$): 3700-3120(OH), 3300(NH), 2930, 2850(CH), 1740(ester), 1660, 1540(amido)

NMR(CDCl$_3$) 0.89(t,9H,JMeCH$_2$6.6 Hz,3MeCH$_2$), 1.25(m,56H,28CH$_2$), 1.41(d,3H,JMeCH6.9 Hz,MeC of Ala), 1.44(d,3H,JMeCH6.9 Hz,MeC of Lac), 1.60(m,6H,3MeCH$_2$), 1.99(s,3H,AcN), 1.94-2.01(m,2H,CH$_2$CHof Gln), 2.20-2.39(m,6H,3CH$_2$CO), 2.29(t,2H,JCH$_2$CH$_2$13 Hz,CH$_2$OO of Gln), 3.69(s,3H,COOMe), 5.30(m,1H,H—3 of $C_{14}OC_{24}$), 6.05(d,1H,J$_{1,2}$2.9 Hz,H—1)

EXAMPLE 26

N-[2-0-{2-Acetamido-2,3-dideoxy-6-0-octadecanoyl-1-0-((3R)-3-tetradecanoyloxytetradecanoyl)-α-D-glucopyranos-3-yl}-D-lactoyl]-L-alanyl-D-isogluatmine methylester The compound of the formula (I') wherein $R_1$ is 3-tetracosanoyloxytetradecanoyloxy (234.8 mg, 0.220 mmol) was dissolved in a mixture of dry dioxane (3.0 ml) and dry DMF(1.0 ml). To the solution were added octadecanoic acid (81.3 mg, 0.286 mmol), DCC (90.8 mg, 0.440 mmol) and DMAP(13.4 mg, 0.110 mmol), and the resultant was stirred for 12 hours at room temperature. In the same manner as that in Example 11, the title compound (200.7 mg, yield:68.3%) was obtained.

mp : 66.5°-68° C.

$[\alpha]_D^{25}$: +34.11° (c=0.680, $CH_2Cl_2$:MeOH = 1:1)

IR $\gamma$max(cm$^{-1}$) : 3700-3100(OH) 3300 NH), 2930, 2850(CH), 1760(ester), 1660, 1540(amido)

NMR(CDCl$_3$) : 0.88(t,9H,JCH$_2$CH$_2$6.6 Hz,3MeCH$_2$), 1.25(m,88H,44CH$_2$), 1.43(d,3H,JMeOH6.6 Hz,MeC of Ala), 1.44(d,3H,JMeOH7.0 Hz,MeC of Lac), 1.61(m,6H,3MeCH$_2$), 2.00(m,8H,CH$_2$CH of Gln,3CH$_2$CO), 1.99(s,3H,AcN), 2.33(t,2H,JCH$_2$CH$_2$4 2 Hz,CH$_2$CO of Gln). 3.65(s,3H,COOMe), 4.20(q,1H,JMe$_1$CH,Hz,MeCH of Ala), 5.29(m,1H,H—3 of $C_{14}OC_{24}$), 6.04(d,1H,J$_{1,2}$33 Hz,1-H)

EXAMPLE 27

N-[2-0-{2-Acetamido-2,3-dideoxy-1-S-((3R)-3-tetracosanoyloxytetradecanoyl]-1-thio-$\beta$-D-glucopyranos-3-yl}-D-lactoyl]-L-alanyl-D-isoglutamine methylester The compound of the formula (III) wherein $R_1$ is 3-tetracosanoyloxytetradecanoylthio (617.9 mg, 0.550mmol) was dissolved in 80% acetic acid aqueous solution (12 ml), which was allowed to stand for an hour at 45° C. In the same manner as that in Example 4, the title compound 595.9 mg}was quantitatively obtained.

mp : 168.5°–170.1° C.

$[\alpha]_D^{25}$: +5.18° (C=0.772, $CH_2Cl_2$:MeOH=1:1)

IR $\gamma$max(cm$^{-1}$) : 3500–3200(OH), 3280(NH), 2910, 2850(CH), 1720(ester), 1630, 1540(amido)

NMR(CDCl$_3$) 0.88(t,6H,JMe$_1$CH$_2$ Hz,2MeCH$_2$) 1.25(m,56H,28CH$_2$), 1.30(d,3H,JMeCH8.3 Hz,MeC of Lac), 1.34(d,3H,JMeCH7.5 Hz,MeC of Ala), 1.58(m,4H,2MeCH$_2$), 1.97–1.91(m,2H,2MeCH$_2$), 1.94(s,3H,AcN), 2.25(m,6H,CHCH$_2$ of Gln), 3.69(s,3H,COOMe), 4.05(t,1H,J$_{6a,6b}$10.1 Hz,H—6a), 4.24–4.28(m,1H,CH of Gln), 5.09(d,1H,J$_{1,2}$10.8 Hz,H—1), 5.13–5.19(m,1H,H—3 of C$_{14}$—O—C$_{24}$)

EXAMPLE 28

N-[2-0-{2-Acetamido-2,3-dideoxy-6-0-octadecanoyl-1-S-((3R)-3-tetracosanoyloxytetradecanoyl)-1-thio-$\beta$-D-glucopyranos-3-Yl}-D-lactoyl]-L-alanyl-D-isoglutamine methylester The compound of the formula (I') wherein $R_1$ is 3-tetracosanoyloxytetradecanoylthio (411.8 mg, 0.380mmol) was dissolved in a mixture of dry dioxane 4.0 ml) and dry DMF (1.5 ml). To the solution were added octadeconoic acid (140.5 mg, 0.494mmol), DCC(156.8 mg, 0.760mmol) and DMAP (23.2 mg, 0.190mmol), and the resultant was stirred for 3 hours at room temperature. In the same manner as that in Example 14, the title compound (223.5 mg, yield:43.5%) was obtained.

mp : 147.5°–149.0° C.

$[\alpha]_D^{25}$: +17.40° ( C=0.632, $CH_2Cl_2$:MeOH=1:1)

IR $\gamma$max(cm$^{-1}$): 3600–32 00(OH), 3300{NH}, 2950, 2880(CH), 1750(ester), 1660, 1560(amido)

NMR(CDCl$_3$) 0.88(t,9H,JMeCH5.5 Hz,3MeCH$_2$), 1.25(m,86H,43CH$_2$), 1.35(d,3H,JMeCH6.3 Hz,MeC of Ala), 1.57(m,6H,3MeCH$_2$), 1.90(s,3H,AcN), 2.05–2.90(m,2H,CH$_2$CH of Gln), 2.35(t,2H,JCH$_2$CH$_2$7.8 Hz,CH$_2$CO of Gln), 3.68(s,3H,COOMe), 5.13{d,1H,J$_{1,2}$11.0 Hz,H—1), 5.15(m,1H,H—3 of C$_{14}$OC$_{24}$)

Pharmacological activities of the compounds of the present invention are shown as follows.

(1) Hepatitis-vaccine enhancing activity (adjuvant activity)

A compound of the present invention was dissolved in lipidmicrosphere (1 mg/ml). On the other hand, a solution of hepatitis B virus surface antigen (HBs) in physiological saline was prepared (50 $\mu$g/ml). The above solutions in equal amounts were mixed to prepare a test solution. A control solution was prepared by the exclusion of the compound of the present invention from said test solution. A mixture of a suspension of aluminium hydroxide gel in physiological saline (1 mg/ml) and said hepatitis vaccine preparation in equal amounts was prepared as another control solution. The test solution (0.2 ml) was intraperitoneally administered to each mouse in one group consisting of seven female CDF$_1$ mice.

Blood samples were collected from the fundus ocluli vein of each mouse every week after the administration and then centrifuged to obtain serums. Three weeks after the administration, 0.2 ml of the test liquid was intraperitoneally administered again to each mouse for secondary stimulation. Then blood collecting was conducted every week to obtain serums after the application of the secondary stimulation, in the same manner as that described above.

The amount of the IgG antibodies against the hepatitis B virus surface antigens (HBs) in the serums thus obtained was determined with an ELISA method. The results are shown in Table 1.

TABLE 1

| Test material | 1 W | 2 W | 3 W | 4 W | 5 W |
|---|---|---|---|---|---|
| *Adjuvant activities on heptatis B virus surface antigens - Experiment 1* | | | | | |
| Anti HBs serum antigen value (average value ± S.D.) O.D 415 nm 5000-fold dilution | | | | | |
| Example 1 | 0.001 ± 0.001 | 0.018 ± 0.000 | 0.074 ± 0.002 | 0.815 ± 0.011 | 0.843 ± 0.005 |
| 2 | 0 | 0.023 ± 0.000 | 0.076 ± 0.001 | 0.975 ± 0.008 | 0.930 ± 0.004 |
| 3 | 0 | 0.027 ± 0.001 | 0.064 ± 0.003 | 0.631 ± 0.006 | 0.692 ± 0.009 |
| 4 | 0 | 0.073 ± 0.001 | 0.111 ± 0.007 | 0.848 ± 0.009 | 0.935 ± 0.022 |
| 5 | 0.001 ± 0.001 | 0.021 ± 0.001 | 0.048 ± 0.001 | 0.643 ± 0.013 | 0.490 ± 0.009 |
| 6 | 0 | 0.020 ± 0.002 | 0.069 ± 0.001 | 0.477 ± 0.005 | 0.529 ± 0.005 |
| 7 | 0 | 0.016 ± 0.003 | 0.071 ± 0.004 | 0.426 ± 0.000 | 0.470 ± 0.010 |
| 8 | 0 | 0.067 ± 0.003 | 0.114 ± 0.002 | 0.897 ± 0.012 | 0.845 ± 0.016 |
| 9 | 0.014 ± 0.002 | 0.092 ± 0.003 | 0.149 ± 0.001 | 0.681 ± 0.012 | 0.702 ± 0.006 |
| 10 | 0 | 0.061 ± 0.002 | 0.114 ± 0.003 | 0.778 ± 0.024 | 0.878 ± 0.009 |
| 11 | 0.010 ± 0.002 | 0.083 ± 0.002 | 0.124 ± 0.003 | 0.602 ± 0.009 | 0.716 ± 0.020 |
| 12 | 0.007 ± 0.003 | 0.109 ± 0.002 | 0.111 ± 0.001 | 0.608 ± 0.021 | 0.695 ± 0.021 |
| 13 | 0 | 0.081 ± 0.003 | 0.126 ± 0.003 | 0.635 ± 0.011 | 0.742 ± 0.016 |
| 14 | 0 | 0.071 ± 0.000 | 0.104 ± 0.003 | 0.784 ± 0.022 | 0.846 ± 0.024 |
| 15 | 0 | 0.085 ± 0.002 | 0.129 ± 0.001 | 0.788 ± 0.008 | 0.905 ± 0.020 |
| 16 | 0 | 0.079 ± 0.004 | 0.103 ± 0.004 | 0.850 ± 0.008 | 0.903 ± 0.021 |
| Aluminum hydroxide gel | 0 | 0 | 0 | 0.027 ± 0.001 | 0.040 ± 0.001 |
| Control | 0 | 0 | 0 | 0.097 ± 0.006 | 0.123 ± 0.001 |
| *Adjuvant activities on heptatis B virus surface antigens - Experiment 2* | | | | | |
| Anti HBs serum antigen value (average value ± S.D.) | | | | | |

TABLE 1-continued

| Test material | 1 W | 2 W | 3 W | 4 W | 5 W |
|---|---|---|---|---|---|
| | | O.D 415 nm | 2000-fold dilution | | |
| Example 17 | 0.001 ± 0.004 | 0.026 ± 0.001 | 0.051 ± 0.001 | 0.642 ± 0.021 | 0.615 ± 0.021 |
| 18 | 0 | 0.035 ± 0.007 | 0.050 ± 0.004 | 0.481 ± 0.006 | 0.375 ± 0.008 |
| 19 | 0 | 0.023 ± 0.000 | 0.042 ± 0.001 | 0.536 ± 0.011 | 0.521 ± 0.012 |
| 20 | 0.002 ± 0.001 | 0.044 ± 0.005 | 0.056 ± 0.003 | 0.814 ± 0.018 | 0.708 ± 0.002 |
| 21 | 0.006 ± 0.004 | 0.038 ± 0.000 | 0.058 ± 0.007 | 0.517 ± 0.006 | 0.498 ± 0.011 |
| 22 | 0.005 ± 0.004 | 0.036 ± 0.007 | 0.053 ± 0.001 | 0.294 ± 0.006 | 0.254 ± 0.002 |
| 23 | 0.004 ± 0.001 | 0.051 ± 0.003 | 0.092 ± 0.004 | 0.639 ± 0.003 | 0.626 ± 0.008 |
| 24 | 0.007 ± 0.001 | 0.034 ± 0.001 | 0.050 ± 0.000 | 0.579 ± 0.007 | 0.513 ± 0.011 |
| 25 | 0.004 ± 0.002 | 0.021 ± 0.001 | 0.031 ± 0.004 | 0.402 ± 0.011 | 0.434 ± 0.021 |
| 26 | 0.001 ± 0.006 | 0.015 ± 0.006 | 0.032 ± 0.008 | 0.192 ± 0.002 | 0.163 ± 0.004 |
| 27 | 0.003 ± 0.003 | 0.031 ± 0.002 | 0.052 ± 0.000 | 0.580 ± 0.016 | 0.573 ± 0.013 |
| 28 | 0.005 ± 0.003 | 0.062 ± 0.004 | 0.086 ± 0.004 | 0.611 ± 0.018 | 0.543 ± 0.029 |
| Aluminum hydroxide gel | 0 | 0.002 ± 0.002 | 0.006 ± 0.004 | 0.196 ± 0.003 | 0.227 ± 0.001 |
| Control | 0 | 0.017 ± 0.000 | 0.022 ± 0.001 | 0.267 ± 0.004 | 0.232 ± 0.004 |

(2) Influenza HA vaccine enhancing activity (adjuvant activity)

A compound of the present invention was dissolved in lipidmicrosphere (1mg/ml). On the other hand, a solution of influenza HA vaccine (B/nagasaki/1/87 strain) in physiological saline was prepared (100 ccA/ml). The above solutions in equal amounts were mixed to prepare a test solution. A control solution was made by the exclusion of the compound of the present invention from said test liquid. A mixture of a suspension of aluminium hydroxide gel in physiological saline(1mg/ml) and said influenza HA vaccine preparation in equal amounts was prepared as another control liquid. The test solution (0.2 ml) was intraperitoneally administered to each mouse in one group consisting of seven female $CDF_1$ mice.

Blood samples were collected from the fundus oculi vein of each mouse every week after the administration and then centrifuged to obtain serums. Three weeks after the aministration, 0.2 ml of the test liquid was intraperitoneally administered again to each mouse for secondary stimulation. Then, blood collecting was conducted every week to obtain serums after the application of the secondary stimulation, in the same manner as that described above.

The amount of the IgG antibodies against the influenza HA vaccine (B/Nagasaki/1/87 strain) in the serums thus obtained was determined with an ELISA method. The results are shown in Table 2.

TABLE 2

| Test material | 1 W | 2 W | 3 W | 4 W | 5 W |
|---|---|---|---|---|---|
| | ‡Adjuvant activities on influenza HA vaccines - Experiment 1 | | | | |
| | Anti HA serum antigen value (average value ± S.D.) O.D 415 nm 5000-fold dilution | | | | |
| Example 1 | 0.007 ± 0.003 | 0.174 ± 0.003 | 0.232 ± 0.003 | 1.243 ± 0.036 | 1.201 ± 0.002 |
| 2 | 0.003 ± 0.001 | 0.172 ± 0.004 | 0.420 ± 0.005 | 0.447 ± 0.029 | 1.418 ± 0.035 |
| 3 | 0.009 ± 0.000 | 0.182 ± 0.003 | 0.292 ± 0.004 | 0.122 ± 0.020 | 1.140 ± 0.013 |
| 4 | 0.004 ± 0.001 | 0.215 ± 0.001 | 0.381 ± 0.004 | 1.204 ± 0.012 | 1.150 ± 0.016 |
| 5 | 0 | 0.091 ± 0.002 | 0.377 ± 0.001 | 1.037 ± 0.027 | 1.068 ± 0.004 |
| 6 | 0.001 ± 0.001 | 0.013 ± 0.002 | 0.259 ± 0.004 | 1.025 ± 0.013 | 1.159 ± 0.013 |
| 7 | 0.001 ± 0.001 | 0.112 ± 0.003 | 0.286 ± 0.001 | 1.039 ± 0.010 | 1.128 ± 0.026 |
| 8 | 0.001 ± 0.001 | 0.105 ± 0.005 | 0.246 ± 0.004 | 1.246 ± 0.019 | 1.267 ± 0.023 |
| 9 | 0.019 ± 0.002 | 0.168 ± 0.005 | 0.392 ± 0.006 | 1.342 ± 0.005 | 1.329 ± 0.026 |
| 10 | 0.005 ± 0.001 | 0.153 ± 0.003 | 0.280 ± 0.000 | 1.149 ± 0.018 | 1.203 ± 0.014 |
| 11 | 0 | 0.073 ± 0.000 | 0.160 ± 0.005 | 1.059 ± 0.016 | 1.050 ± 0.003 |
| 12 | 0 | 0.105 ± 0.004 | 0.176 ± 0.002 | 1.039 ± 0.015 | 1.050 ± 0.008 |
| 13 | 0 | 0.088 ± 0.004 | 0.140 ± 0.001 | 0.868 ± 0.010 | 0.824 ± 0.002 |
| 14 | 0 | 0.110 ± 0.003 | 0.186 ± 0.007 | 0.974 ± 0.006 | 0.954 ± 0.002 |
| 15 | 0.007 ± 0.000 | 0.119 ± 0.005 | 0.218 ± 0.006 | 1.249 ± 0.013 | 1.262 ± 0.017 |
| 16 | 0.001 ± 0.001 | 0.145 ± 0.004 | 0.257 ± 0.010 | 1.251 ± 0.010 | 1.262 ± 0.026 |
| Aluminum hydroxide gel | 0 | 0 | 0 | 0.162 ± 0.004 | 1.263 ± 0.007 |
| Control | 0 | 0 | 0 | 0.410 ± 0.004 | 0.502 ± 0.008 |
| | *Adjuvant activities on influenza HA vaccines - Experiment 2 | | | | |
| | Anti HA serum antigen value (average value ± S.D.) O.D 415 nm 8000-fold dilution | | | | |
| Example 17 | 0.010 ± 0.002 | 0.122 ± 0.006 | 0.191 ± 0.001 | 0.611 ± 0.017 | 0.696 ± 0.014 |
| 18 | 0 | 0.052 ± 0.004 | 0.075 ± 0.001 | 0.370 ± 0.005 | 0.360 ± 0.001 |
| 19 | 0 | 0.125 ± 0.003 | 0.187 ± 0.001 | 0.872 ± 0.002 | 0.936 ± 0.006 |
| 20 | 0.001 ± 0.001 | 0.071 ± 0.001 | 0.110 ± 0.008 | 0.840 ± 0.011 | 0.857 ± 0.023 |
| 21 | 0 | 0.060 ± 0.001 | 0.097 ± 0.002 | 0.748 ± 0.003 | 0.758 ± 0.012 |
| 22 | 0.001 ± 0.004 | 0.065 ± 0.001 | 0.100 ± 0.003 | 0.411 ± 0.009 | 0.492 ± 0.002 |
| 23 | 0.008 ± 0.005 | 0.096 ± 0.001 | 0.183 ± 0.004 | 0.949 ± 0.006 | 1.030 ± 0.003 |
| 24 | 0.006 ± 0.001 | 0.085 ± 0.005 | 0.113 ± 0.007 | 0.771 ± 0.003 | 0.791 ± 0.004 |

TABLE 2-continued

| Test material | 1 W | 2 W | 3 W | 4 W | 5 W |
|---|---|---|---|---|---|
| 25 | 0.009 ± 0.001 | 0.109 ± 0.002 | 0.149 ± 0.004 | 0.623 ± 0.019 | 0.719 ± 0.021 |
| 26 | 0.004 ± 0.003 | 0.038 ± 0.001 | 0.054 ± 0.001 | 0.208 ± 0.001 | 0.206 ± 0.002 |
| 27 | 0 | 0.110 ± 0.003 | 0.161 ± 0.003 | 0.751 ± 0.004 | 0.805 ± 0.008 |
| 28 | 0.008 ± 0.004 | 0.041 ± 0.004 | 0.061 ± 0.001 | 0.787 ± 0.018 | 0.779 ± 0.024 |
| Aluminum hydroxide gel | 0 | 0 | 0 | 0.152 ± 0.008 | 0.181 ± 0.008 |
| Control | 0 | 0.046 ± 0.001 | 0.071 ± 0.004 | 0.380 ± 0.004 | 0.388 ± 0.005 |

(3) Activation of macrophages (an effect which inhibits the growth of tumor cells)

A compound of the present invention was dissolved in lipidmicrosphere to obtain a solution in a concentration of 500μg/ml, and 0.2 ml of such solution was intraperitoneally administered to each mouse in one group consisting of seven female $CDF_1$ mice. Intraperitoneal macrophages obtained three days after the administration and L-1210 mouse leukemia cells were mixed in the ratio of cell numbers of 20:1, respectively. Two hundred μl of the mixture was placed in each well of one sheet of 96 well microtiter plate. After 72 hours, the increase of the cell number in each well was determined by a MTT assay method. The ratio of the cell number for the mixture of the L-1210 cells and the macrophage relative to the cell number for the L-1210 cells only (growth inhibitory ratio) was determined, and the results are shown in Table 3.

TABLE 3

| Test material | Growth inhibitory ratio of L-1210 mouse leukemia cells (%) |
|---|---|
| Example 1 | 40.0 |
| 2 | 41.3 |
| 3 | 42.6 |
| 4 | 45.2 |
| 5 | 57.8 |
| 6 | 63.0 |
| 7 | 90.2 |
| 8 | 57.9 |
| 9 | 58.5 |
| 10 | 76.6 |
| 11 | 59.7 |
| 12 | 79.0 |
| 13 | 39.7 |
| 14 | 96.4 |
| 15 | 87.5 |
| 16 | 76.3 |
| Control | 9.1 |

What is claimed is:

1. In the formula: insert a bond between the ring and the acetamido group as circled below:

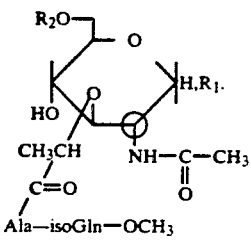

2. A compound of claim 1 wherein $R_3$ is 2-tetradecyl-hexadecanoyl.

3. A compound of claim 1 wherein $R_3$ is (3R)-3-tetradecanoyloxytetradecanoyl.

4. A compound of claim 1 wherein $R_3$ is (3R)-3-hexadecanoyloxytetradecanoyl.

5. A compound of claim 1 wherein $R_2$ is hydrogen atom.

6. A compound of claim 1 wherein $R_2$ is tetradecanoyl.

7. A compound of claim 1 wherein "Ala" is L-alanine residue, and "isoGln" is D-isoglutamine residue.

8. A compound of claim 1 which is

N-[2-0-{2-acetamido-2,3-dideoxy-1-0-[2-tetradecylhexadecanoyl)-α-D-glucopyranos-3-yl}-D-lactoyl]-L-alanyl-D-isoglutamine methylester, N-[2-0-{2-acetamido-2,3-dideoxy-6-0-decanoyl-1-0-(2-tetradecylhexadecanoyl)-α-D-glucopyranos-3-yl}-D-lactoyl]-L-alanyl-D-isoglutamine methylester, N-[2-0-{2-acetamido-2,3-dideoxy-6-0-tetradecanoyl-1-0-(2-tetradecylhexadecanoyl)-α-D-glucopyranos-3-yl}-D-lactoyl]-L-alanyl-D-isoglutamine methylester, N-[2-0-{2-acetamido-2,3-dideoxy-6-0-octadecanoyl-0-(2-tetradecylhexadecanoyl)-α-D-glucopyranos-3-yl}-D-lactoyl]-L-alanyl-D-isoglutamine methylester, N-[2-0-{2-acetamido-2,3-dideoxy-1-S-(2-tetradecylhexadecanoyl)-1-thio-8-D-glucopyranos-3-yl}-D-lactoyl]-L-alanyl-D-isoglutamine methylester, N-[2-0-{2-acetamido-2,3-dideoxy-6-0-decanoyl-1-S-(2-tetradecylhexadecanoyl)-1-thio-β-D-glucopyranos-3-yl}-D-lactoyl]-L-alanyl-D-isoglutamine methylester, N-[2-0-{2-acetamido-2,3-dideoxy-6-0-tetradecanoyl-1-S-(2-tetradecylhexadecanoyl)-1-thio-β-D-glucopyranos-3-yl}-D-lactoyl]-L-alanyl-D-isoglutamine methylester, N-[2-0-{2-acetamido-2,3-dideoxy-6-0-octadecanoyl-1-S-(2-tetradecylhexadecanoyl)-1-thio-β-D-glucopyranos-3-yl}-D-lactoyl]-L-alanyl-D-isoglutamine methylester, N-[2-0-{2-acetamido-2,3-dideoxy-1-0-((3R)-3-tetradecanoyloxytetradecanoyl)-α-D-glucopyranos-3-yl}-D- 0 lactoyl]-L-alanyl-D-isoglutamine methylester, N-[2-0-{2-acetamido-2,3-dideoxy-6-0-decanoyl-1-0-((3R)-3-tetradecanolyloxytetradecanoyl)-α-D-glucopyranos-3-yl)-D-lactoyl]-L-alanyl-D-isoglutamine methylester, N-[2-0-{2-acetamido-2,3-dideoxy-6-0-tetradecanoyl-1-0-((3R)-3-tetradecanoyloxytetradecanoyl)-α-D-gluco pyranos-3-yl}-D-lactoyl]-L-alanyl-D-isoglutamine methylester, N-[2-0-{2-acetamido-2,3-dideoxy-6-0-octadecanoyl-1-0-((3R)-3-tetradecanoyloxytetradecanoyl)-α-D-glucopyranos-3-yl}-D-lactoyl]-L-alanyl-D-isoglutamine methylester, N-[2-0-{2-acetamido-2,3-dideoxy-1-S-((3R)-3-tetradecanoyloxytetradecanoyl)-1-thio-β-D- glucopyranos-3-yl}-D-lactoyl]-L-alanyl-D-isoglutamine methylester,

N-[2-0-{2-acetamido-2,3-dideoxy-6-0-decanoyl-1-S-((3R)-3-tetradecanoyloxytetradecanoyl)-1-thio-β-D-glucopyranos-3-yl}-D-lactoyl]-L-alanyl-D-isoglutamine methylester, N-[2-0-{2-acetamido-2,3-dideoxy-6-0-tetradecanoyl-1-S-((3R)-3-tetradecanoyloxytetradecanoyl)-1-thio-β-D-glucopyranos-3-yl}-D-lactoyl]-L-alanyl-D-isoglutamine methylester, N-[2-0-{2-acetamido-2,3-dideoxy-6-0-octadecanoyl-1-S-((3R)-3-tetradecanoyloxytetradecanoyl)-1-thio-β-D-glucopyranos-3-yl}-D-lactoyl]-L-alanyl-D-isoglutamine methylester, N-[2-0-{2-acetamido-2,3-dideoxy-1-0-((3R)-3-hexadecanoyloxytetradecanoyl)-α-D-glucopyranos-3-yl}-D-lactoyl]-L-alanyl-D-isoglutamine methylester, N-[2-0-{2-acetamido-2,3-dideoxy-1-0-((3R)-3-hexadecanoyloxytetradecanoyl)-6-0-octadecanoyl-α-D-glucopyranos-3-yl}-D-lactoyl]-L-alanyl-D-isoglutamine methylester, N-[2-0-{2-acetamido-2,3-dideoxy-1-S-((3R)-3-hexadecanoyloxytetradecanoyl)-1-thio-β-D-glucopyranos-3-yl}-D-lactoyl]-L-alanyl-D-isoglutamine methylester, N-[2-0-{2-acetamido-2,3-dideoxy-1-S-((3R)-3-hexadecanoyloxytetradecanoyl)-6-0-octadecanoyl-1-thio-β-D-glucopyranos--3-yl}-D-lactoyl]-L-alanyl-D-isoglutamine methylester, N-[2-0-{2-acetamido-2,3-dideoxy-1-0-((3R)-3-octadecanoyloxytetradecanoyl)-α-D-glucopyranos-3-yl}-D-lactoyl]-L-alanyl-D-isoglutamine methylester, N-[2-0-{2-acetamido-2,3-dideoxy-6-0-octadecanoyl-1-0-((3R)-3-octadecanoyloxytetradecanoyl)-α-D-glucopyranos-3-yl}-D-lactoyl]-L-alanyl-D-isoglutamine methylester, N-[2-0-{2-acetamido-2,3-dideoxy-1-S-((3R)-3-octadecanoyloxytetradecanoyl)-1-thio-β-D-glucopyranos-3-yl}-D-lactoyl]-L-alanyl-D-isoglutmine methylester, N-[2-0-{2-acetamido-2,3-dideoxy-6-0-octadecanoyl-1-S-((3R)-3-octadecanoyloxytetradecanoyl)-1-thio-β-D-glucopyranos-3-yl}-D-lactoyl]-L-alanyl-D-isoglutamine methylester, N-[2-0-{2-acetamido-2,3-dideoxy-1-0-({3R)-3-tetracosanoyloxytetradecanoyl)-α-D-glucopyranos-3-yl}-D-lactoyl]-L-alanyl-D-isoglutamine methylester, N-[2-0-{2-acetamido-2,3-dideoxy-6-0-octadecanoyl-1-0-((3R)-3-tetracosanoyloxytetradecanoyl)-α-D-glucopyranos-3-yl}-D-lactoyl]-L-alanyl-D-isoglutamine methylester, N-[2-0-{2-acetamido-2,3-dideoxy-1-S-((3R)-3-tetracosanoyloxytetradecanoyl)-1-thio-β-D-glucopyranos-3-yl}-D-lactoyl]-L-alanyl-D-isoglutamine methylester, or N-[2-0-{2-acetamido-2,3-dideoxy-6-0-octadecanoyl-1-S-((3R)-3-tetracosanoyloxytetradecanoyl)-1-thio-β-D-glucopyranos-3-yl}-D-lactoyl]-L-alanyl-D-isoglutamine methylester.

9. An immunoregulating composition comprising a muramyl dipeptide derivative of the formula (I) as defined in claim 1 and a pharmaceutically acceptable carrier.

10. An immunoregulating composition of claim 9 in which the muramyl dipeptide derivative (I) is a compound in accordance with any one of claims 2 to 8.

11. An immunoregulating composition of claim 9 which is used for enhancing in vivo activity of a BCG, hepatitis or influenza virus vaccines.

12. An immunoregulating composition of claim 9 which is used for enhancing in vivo activity of antibacterial agents.

13. An immunoregulating composition of claim 9 which is used for enhancing in vivo activity of antitumor agents.

* * * * *

UNITED STATES PATENT AND TRADEMARK OFFICE
CERTIFICATE OF CORRECTION

PATENT NO. : 5,075,287

DATED : December 24, 1991

INVENTOR(S): Akira Hasegawa

It is certified that error appears in the above-identified patent and that said Letters Patent is hereby corrected as shown below:

Item [73]
Cover page: Change "Nisshin Oil Mills, Inc., Japan" to --The Nisshin Oil Mills, Ltd., Japan--.
Title page, item [57]
In the Abstract: In the first formula (I), insert a bond between the "N" and the ring; change "imminoregulating" to --immunoregulating-- in the last line.

Column 2, line 1: Delete "$R_3S$-" at the beginning of the line.

Column 2, line 7: Insert --(-- before "k" at the beginning of the line.

Column 3, line 67: Change "60 -D" to --$\alpha$-D--.

Column 4, line 2: Change "3-yl)" to --3yl}--.

Column 4, line 11: Change "3-yl)" to --3yl}--.

Column 4, line 17: Delete "1-" at the end of the line.

Column 4, line 23: Change "3-yl)" to --3-yl]--.

Column 4, line 25: Change "{(3R)" to --((3R)--.

Column 4, line 34: Change "3-yl)" to --3-yl]--.

Column 4, line 40: Change "([3R)" to --((3R)--.

Column 4, line 42: Change "3-yl)" to --3-yl}--.

UNITED STATES PATENT AND TRADEMARK OFFICE
CERTIFICATE OF CORRECTION

PATENT NO. : 5,075,287

DATED : December 24, 1991

INVENTOR(S): Akira Hasegawa

Page 2 of 20

It is certified that error appears in the above-identified patent and that said Letters Patent is hereby corrected as shown below:

Column 4, line 49: Change "([3R)" to --((3R)--.

Column 4, line 61: Change "3-yl)" to --3-yl}--.

Column 5, line 4: Change "8" to --ß--.

Column 5, line 9: Change "3-yl)" to --3-yl}--.

Column 5, line 15: Change "{(3R)" to --((3R)--.

Column 5, line 21: Change "3-yl)" to --3-yl}--.

Column 5, line 24: Change "}" to --)--.

Column 5, line 47: Change "octadecanoyl1-" to --octadecanoyl-1- --.

Column 5, line 59: Change "({ 3R )" to --((3R)--.

Column 5, line 64: Change "}" to --)--.

Column 6, line 13: Change "3-yl)" to --3-yl}--.

Column 6, line 23: Change "3-yl)" to --3-yl}--.

Column 6, lilne 55: Change "3-yl)" to --3-yl}--.

Column 6, line 59: Change "3-yl)" to --3-yl}--.

Column 6, line 62: Change "8" to --ß--.

UNITED STATES PATENT AND TRADEMARK OFFICE
CERTIFICATE OF CORRECTION

Page 3 of 20

PATENT NO. : 5,075,287
DATED : December 24, 1991
INVENTOR(S): Akira Hasegawa

It is certified that error appears in the above-identified patent and that said Letters Patent is hereby corrected as shown below:

Column 7, line 5:   Change "(3R)" to --((3R)--.

Column 7, line 23: Change "3-yl)" to --3-yl}--.

Column 7, line 26: Change "o-D" to --α-D--.

Column 7, line 31: Change "3-yl)" to --3-yl}--.

Column 7, line 35: Change "3-yl)" to --3-yl}--.

Column 7, line 56: Change "3-yl)" to --3-yl}--.

Column 7, lines 58-59: Change "eicosa-noyloxytetradecanoyl}" to
          --eicosa-noyloxytetradecanoyl)--.

Column 8, line 7:   Change "3-yl)" to --3-yl}--.

Column 8, line 13: Change "([3R)" to --((3R)--.

Column 8, line 15: Change "3-yl)" to --3-yl}--.

Column 8, line 23: Change "3-yl)" to --3-yl}--.

Column 8, line 29: Change "({3R)" to --((3R)--.

Column 8, line 43: Change "alanyl---isoglutamine" to
          --alanyl- D - isoglutamine--.

UNITED STATES PATENT AND TRADEMARK OFFICE
CERTIFICATE OF CORRECTION

PATENT NO. : 5,075,287
DATED : December 24, 1991
INVENTOR(S): Akira Hasegawa

It is certified that error appears in the above-identified patent and that said Letters Patent is hereby corrected as shown below:

Column 8, line 47: Change "3-yl)" to --3-yl}--.

Column 8, line 59: Change "3-yl)" to --3-yl}--.

Column 8, line 63: Change "glucopyranos-yl" to --glucopyranas-3-yl--.

Column 9, line 3: Change "3-yl)" to --3-yl}--.

Column 9, line 11: Change "3-yl)" to --3-yl}--.

Column 9, line 15: Change "3-yl)" to --3-yl}--.

Column 9, line 26: Change "{(3R)" to --((3R)--.

Column 9, lines 33-34: Change "[2-dodecyl-tetradecanoyl)" to --(2-dodecyltetradecanoyl)--.

Column 9, lines 42-43: Change "[2-dodecyltetradecanoyl)" to --(2-dodecyltetradecanoyl)--.

Column 9, lines 45-46: Change "[2-dodecyltetradecanoyl)" to --(2-dodecyltetradecanoyl)--.

Column 9, lines 51-52: Change "(2-dodecyltetradecanoyl}" to --(2-dodecyltetradecanoyl)--.

Column 9, line 63: Change "3-yl)" to --3-yl}--.

Column 10, line 1: Change "1-S-[2" to --1-S-(2--.

UNITED STATES PATENT AND TRADEMARK OFFICE
CERTIFICATE OF CORRECTION

Page 5 of 20

PATENT NO. : 5,075,287
DATED : December 24, 1991
INVENTOR(S): Akira Hasegawa

It is certified that error appears in the above-identified patent and that said Letters Patent is hereby corrected as shown below:

Column 10, line 8: Change "1-0-2" to --1-0-(2--.

Column 10, line 18: Change "0-[2" to --0-(2--.

Column 10, lines 22-23: Change "3-yl)" to --3-yl}--.

Column 10, line 35: Change "8" to --β--.

Column 10, line 43: Change "}-6-0" to --)-6-0--.

Column 10, line 44: Change "3-yl)" to --3-yl}--.

Column 11, lines 4-5: Change "1-S-[2" to --1-S-(2--.

Column 11: line 23: Change "3-yl)" to --3-yl}--.

Column 11, lines 35-36: Change "3-yl" to --3-yl}--.

Column 11, line 47: Change "1-S-{2" to --1-S-(2--.

Column 11, line 55: Change "1-S-[2" to --1-S-(2--.

Column 11, line 64: Change "lacto-yl]" to --lactoyl]--.

Column 12, lines 8-9: Change "3-yl)" to --3-yl]--.

Column 12, line 11: Change "3-yl)" to --3-yl}--.

Column 12, line 25: Change "3-yl)" to --3-yl}--.

UNITED STATES PATENT AND TRADEMARK OFFICE
CERTIFICATE OF CORRECTION

PATENT NO. : 5,075,287

DATED : December 24, 1991

INVENTOR(S): Akira Hasegawa

It is certified that error appears in the above-identified patent and that said Letters Patent is hereby corrected as shown below:

Column 12, line 28: Change "ß" to --β--.

Column 12, line 29: Change "3-yl)" to --3-yl}--.

Column 12, line 35: Change "3-yl)" to --3-yl}--.

Column 12, line 61: Change "1-S-{2" to --1-S-(2--.

Column 12, line 67: Change "3-yl)" to --3-yl}--.

Column 13, line 1: Change "1-S-[2" to --1-S-(2--.

Column 13, line 50: Change "B-D-L glucopyranos" to --B-D-glucopyranos--.

Column 14, line 24: Change "[(3R)" to --((3R)--.

Column 14, line 31: Change "[(3R)" to --((3R)--.

Column 14, line 42: Change "[(3R)" to --((3R)--.

Column 14, line 47  Delete "c." at the end of the line.

Column 14, line 48: Change "{(3R)" to --((3R)--.

Column 15, line 7: Change "([3R)" to --((3R)--.

Column 15, line 16: Change "3-yl)" to --3-yl}--.

Column 15, line 20: Change "3-yl)" to --3-yl}--.

UNITED STATES PATENT AND TRADEMARK OFFICE
CERTIFICATE OF CORRECTION

PATENT NO. : 5,075,287

DATED : December 24, 1991

INVENTOR(S): Akira Hasegawa

It is certified that error appears in the above-identified patent and that said Letters Patent is hereby corrected as shown below:

Column 15, line 23: Change "octadecanoyloxydodecanoyl}" to --octadecanoyloxydodecanoyl)--.

Column 15, line 24: Change "3-yl)" to --3-yl}--.

Column 15, line 34: Change "octaL" to --octa- --.

Column 15, line 36: Change "3-yl)" to --3-yl}--.

Column 15, line 44: Change "glucoL pyranos" to --glucopyranos--.

Column 15, line 67: Change "3-yl)" to --3-yl}--.

Column 15, line 68: Delete "v," and begin a new paragraph after that deletion and before "N".

Column 16, line 8: Change "[(3R)" to --((3R)--.

Column 16, line 10: Change "3-yl)" to --3-yl}--.

Column 16, lline 45: Change "glucoL pyranos" to --glucopyranos--.

Column 16, line 49: Change "L glucopyranos" to --glucopyranos--.

Column 16, line 51: Change "[(3R)" to --((3R)--.

Column 16, line 53: Change "glucoL pyranos" to --glucopyranos--; change "3-yl)" to --3-yl}--.

Column 16, line 55: Change "{(3R)" to --((3R)--.

UNITED STATES PATENT AND TRADEMARK OFFICE
CERTIFICATE OF CORRECTION

PATENT NO. : 5,075,287
DATED : December 24, 1991
INVENTOR(S): Akira Hasegawa

It is certified that error appears in the above-identified patent and that said Letters Patent is hereby corrected as shown below:

Column 16, line 64: Change "0-D" to --ß-D--.

Column 17, line 7: Change "[(3R)" to --((3R)--.

Column 17, line 39: Change " ⊕ " to --ß--.

Column 17, line 50: Change "({3R" to --((3R)--.

Column 17, line 60: Change "L glucopyranos" to --glucopyranos--.

Column 18, line 2: Change "((3R}" to --((3R)--.

Column 18, line 19: Change "3-r yl}" to --3-yl}--.

Column 18, line 22: Change "dodecanoyloxyhexadecanoyl}" to --dodecanoyloxyhexadecanoyl)--.

Column 18, line 23: Change "glucoL pyranos" to --glucopoyranos--.

Column 18, line 26: Change "(3R)" to --((3R)--.

Column 18, line 29: Change "(3R)" to --((3R)--.

Column 18, line 47: Change "L 3-yl}" to --3-yl}--.

Column 18, line 50: Change "glucoL" to --gluco- --.

Column 18, line 54: Change "[(3R)" to --((3R)--.

Column 18, line 55: Change "glucoi pyranos" to --glucopyranos--.

UNITED STATES PATENT AND TRADEMARK OFFICE
CERTIFICATE OF CORRECTION

Page 9 of 20

PATENT NO. : 5,075,287
DATED : December 24, 1991
INVENTOR(S): Akira Hasegawa

It is certified that error appears in the above-identified patent and that said Letters Patent is hereby corrected as shown below:

Column 18, line 65: Change "[(3R)" to --((3R)--.

Column 18, line 67: Change "L 3-yl}" to --3-yl}--.

Column 19, line 29: Change "glucoL" to --gluco- --.

Column 19, line 41: Change "([3R)" to --((3R)--.

Column 19, line 55: Change "L glucopyranos" to --glucopyranos--.

Column 19, line 59: Change "3-yl)" to --3-yl}--.

Column 19, line 62: Change "[(3R)" to --((3R)--.

Column 19, line 67: Change "3-yl)" to --3-yl}--.

Column 20, line 3: Change "3-yl)" to --3-yl}--.

Column 20, line 7: Change "L 3-yl}" to --3-yl}--.

Column 20, line 10: Change "glucoL" to --gluco- --.

Column 20, line 31: Change "glucoL pyranos" to --glucopyranos--.

Column 20, line 35: Change "3-yl)" to --3-yl}--.

Column 20, line 39: Change "D-L glucopyranos" to --D-glucopyranos--

Column 20, line 46: Change "[(3R)" to --((3R)--.

Column 20, line 58: Change "((3R}" to --((3R)--.

UNITED STATES PATENT AND TRADEMARK OFFICE
CERTIFICATE OF CORRECTION

Page 10 of 20

PATENT NO. : 5,075,287
DATED : December 24, 1991
INVENTOR(S): Akira Hasegawa

It is certified that error appears in the above-identified patent and that said Letters Patent is hereby corrected as shown below:

Column 20, line 59: Delete second hyphen after "glucopyranos".

Column 20, line 63: Change "glucoL pyranos" to --glucopyranos--.

Column 20, line 67: Change "glucoL pyranos" to --glucopyranos--.

Column 21, line 3: Change "3-yl)" to --3-yl}--.

Column 21, line 11: Change "glucoL pyranos" to --glucopyranos--.

Column 21, line 17: Change "{(3R)" to --((3R)--.

Column 21, line 41: Change "[(3R)" to --((3R)--.

Column 21, line 43: Change "glucoL pyranos" to --glucopyranos--.

Column 21, line 53: Change "[(3R" to --((3R)--.

Column 21, line 63: Change "L glucopyranos" to --glucopyranos--.

Column 22, line 3: Change "L glucopyranos" to --glucopyranos--.

Column 22, line 8: Change "r glucopyranos" to --glucopyranos--; change "3-yl)" to --3-yl}--.

Column 22, line 20: Change "((3R}" to --((3R)--.

Column 22, line 21: Change "3-yl)" to --3-yl}--.

Column 22, line 34: Change "tetracosanoyloxy-hexadecanoyl}" to --tetracosanoyloxyhexdecanoyl)--.

UNITED STATES PATENT AND TRADEMARK OFFICE
CERTIFICATE OF CORRECTION

PATENT NO. : 5,075,287

DATED : December 24, 1991

INVENTOR(S): Akira Hasegawa

It is certified that error appears in the above-identified patent and that said Letters Patent is hereby corrected as shown below:

Column 22, line 50: Change "3-yl)" to --3-yl}--.

Column 22, line 64: Change "3-yl)" to --3-yl}--.

Column 24, line 66: Change "2-0-¡2" to --2-0-{2--; change "1-0-[2" to --1-0-(2--.

Column 25, line 10: Change "$[\alpha]_D{}^{25}$" to --$[\alpha]_D^{25}$--.

Column 25, line 30: Change "$[\alpha]_D{}^{25}$" to --$[\alpha]_D^{25}$--.

Column 25, line 39: Change "(III" to -- (III)--.

Column 25, line 45: Change "$[\alpha]_D{}^{25}$" to --$[\alpha]_D^{25}$--.

Column 25, line 46: Change "CHCl$_3$ MeOH" to --CHCl$_3$:MeOH--.

Column 25, line 54: Change "[[3R)" to --((3R)--.

Column 25, line 62: Change "12 ml)" to --(12ml )--.

Column 25, line 64: Change "10 1)" to --10:1)--.

Column 26, line 1: Change "$[\alpha]_D{}^{25}$" to --$[\alpha]_D^{25}$-- and "2 1)" to --2:1)--.

Column 26, line 12: Change "[2-0-¡2" to --[2-0-{2--.

Column 26, line 37: Change "$[\alpha]_D{}^{25}$" to --$[\alpha]_D^{25}$--.

UNITED STATES PATENT AND TRADEMARK OFFICE
CERTIFICATE OF CORRECTION

PATENT NO. : 5,075,287
DATED : December 24, 1991
INVENTOR(S): Akira Hasegawa

It is certified that error appears in the above-identified patent and that said Letters Patent is hereby corrected as shown below:

Column 26, line 38: Insert a comma after "2870".

Column 26, line 51: Change "1.39.7" to --139.7--.

Column 26, line 61: Change "$[\alpha]_D{}^{25}$" to --$[\alpha]_D^{25}$--.

Column 26, line 65: Change "1.38)" to --1.38(--.

Column 27, line 16: Change "102.0°" to --120.0°--.

Column 27, line 17: Change "$[\alpha]_D{}^{25}$" to --$[\alpha]_D^{25}$--.

Column 27, line 40: Change "elute" to --eluate--.

Column 27, line 44: Change "$[\alpha]_D{}^{25}$" to --$[\alpha]_D^{25}$--.

Column 27, line 49: Change "j" to --J--.

Column 27, line 62: Change "353.3" to --35.3--.

Column 27, line 66: Change "1.25.8" to --125.8--.

Column 27, line 68: Change "$[\alpha]_D{}^{25}$" to --$[\alpha]_D^{25}$--.

Column 28, line 27: Change "$[\alpha]_D{}^{25}$" to --$[\alpha]_D^{25}$--.

Column 28, line 34: Change "$\leq$" to --=--.

Column 28, line 39: Change "0((3R)" to --0-((3R)--.

UNITED STATES PATENT AND TRADEMARK OFFICE
CERTIFICATE OF CORRECTION

PATENT NO. : 5,075,287

DATED : December 24, 1991

INVENTOR(S): Akira Hasegawa

It is certified that error appears in the above-identified patent and that said Letters Patent is hereby corrected as shown below:

Column 28, line 59: Change "$[\alpha]_D 25$" to --$[\alpha]_D^{25}$--.

Column 29, line 8: Change "0.15" to --0.115--.

Column 29, line 18: Change "$[\alpha]_D 25$" to --$[\alpha]_D^{25}$--.

Column 29, line 21: Change "H)," to --Hz),--.

Column 29, line 38: Change "DC" to --DCC--.

Column 29, line 44: Change "$[\alpha]_D 25$" to --$[\alpha]_D^{25}$--.

Column 29, line 50: Change "3HO," to --$3H$ ),--.

Column 29, line 56: Change "3yl" to --3-yl--.

Column 30, line 7: Change "$[\alpha]_D 25$" to --$[\alpha]_D^{25}$-- and "0.70" to --0.702--.

Column 30, line 19: Change "tetradecanoyloxy-tetradecanoyl-1" to --tetradecanoyloxytetradecanoyl) -1--.

Column 30, line 34: Change "$[\alpha]_D 25$" to --$[\alpha]_D^{25}$--.

Column 30, line 60: Change "$[\alpha]_D 25$" to --$[\alpha]_D^{25}$--.

Column 31, line 7: Change "(II)" to --(III)--.

Column 31, line 8: Change "408.8" to --408.1--.

UNITED STATES PATENT AND TRADEMARK OFFICE
CERTIFICATE OF CORRECTION

PATENT NO. : 5,075,287

DATED : December 24, 1991

INVENTOR(S): Akira Hasegawa

It is certified that error appears in the above-identified patent and that said Letters Patent is hereby corrected as shown below:

Column 31, line 15: Change "$[\alpha]_D{}^{25}$" to --$[\alpha]_D^{25}$--.

Column 31, line 18: Change "$(DCDl_3)$" to --$(CDCL_3)$--; delete space between "JMeCH$_2$6" and "Hz".

Column 31, line 19: Change "30 CHz" to --20CHz--; change "Mec" to --MeC--.

Column 31, line 20: Change "Hec" to --HeC--.

Column 31, line 22: Change "(s," to --S,--.

Column 31, line 28: Change "Ooctadecanoyl" to --O-octadecanoyl--.

Column 31, line 43: Change "$[\alpha]_D{}^{25}$" to --$[\alpha]_D^{25}$-- and "=2 1)" to --=2:1)--.

Column 31, line 51: Change "$CH_2 7.7 H_2$" to --CH$_2$7.7Hz--.

Column 31, line 65: Change "563.4 mg)" to --(563.4mg)--.

Column 31, line 68: Change "$[\alpha]_D{}^{25}$" to --$[\alpha]_D^{25}$-- and "28 06" to --28.06--.

Column 32, line 5: Change "1.41[d" to --1.41(d--.

Column 32, line 12: Change "J1.2" to --$J_{1,2}$--

Column 32, line 18: Change "alanYl" to alanyl--.

UNITED STATES PATENT AND TRADEMARK OFFICE
CERTIFICATE OF CORRECTION

PATENT NO. : 5,075,287

DATED : December 24, 1991

INVENTOR(S): Akira Hasegawa

It is certified that error appears in the above-identified patent and that said Letters Patent is hereby corrected as shown below:

Column 32, line 32: Change "$[\alpha]_D 25$" to --$[\alpha]_D^{25}$-- and "=2 1)" to --=2:1)--.

Column 32, line 33: Change "2370" to --3270--.

Column 32, line 49: Change "R1" to --$R_1$--.

Column 32, line 57: Change "$[\alpha]_D 25$" to --$[\alpha]_D^{25}$--.

Column 33, line 16: After "was", add --obtained.--.

Column 33, line 18: Change "$[\alpha]_D 25$" to --$[\alpha]_D^{25}$--.

Column 33, line 35: Change "(III" to --(III)--.

Column 33, line 38: Change "15 ml," to --(15ml),--.

Column 33, line 42: Change "$[\alpha]_D 25$" to --$[\alpha]_D^{25}$--.

Column 33, line 45: Insert a colon before "0.88".

Column 33, line 49: Change "CH2CO" to --$CH_2CO$--.

Column 33, line 60: After "mine" insert --methylester--.

Column 34, line 1: Insert a colon after "yield".

Column 34, line 3: Change "$[\alpha]_D 25$" to --$[\alpha]_D^{25}$--.

UNITED STATES PATENT AND TRADEMARK OFFICE
CERTIFICATE OF CORRECTION

PATENT NO. : 5,075,287
DATED : December 24, 1991
INVENTOR(S): Akira Hasegawa

It is certified that error appears in the above-identified patent and that said Letters Patent is hereby corrected as shown below:

Column 34, line 4: Insert a colon between "$Cl_2$" and "MeOH".

Column 34, line 6: Change "[CH]" to --(CH)--.

Column 34, line 7: Insert a colon before "0.88".

Column 34, line 12: Change "10 6" to --10.6--.

Column 34, line 20: Change "(III" to --(III)--.

Column 34, line 21: Change "[465.2" to --(465.2--.

Column 34, line 28: Change "$[\alpha]_D 25$" to --$[\alpha]_D^{25}$--.

Column 34, line 57: Change "$[\alpha]_D 25$" to --$[\alpha]_D^{25}$--.

Column 34, line 58: Change "(OH) 3300 NH)," to --(OH), 3300(NH),--.

Column 34, line 65: Change "$CH_{24\,2}$" to --$CH_2 4.2$--.

Column 35, line 8: Change "(III" to --(III)--.

Column 35, line 13: Change "595.9 mg}" to --(595.9mg)--.

Column 35, line 15: Change "$[\alpha]_D 25$" to --$[\alpha]_D^{25}$--.

Column 35, line 18: Insert a colon before "0.88".

Column 36, line 2: Change "$[\alpha]_D 25$" to --$[\alpha]_D^{25}$--.

UNITED STATES PATENT AND TRADEMARK OFFICE
CERTIFICATE OF CORRECTION

PATENT NO. : 5,075,287

DATED : December 24, 1991

INVENTOR(S): Akira Hasegawa

It is certified that error appears in the above-identified patent and that said Letters Patent is hereby corrected as shown below:

Column 36, line 3: Change "32 00" to --3200--.

Column 36, line 5: Insert a colon before "0.88".

Column 36, line 10: Change "5.13{d," to --5.13(d,--.

Column 37, line 4: In TABLE 1, change "2000-fold dilution" to --20000-fold dilution--.

Column 38, line 44: In TABLE 2, column 4W, row Example 2, change "0.447" to --1.447--.

Column 38, line 45: In TABLE 2, column 4W, row Example 3, change "0.122" to --1.122--.

Column 38, line 59: In TABLE 2, column 5W, row "Aluminum hydroxide gel", change "1.263 to --0.263--.

Column 38, line 65: In TABLE 2, change "8000-fold dilution" to --80000-fold dilution--.

Claim 1:
Col. 39, lines 52-64: delete "In the formula: insert a bond between the ring and the acetamido group as circled below:" and insert in lieu thereof --A muramyl depeptide derivative of the following formula (I) :--. Delete the circle around the bond from the ring to "NH."

UNITED STATES PATENT AND TRADEMARK OFFICE
CERTIFICATE OF CORRECTION

PATENT NO. : 5,075,287

DATED : December 24, 1991

INVENTOR(S): Akira Hasegawa

It is certified that error appears in the above-identified patent and that said Letters Patent is hereby corrected as shown below:

Column 39, Claim 1: Add immediately after the formula and before claim 2 the following:

--wherein "Ala" is
$$-NH-\underset{\underset{CH_3}{|}}{CH}-CO;$$

"isoGln" is
$$-NH-\underset{\underset{CONH_2}{|}}{CH}-Ch_2CH_2CO-;$$

$R^1$ is $R_3O-$ or $R_3S-$ [$R_3$ is
$$-CO-CH_2-\underset{\underset{\underset{\underset{CO-(CH_2)_q-CH_3}{|}}{O}}{|}}{CH}-(CH_2)_k-CH_3$$

(k is an integer from 8 to 12; q is an integer from 10 to 22) or $R_3$ is
$$-CO-\underset{\underset{(CH_2)_n-CH_3}{|}}{CH}-(CH_2)_m-CH_3$$

(m is an integer from 11 to 17; n is an integer from 11 to 17)]; and $R_2$ is hydrogen atom or $-CO-(CH_2)_p-CH_3$ (p is an integer from 8 to 22).--

In Claim 8:
Col. 40, line 33: add --1-- at the end of the line after "octadecanoyl-".

Col. 40, line 38: change "8" to --β--.

UNITED STATES PATENT AND TRADEMARK OFFICE
CERTIFICATE OF CORRECTION

PATENT NO. : 5,075,287

DATED : December 24, 1991

INVENTOR(S): Akira Hasegawa

It is certified that error appears in the above-identified patent and that said Letters Patent is hereby corrected as shown below:

In Claim 8 (continued)

Col. 40, line 54: delete "0" before "lactoyl]".

Col. 40, line 55: begin a new paragraph with "N-[2-O-acetamido-2,3-dideoxy-6-0".

Col. 40, line 57: change "3-yl)" to --3-yl}--.

Col. 40, line 61: change "gluco pyranos" to --glucopyranos--.

Col. 41, line 18: change "3-yl)" to --3-yl}--.

Col. 41, lines 29-30: delete "t-" at the end of line 29 and change "hio" to --thio-- at the beginning of line 30.

UNITED STATES PATENT AND TRADEMARK OFFICE
CERTIFICATE OF CORRECTION

PATENT NO. : 5,075,287
DATED : December 24, 1991
INVENTOR(S) : Akira Hasegawa

It is certified that error appears in the above-indentified patent and that said Letters Patent is hereby corrected as shown below:

Col. 42, line 15: change "3-yl)" to 3-yl]--.

Signed and Sealed this

Twenty-second Day of February, 1994

Attest:

BRUCE LEHMAN

Attesting Officer        Commissioner of Patents and Trademarks